(12) United States Patent
Heaney et al.

(10) Patent No.: US 8,088,573 B2
(45) Date of Patent: Jan. 3, 2012

(54) METHODS AND DEVICES FOR PERFORMING CHEMICAL REACTIONS ON A SOLID SUPPORT

(75) Inventors: Paul Heaney, Solana Beach, CA (US); Chao Lin, San Diego, CA (US); David Opalsky, San Diego, CA (US); Phillip Bruce, III, San Diego, CA (US); Charles Griswold, San Diego, CA (US); Sheila A. Walker, San Diego, CA (US); Ralf Worl, Neustadt in Holstein (DE); Andrzej Maczuszenko, Toronto (CA)

(73) Assignee: Sequenom, Inc., San Diego, CA (US)

( * ) Notice: Subject to any disclaimer, the term of this patent is extended or adjusted under 35 U.S.C. 154(b) by 359 days.

(21) Appl. No.: 12/109,653

(22) Filed: Apr. 25, 2008

(65) Prior Publication Data
US 2008/0286161 A1    Nov. 20, 2008

Related U.S. Application Data

(63) Continuation of application No. 10/412,801, filed on Apr. 11, 2003, now Pat. No. 7,364,897.

(60) Provisional application No. 60/372,711, filed on Apr. 11, 2002, provisional application No. 60/457,847, filed on Mar. 24, 2003.

(51) Int. Cl.
*C12Q 1/68*    (2006.01)
*C12M 3/00*    (2006.01)
*C12M 1/36*    (2006.01)

(52) U.S. Cl. ... 435/6; 435/287.2; 435/288.3; 435/288.4; 435/288.5; 435/303.1; 435/305.1; 435/305.2

(58) Field of Classification Search ........... 435/6, 288.3, 435/288.4, 288.5, 303.1, 305.1, 305.2
See application file for complete search history.

(56) References Cited

U.S. PATENT DOCUMENTS

| 5,100,626 | A | 3/1992 | Levin |
| 5,650,274 | A | 7/1997 | Kambara et al. |
| 5,716,825 | A | 2/1998 | Hancock et al. |
| 5,789,168 | A | 8/1998 | Leushner et al. |
| 6,083,763 | A | * | 7/2000 | Balch ................ 506/9 |
| 6,093,370 | A | 7/2000 | Yasuda et al. |
| 6,168,948 | B1 | * | 1/2001 | Anderson et al. ......... 435/287.2 |
| 6,192,168 | B1 | 2/2001 | Feldstein et al. |
| 6,225,109 | B1 | 5/2001 | Juncosa et al. |
| 6,258,593 | B1 | 7/2001 | Schembri et al. |
| 6,287,850 | B1 | 9/2001 | Besemer et al. |
| 6,521,181 | B1 | * | 2/2003 | Northrup et al. ............. 506/33 |

(Continued)

*Primary Examiner* — Nathan Bowers
(74) *Attorney, Agent, or Firm* — Stephen C. Beuerle; Procopio Cory Hargreaves & Savich LLP

(57) ABSTRACT

Apparatus and methods for carrying out biochemical processes directly on a substrate are provided. A substrate assembly includes a cartridge that removably supports a substrate in a fixed position, and a reaction containment member that is removably located on top of the substrate. The reaction containment member includes one or more cavities that form chambers directly above one or more target locations on the surface of the substrate. The chambers can be used to conduct biochemical processes directly over the substrate, as well as to perform thermal cycling of material contained inside the chamber using a heating element disposed directly on the substrate. The substrate assembly is preferably used in combination with a processing machine that dispenses materials into the chambers and that conducts biochemical reactions of materials contained within the chambers, without requiring the substrate assembly to be moved from one location to another location during the processes.

51 Claims, 30 Drawing Sheets

U.S. PATENT DOCUMENTS

| | | |
|---|---|---|
| 6,548,788 B2 * | 4/2003 | Kellogg et al. ............... 219/543 |
| 6,642,046 B1 | 11/2003 | McGarry et al. |
| 6,649,358 B1 * | 11/2003 | Parce et al. .................... 435/7.2 |
| 6,893,879 B2 | 5/2005 | Petersen et al. |
| 6,964,847 B1 * | 11/2005 | Englert ............................ 435/6 |
| 2004/0043479 A1 | 3/2004 | Briscoe et al. |
| 2004/0179974 A1 * | 9/2004 | Bedingham et al. .......... 422/100 |
| 2005/0112583 A1 | 5/2005 | Patno et al. |

\* cited by examiner

| Reaction Containment Member 120 |
| Substrate 115 |

METHODS AND DEVICES FOR PERFORMING CHEMICAL REACTIONS ON A SOLID SUPPORT

RELATED APPLICATIONS

This application is a continuation of U.S. patent application Ser. No. 10/412,801 filed Apr. 11, 2003, issued as U.S. Pat. No. 7,364,897 on Apr. 29, 2008; and claims the benefit under 35 U.S.C. 119(e) of U.S. provisional application No. 60/372,711 filed Apr. 11, 2002; and U.S. provisional application No. 60/457,847 filed Mar. 24, 2003. The subject matter of these applications is incorporated by reference herein as though set forth in full.

This application is also related to International PCT application No. PCT/US03/11384, filed Apr. 11, 2003. The disclosure of the PCT application is herein incorporated by reference in its entirety.

FIELD OF THE INVENTION

The invention relates to biochemical processing systems and, more particularly, to carrying out biochemical processes on a substrate.

BACKGROUND

Processing of biological materials often involves the automated transfer of sample materials onto reaction points for testing and analysis. Microarrays have been used to execute tests on large batches of genetic samples to generate phenotype associations and improve interpretation of the large data sets that result from such tests. Samples are usually prepared in a tray called a microtiter plate (MTP), which contains an array of wells that each hold a sample of biological material. A variety of liquid reagent materials are combined in the wells and are subjected to various processes, such as, for example, the polymerase chain reaction (PCR) process, which is a method of amplifying DNA for analysis.

According to the PCR process, a small amount of DNA is replicated by mixing DNA samples with various agents and subjecting the samples to a thermal cycling process in which the samples are subjected to alternating series of heating and cooling cycles. In a typical thermal cycling operation, an MTP with samples is placed in a thermal cycler booth, where the MTP plate is heated and cooled, as desired, thereby affecting the contents of the MTP wells. One way of heating and cooling the plate is to place the plate on top of a metal plate that conforms to the underside of the MTP. The metal plate is heated and cooled, which also causes the MTP to heat and cool.

Prior to the thermal cycling process, the sample preparation for PCR typically begins with empty MTPs being delivered to a plate processing station. The various reagents and biological materials are then added to the wells of the MTP, using robotic systems that pick up the MTPs from a plate processing station, add reagents to the biological material samples, and then move the MTP to a next station for further processing. Alternately, a human operator can manually add and mix the reagents and the biological materials. Thus, the wells of an MTP often contain sample materials that are themselves the result of several operations, usually involving the mixing of solutions and other processing in each of the wells, to prepare the sample materials for PCR. The MTP may be moved to several different stations during such operations, such as stations where the MTPs are rinsed and where samples are moved from the wells of one MTP to the wells of another MTP.

After the PCR process is complete for a given set of samples, the resultant sample materials can be subject to one or more additional processes, which often necessitates washing and rinsing of the equipment that was used for the previous processes. The final samples are often placed in an array of spots on a substrate and then are subject to one or more analyses, such as Matrix Assisted Laser Desorption/Ionization mass spectrometry (MALDI-MS), which is known to those of skill in the art. According to the MALDI-MS process, the samples contained in spots on a target plate are dispersed in a matrix material that strongly absorbs light of a certain wavelength. In a vacuum chamber, short pulses of laser light are then focused on to the samples to cause the samples and matrix to volatilize and form ions. The ions formed are accelerated by a high voltage supply and then allowed to drift down a flight tube. Scientists can glean information about the molecular weight of sample components, based on the amount of time it takes for the ions to arrive at the end of the flight tube.

There are a variety of costs that are associated with the aforementioned processes. One such cost is in terms of the relatively large amount of time that it takes to perform the processes, which decreases throughput of sample analysis. The time required to perform the processes is due to a variety of factors. For example, in the thermal cycling process, the cooling and heating of the MTPs can consume a large amount of time, such as on the order of several hours. It also takes time to move the MTPs between the various stations, such as from the mixing stations where the samples are prepared, to the thermal cycling stations where thermal cycling is performed. Another time drain occurs after PCR and other reactions that follow, when the samples are removed from the MTPs and deposited on a substrate for MALDI-MS.

Another cost is in terms of the amount of space required to perform the processes. Currently, several stations are required to be used during the process, each of which consumes space that could be used for other purposes. The various stations also require some mechanism for transferring the samples between the stations, such as in the form of a robotic system or human operators that increase the monetary costs of the processes. Yet another cost relates to the volume of supplies that are needed to perform the processes. For example, the reagents that are used during PCR are quite expensive.

In view of the foregoing, there is a need for improved apparatus and method of processing biological samples that alleviates the various costs associated with such analysis.

SUMMARY

Apparatus and method for carrying out biochemical processes directly on a substrate are provided. A substrate assembly includes a cartridge base that removably supports a substrate in a fixed position, and a reaction containment member that is removably located on top of the substrate. The reaction containment member and the substrate collectively form chambers directly above one or more target locations on the surface of the substrate. The chambers can be used to conduct biochemical processes in place at the target locations over the substrate, as well as to perform thermal cycling of material contained inside the chamber using a heating element disposed directly on the substrate.

The substrate assembly can be used in combination with a processing machine that dispenses materials into the chambers and that conducts biochemical reactions of materials contained within the chambers, without requiring the substrate assembly to be moved from one location to another location during the processes. In this way, a variety of chemical processes, including for example, PCR preparation of reagents and biological materials, can be conducted at a processing machine comprising a solitary processing station preparatory to a MALDI-MS analysis.

Other features and advantages of the present invention should be apparent from the following description of an exemplary embodiment, which illustrates, by way of example, the principles of the invention.

BRIEF DESCRIPTION OF THE DRAWINGS

FIG. 14 is a side view of a reaction containment member juxtaposed with a substrate as they would be arranged in the substrate assembly shown in FIG. 1.

DETAILED DESCRIPTION

A. Definitions

Figure 1:
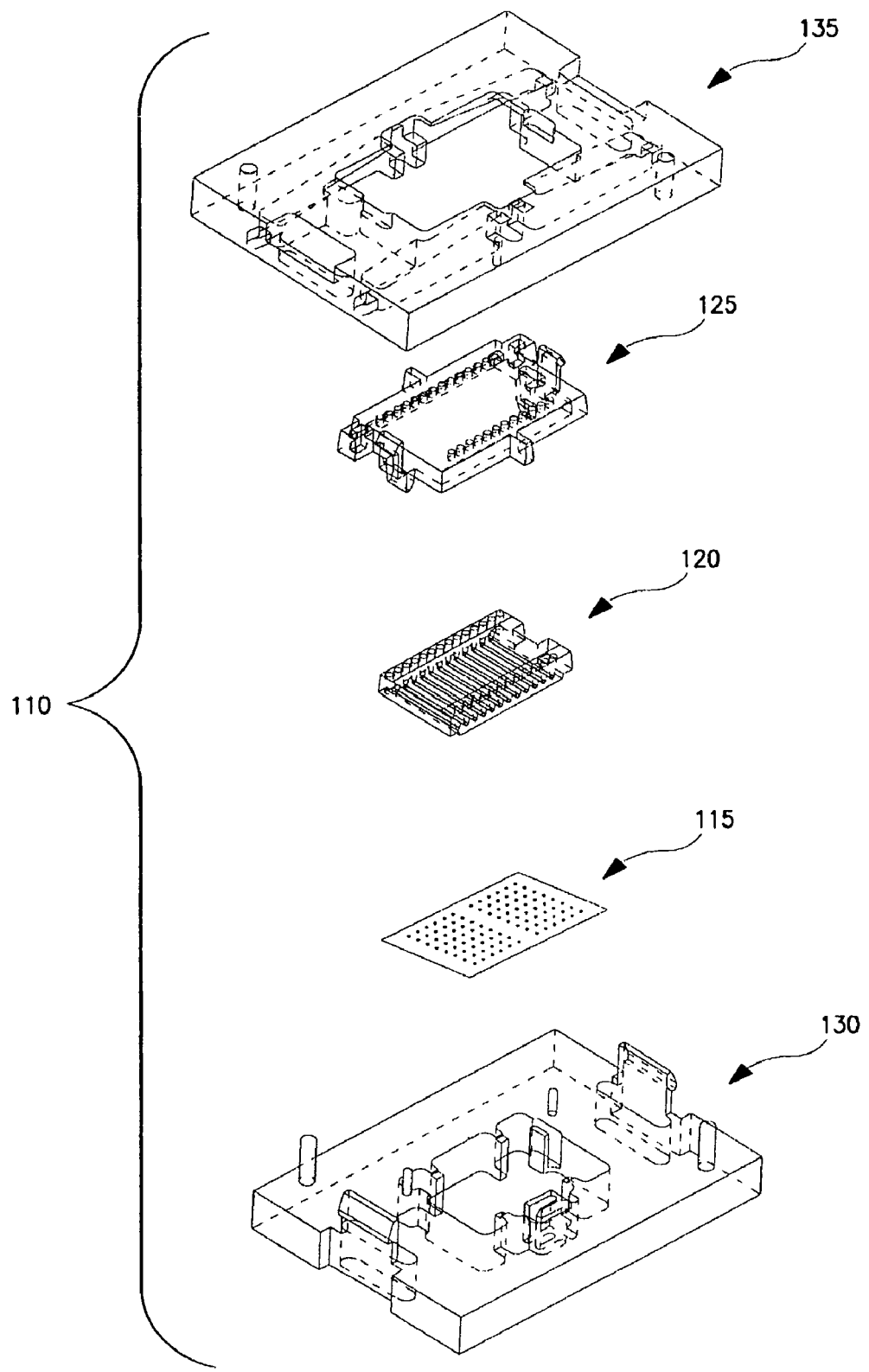
FIG. 1 is an exploded, perspective view of a substrate assembly of the invention.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "biomolecule" or "target biomolecule" refers to any organic molecule such as occurs in a living organism, in particular, macromolecules. Biomolecules include, but are not limited to, nucleic acids, biopolymers, polynucleotides, peptides, polypeptides, proteins, small organic molecules, lipids and carbohydrates, derivatives of such compound groups, and conjugates of such molecules.

As used herein, the phrase "performing one or more reactions of the target biomolecule in the presence of the surface of a substrate" refers to conducting any biochemical reaction (e.g., an amplification or primer extension reaction, or protein:protein binding reaction) in a reaction mixture that is also in contact with at least on surface of a substrate.

As used herein, the phrase "the reaction(s) is performed substantially in solution" refers to reactions in which the interactions between the majority of the reactants occur in solution such that the majority of the reactants and any intermediates are in solution. In particular embodiments, the reaction product(s) is (are) captured onto the surface of the substrate at one or more discrete target detection location(s).

As used herein, the phrase "the substrate comprises one or more target detection location(s) in contact with the solution" refers to the presence of discrete target detection location(s) on the surface of the substrate that is in contact with the reaction mixture, such that each target detection location is also in contact with the reaction mixture during the reaction. The presence of the target detection location in contact with the reaction mixture during the reaction period avoids the need to subsequently physically transfer reaction products from one reaction chamber not having a target detection location to another reaction chamber having the target detection location therein.

As used herein, "target detection location" or "target location" or grammatical variations thereof, refers to a position on a substrate at which a target molecule to be analyzed or detected is located. The target molecule is typically captured using a capture moiety, such as a nucleic acid (e.g., via hybridization) or a protein or antibody via ionic interactions, Van der Waals forces or hydrogen bonds.

As used herein, the phrase "reaction(s) occurs in the presence of", in the context of one, or a subset of all, discretely located solid-phase capture moieties at respective target detection locations, refers to the occurrence of the reactions around, over, under, or adjacent to the target detection locations, such that the reaction mixture containing the biomolecular reactants is in contact with at least one target detection location. Typically, the reactions occur over the target detection locations on the substrate. For example, a particular advantage of the methods provided herein, is the detection of the captured target biomolecules at the same location in which the pre-capture solution phase reactions were performed. Thus, the location of the pre-capture solution phase reactions and the target detection location are the same. This particular feature reduces the cost and time, as well as the amount and the complexity of the machinery required to automatically carry out the reactions in a high throughput format. This feature is accomplished by removing the reaction containment member, which creates one or more reaction chambers or channels in which the solution-phase reactions occur, from the substrate after the target capture step on the target detection locations. Thus, the methods provided herein do not require the physical transfer of solution-phase reaction products to a new target detection location and/or a new solution having capture moiety therein prior to the capture of the target biomolecules. For example, when the substrate is a chip, the chip can advantageously remain stationary throughout the solution phase reactions, at least until reaction product(s) are captured. Once the reaction product(s) are captured, the chip can be moved and/or prepared for detection analysis, such as with MALDI-TOF mass spectrometry.

As used herein, the phrase "non-covalent interaction" refers to any interaction that does not include an interatomic bond characterized by the sharing of 2, 4, or 6 electrons.

As used herein, the phrase "conditions that permit extension of the oligonucleotide" refers to any of the well-known reaction conditions that are used extend primers when hybridized to a template, such as those conditions described in the Examples section herein.

As used herein, "polymorphism" refers to the coexistence of more than one form or allele of a particular nucleic acid, such as a gene or portion thereof. A portion or locus of a nucleic acid segment, such as a gene, at which there are at least two different forms, i.e., two different nucleotide sequences, is referred to as a "polymorphic region". A polymorphic region can be a single nucleotide, the identity of which differs in different alleles. A polymorphic region can also be several nucleotides in length. Polymorphism includes substitutions, insertions, duplications and deletions of nucleotides. A polymorphism can refer to a particular nucleotide(s) or nucleotide sequence occurring at a particular polymorphic site.

As used herein, "polymorphic gene" refers to a gene having at least one polymorphic region.

As used herein, "allele", which is used interchangeably herein with "allelic variant" refers to alternative forms of a nucleic acid, such as a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, the term "subject" refers to any organism that can be the subject of biomolecule analysis. The term subject includes eukaryotic (e.g., yeast, plants, animals, in particular mammals, and in particular humans) and prokaryotic organisms. For example, prokaryotic organisms could be the subject of mutation analyses.

As used herein, "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having the sequence of nucleotides listed herein as SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x.

As used herein, the term "coding sequence" refers to that portion of a gene that encodes an amino acid sequence of a protein.

As used herein, the term "sense strand" refers to that strand of a double-stranded nucleic acid molecule that has the sequence of the mRNA that encodes the amino acid sequence encoded by the doublestranded nucleic acid molecule.

As used herein, the term "antisense strand" refers to that strand of a double-stranded nucleic acid molecule that is the complement of the sequence of the mRNA that encodes the amino acid sequence encoded by the double-stranded nucleic acid molecule.

As used herein, stringency conditions refer to the washing conditions for removing the non-specific probes and conditions that are equivalent to either high, medium, or low stringency as described below:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.
It is understood that equivalent stringencies may be achieved using alternative buffers, salts and temperatures.

As used herein, "target molecule" refers to a molecule, such as, for example a biomolecule, that is of interest to be analyzed. Examples of a target molecule include, but are not limited to, a nucleic acid, e.g., a nucleic acid containing all or a portion of a polymorphic region of a gene of interest, a peptide or protein, a small organic molecule or a carbohydrate.

As used herein, "chamber" refers to an enclosure formed at least by a bottom and, one or more walls which define an interior space that can contain a fluid, such as, for example, a reaction mixture, and/or that can separate one area from another. For example, a chamber may be formed as a depression in the surface of a substrate, such as, for example, a silicon chip. In another example, a chamber may be formed by placing an open end of a hollow cylinder on the surface of a substrate. In another embodiment, a chamber can be formed using one half of a cylinder. In a further example, a chamber may be formed by placing at least two walls parallel to each other on the surface of a substrate to create a channel.

As used herein, "array" refers to a collection of elements, such as nucleic acids. Typically an array contains three or more members. An addressable array is one in which the members of the array are identifiable, typically by position on a solid support. Hence, in general the members of the array will be immobilized to discrete identifiable loci on the surface of a solid phase.

As used herein, "specifically hybridizes" refers to hybridization of a probe or primer preferentially to a target sequence relative to a non-target sequence. Those of skill in the art are familiar with parameters that affect hybridization; such as temperature, probe or primer length and composition, buffer composition and salt concentration and can readily adjust these parameters to achieve specific hybridization of a nucleic acid to a target sequence.

As used herein "nucleic acid" refers to polynucleotides such as deoxyribonucleic acid (DNA) and ribonucleic acid (RNA). The term should also be understood to include, as equivalents, derivatives, variants and analogs of either RNA or DNA made from nucleotide analogs, singlestranded (sense or antisense) and double-stranded polynucleotides. Deoxyribonucleotides include deoxyadenosine, deoxycytidine, deoxyguanosine and deoxythymidine. For RNA, the uracil base is uridine.

As used herein, "mass spectrometry" encompasses any suitable mass spectrometric format known to those of skill in the art. Such formats include, but are not limited to, Matrix-Assisted Laser Desorption/Ionization, Time-of-Flight (MALDI-TOF), Electrospray (ES), IRMALDI (see, e.g., published International PCT Application No. WO 99/57318 and U.S. Pat. No. 5,118,937) Ion Cyclotron Resonance (ICR), Fourier Transform and combinations thereof. MALDI, particular UV and IR, are among exemplary formats.

As used herein, "primer" and "probe" refer to a nucleic acid molecule including DNA, RNA and analogs thereof, including protein nucleic acids (PNA), and mixtures thereof. Such molecules are typically of a length such that they are statistically unique (i.e., occur only once) in the genome of interest. Generally, for a probe or primer to be unique in the human genome, it contains at least 14, 16 or contiguous nucleotides of a sequence complementary to or identical to a gene of interest. Probes and primers can be 10, 20, 30, 50, 100 or more nucleic acids long. Typically, probes or primers are single-stranded nucleic acid molecules.

As used herein, "adjacent" refers to a position 5' to the site of a single nucleotide polymorphism (SNP) such that there could be unpaired nucleotides between that position and the site of the SNP.

As used herein, a support (also referred to as a matrix support, a matrix, an insoluble support or solid support) refers to any solid or semisolid or insoluble support to which a molecule of interest, typically a biological molecule, organic molecule or biospecific ligand is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein may be particulate or may be in the form of a continuous surface, such as a microtiter dish or well, a glass slide, a silicon chip, a nitrocellulose sheet, nylon mesh, or other such materials. When particulate, typically the particles have at least one dimension in the 5-100 µm range or smaller. Such particles, referred collectively herein as "beads", are often, but not necessarily, spherical. Such reference, however, does not constrain the geometry of the matrix, which may be any shape, including random shapes, needles, fibers, and elongated. Roughly spherical "beads", particularly microspheres that can be used in the liquid phase, are also contemplated. The "beads" may include additional components, such as magnetic or paramagnetic particles (see, e.g., Dynabeads® (Dynal, Oslo, Norway)) for separation using magnets, as long as the additional components do not interfere with the methods and analyses herein.

As used herein, matrix or support particles refers to matrix materials that are in the form of discrete particles. The particles can have any shape and dimensions, but typically have at least one dimension that is 100 mm or less, 50 mm or less, 10 mm or less, 5 mm or less, 4 mm or less, 3 mm or less, 2 mm or less, 1 mm or less, 900 µm or less, 800 µm or less, 700 µm or less, 600 µm or less, 500 µm or less, 400 µm or less, 300 µm or less, 200 µm or less, 100 µm or less, 50 µm or less, 40 µm or less, 30 µm or less, 20 µm or less, 10 µm or less, 5 µm or less, 4 µm or less, 3 µm or less, 2 µm or less, 1 um or less, 900 nm or less, 800 nm or less, 700 nm or less, 600 nm or less, 500 nm or less, 400 nm or less, 300 nm or less, 200 nm or less, 100 nm or less, 50 nm or less, 40 nm or less, 30 nm or less, 25 nm or less, and 10 nm or less. The particles typically have a size that is 100 $mm^3$ or less, 50 $mm^3$ or less, 10 $mm^3$ or less, and 5 $mm^3$ or less, 4 $mm^3$ or less, 3 $mm^3$ or less, 2 $mm^3$ or less, and 1 $mm^3$ or less, 900 $\mu m^3$ or less, 800 $\mu m^3$ or less, 700 $\mu m^3$ or less, 600 $\mu m^3$ or less, 500 $\mu m^3$ or less, 400 $\mu m^3$ or less, 300 $\mu m^3$ or less, 200 $\mu m^3$ or less, 100 $\mu m^3$ or less, 50 $\mu m^3$ or less, 40 $\mu m^3$ or less, 30 $\mu m^3$ or less, 20 $\mu m^3$ or less, 10 $\mu m^3$ or less, 5 $\mu m^3$ or less, 4 $\mu m^3$ or less, 3 $\mu m^3$ or less, 2 $\mu m^3$ or less, 1 $\mu m^3$ or less, 900 $nm^3$ or less, 800 $nm^3$ or less, 700 $nm^3$ or less, 600 $nm^3$ or less, 500 $nm^3$ or less, 400 $nm^3$ or less, 300 $nm^3$ or less, 200 $nm^3$ or less, 100 $nm^3$ or less, 50 $nm^3$ or less, 40 $nm^3$ or less, 30 $nm^3$ or less, 20 $nm^3$ or less, 10 $nm^3$ or less, 5 $nm^3$ and may be on the order of cubic nanometers; typically the particles have a diameter of about 1.5 microns and less than 15 microns, such as about 4-6 microns. Such particles are collectively called "beads."

As used herein, "substrate" refers to an insoluble support that can provide a surface on which or over which a reaction may be conducted and/or a reaction product can be retained at an identifiable loci. Support can be fabricated from virtually any insoluble or solid material. For example, silicon, silica gel, glass (e.g. controlled-pore glass (CPG)), nylon, Wang resin, Merrifield resin, Sephadex®, Sepharose®, cellulose, a metal surface (e.g., steel, gold, silver, aluminum, and copper), a plastic material (e.g., polyethylene, polypropylene, polyamide, polyester, polyvinylidenedifluoride (PVDF)). Exemplary substrates include, but are not limited to flat supports such as glass fiber filters, silicon surfaces, glass surfaces, metal surfaces (steel, gold, silver, aluminum, and copper), and plastic materials. The solid support is in any desired form suitable for mounting on the cartridge base, including, but not limited to: a plate, membrane, wafer, a wafer with pits and other geometries and forms known to those of skill in the art. Exemplary supports are flat surfaces designed to receive or link samples at discrete loci, such as flat surfaces with hydrophobic regions surrounding hydrophilic loci for receiving, containing or binding a sample.

B. Exemplary Substrate Assembly

Figure 2:
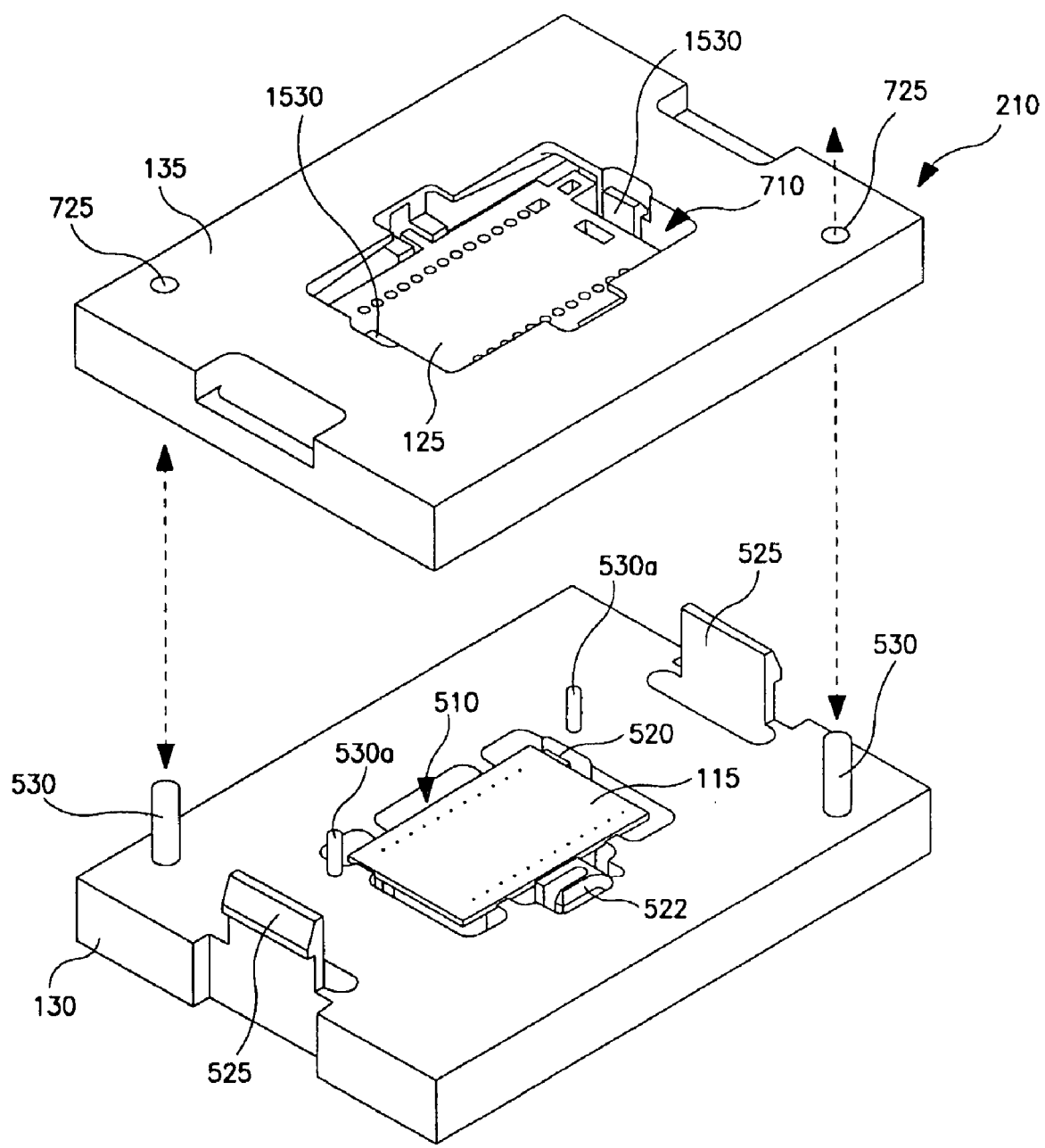
FIG. 2 is a perspective view of a partially-assembled substrate assembly.

FIG. 1 shows an exploded, perspective view of a substrate assembly 110 comprised of a substrate 115, a reaction containment member 120, a reaction containment member back plate 125, a cartridge base 130, and a cartridge cover 135. As shown in FIG. 2, the cartridge cover 135 removably mates with the cartridge base 130 to collectively form a cartridge 210 that removably and securely holds the substrate 115, the reaction containment member 120, and the reaction containment member back plate 125, as described more fully below. The cartridge cover 135 can be removed from the cartridge base 130 to thereby allow the substrate 115 to be removed from the cartridge after processing.

C. Substrate

Figure 3:
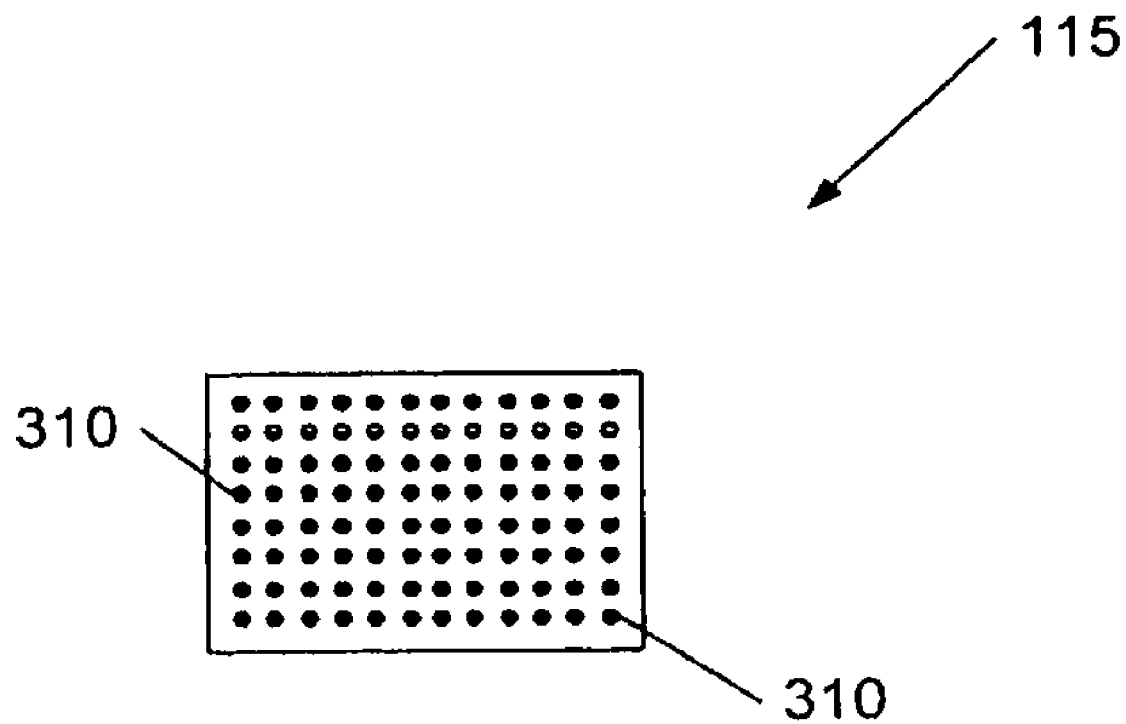
FIG. 3 is a top view of a substrate with target locations that will receive sample material using the substrate assembly.

As shown in FIG. 3, the substrate 115 forms a flat upper surface on which biological samples are deposited to form a plurality of target locations 310. In one embodiment, the substrate is in the form of a chip. The substrate is manufactured of a thermally-conductive material that achieves a fast thermal response and thermal uniformity across the substrate. In this regard, the substrate can be made of a material that has a thermal conductivity that is greater than the thermal conductivity of glass, which is approximately 0.5 Watts/meter-Kelvin (W/mK). In one embodiment, the substrate 115 is made of a material that has a thermal conductivity in the range of approximately 0.5 W/Mk to 450 W/Mk. The substrate 115 may be manufactured of a semiconductive material such as silicon or other materials as will be known to those skilled in the art.

For clarity of illustration in FIG. 3, only two of the target locations are labeled with the reference numeral 310, although the substrate 115 illustrated in FIG. 3 includes ninety-six target locations, arranged into a 12×8 grid. Thus, the substrate 115 has twelve rows of target locations and eight columns of target locations. It should be appreciated that the substrate 115 could have other quantities of target locations arranged in various other configurations. The size of the substrate 115 can vary, although in one embodiment the substrate 115 has a rectangular shape with a length of approximately three centimeters and a width of approximately two centimeters. The target locations 310 can contain a varying volume of biological material. In one embodiment, the target locations 310 occupy an area of 0.002 mm² to 1.0 mm² with oligonucleotide amounts in the range between 10 amol and 10 pmol, although these amounts may vary.

Figure 4:
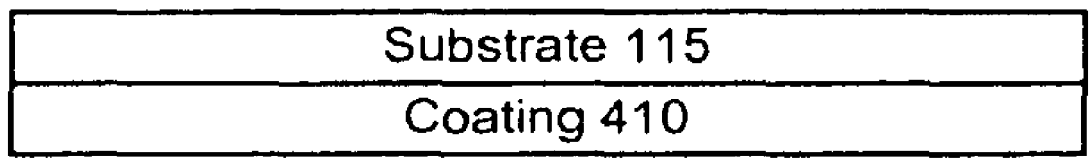
FIG. 4 is a side view of the substrate shown in FIG. 3, showing a resistive coating on the bottom surface of the substrate.

FIG. 4 shows a side view of the substrate 115. A heating element comprised of an electrically-resistive coating 410 is located on a surface of the substrate 115, such as on the surface that is opposed to the surface that contains the target locations. The resistive coating 410 thermally contacts the substrate 115 such that heat can be transferred from the coating 410 to the substrate 115. The resistive coating 410 comprises a film or coating of material that can be heated and cooled to thereby heat and cool the substrate 115. The resistive coating 410 can be made of a material that heats when an electrical current is applied thereto, such as, for example, platinum or titanium tungsten. The resistive coating 410 may have a uniform thickness over the entire bottom surface of the substrate 115 to provide a uniform thermal profile over the surface of the substrate 115. However, the configuration, such as the thickness, of the resistive coating can vary. For example, the resistive coating 410 can be patterned such that the resistive coating 410 is located only on certain regions of the substrate 115 to vary the uniformity of heating over the substrate. Additionally, the resistive coating 410 could be located on the top surface of the substrate 115 where the biological samples are deposited. It should be appreciated that FIG. 4 is not drawn to scale and that the relative sizes of the substrate 115 and resistive coating 410 have been exaggerated for clarity and ease of illustration.

In another embodiment, the substrate 410 is manufactured of a resistive material that heats up when a current is applied to the material. The resistive material may have a thin insulate film applied to a top surface so that target locations can be formed on the surface.

D. Cartridge Base and Cover

Figure 5:
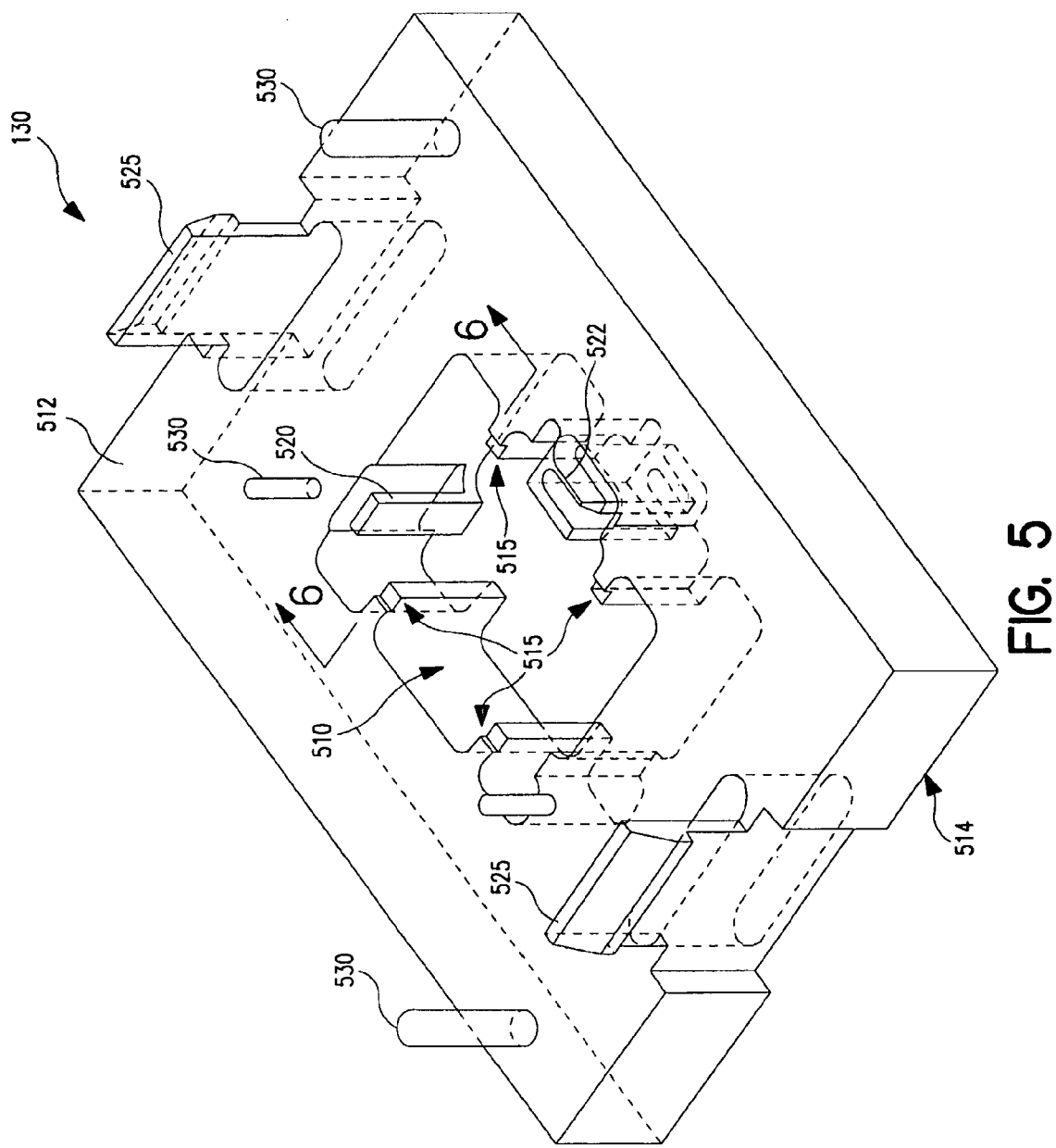
FIG. 5 is a perspective view of a cartridge base of the substrate assembly shown in FIG. 1.

As shown in FIG. 2, the substrate 115 can be mounted on the cartridge base 130 such that the cartridge base 130 removably supports the substrate 115 in a fixed position. The cartridge base 130 supports the substrate 115 in a manner that minimizes any heat flow between the cartridge base 130 and the substrate 115, as described below. FIG. 5 shows an enlarged, perspective view of the cartridge base 130. An aperture 510 extends through the cartridge base 130 from an upper surface 512 to a lower surface 514 of the cartridge base 130. The aperture 510 defines a substrate mounting region where the substrate 115 is mounted on the cartridge base 130.

One or more mounting locations 515 are located on the cartridge base 130, such as around the periphery of the aperture 510. The mounting locations 515 are the regions of the cartridge base 130 that contact the substrate 115 when the substrate 115 is mounted on the cartridge base 130. In one embodiment, the amount of contact area between the substrate 115 and the cartridge base 130 is minimized so that the cartridge base 130 makes very little or no contribution to the thermal mass of the substrate 115 when the substrate 115 is mounted on the cartridge base 130. In this regard, the cartridge base 130 can contact less than 10% of the surface area of one side of the substrate 115, can contact less than 5% of the surface area of one side of the substrate 115, and can contact less than 3% of the surface area of one side of the substrate 115 in order to minimize the likelihood of heat flow between the cartridge base 130 and the substrate 115.

Figure 6:
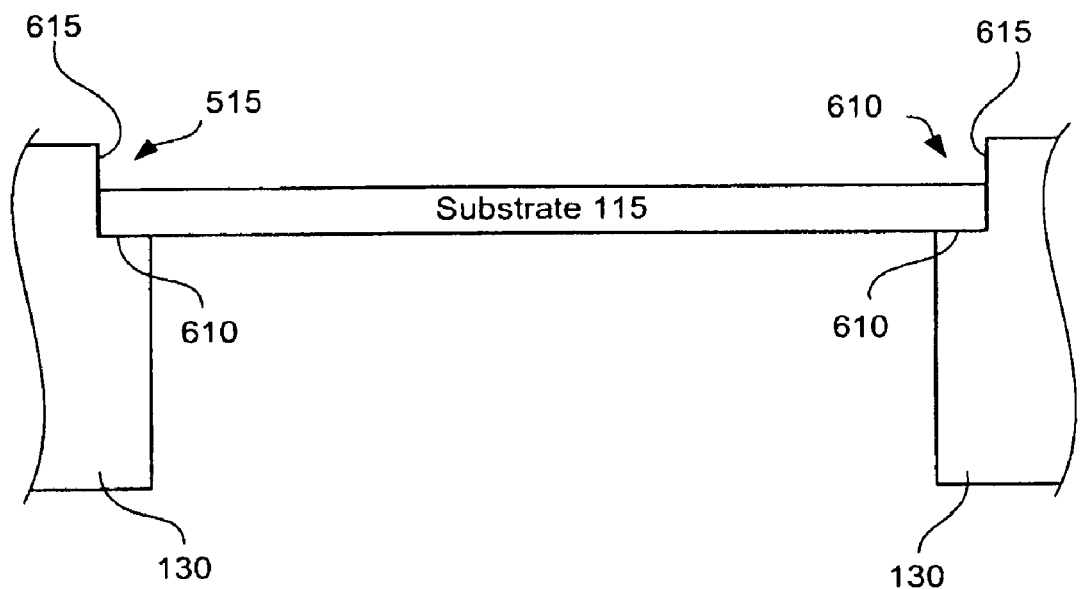
FIG. 6 is a schematic cross-sectional view of the cartridge base along the line 6-6 of FIG. 5, showing a substrate mounted on the cartridge base.

The mounting locations 515 can comprise stepped ledges that collectively form a seat where the substrate 115 can be mounted on the cartridge base 130. This is shown in more detail in the partial-cross sectional view of the cartridge base 130 of FIG. 6. For each mounting location 515, the stepped ledge configuration defines a horizontal wall 610 upon which the substrate 115 sits, and a vertical wall 615 that abuts the edge of the substrate 115 to secure the substrate 115 against movement. The sizes of the wall 610, 615 are selected to provide sufficient support for the substrate 115 while also minimizing the amount of thermal contact between the substrate 115 and the cartridge base 130.

With reference again to FIG. 5, the cartridge base 130 includes at least one securing member 520 that secures the substrate 115 in a fixed position when the substrate 115 is mounted on the mounting locations 515 of the cartridge base 130. The securing member 520 may comprise a finger that is biased to exert a force in a first direction against the edge of the substrate 115 when the substrate 115 is seated on the stepped ledges of the mounting locations 515. The force presses the substrate 115 against one or more of the vertical walls 615 (shown in FIG. 6) so that the substrate 115 can be securely mounted in place on the cartridge base 130.

In one embodiment, the cartridge base 130 also includes a second securing member 522 that exerts a second force against the substrate 115 when the substrate 115 is seated on the stepped ledges of the mounting locations 515. The second securing member 522 exerts the second force in a direction that is transverse to the direction of the force exerted by the first securing member 520 such that the net force exerted on the substrate 115 is toward one of the corners of the substrate 115. Thus, the first securing member 520 and second securing member 522 collectively exert a net force that urges the substrate 115 to sit snug against one of the corners of the aperture 510 in the cartridge base. This increases the likelihood that the substrate 115 will always be positioned in the same location and orientation on the mounting locations, which makes it easier to register the location of the substrate 115 on the cartridge base 130.

FIG. 2 shows the substrate 115 mounted on the cartridge base 130. When mounted on the cartridge base 130, the substrate 115 is suspended over the aperture 510 so that the bottom surface of the substrate 115 is at least partially exposed through the aperture 510. The upper surface of the substrate (i.e., the surface where biological samples are deposited) is thus upwardly exposed when the substrate 115 is mounted on the cartridge base 130. The securing members 520, 522 exert a force on the substrate 115 to secure the substrate in place on the mounting locations 515.

As mentioned, the cartridge base 130 mates with the cartridge cover 135. In this regard, the cartridge base includes one or more mating members 525 (shown in both FIG. 2 and FIG. 5) that mate with corresponding mating members in the cartridge cover 135, as described more fully below. With reference to FIG. 5, each of the mating members 525 may comprise an upwardly-extending tongue having a stepped surface that mates and locks with a corresponding aperture in the cartridge cover 135 to thereby exert a force between the cartridge base 130 and the cartridge cover 135 that securely couples the cartridge base 130 and cartridge cover 135 to one another. It should be appreciated that other means may be used to secure the cartridge base 130 and cartridge cover 135 to each other.

In one embodiment, each mating member 525 include at least two detents, such as stepped surfaces, that secure the cartridge cover 135 in two different secured positions with respect to the cartridge base 130. The stepped surfaces each mate with corresponding apertures in the cartridge cover 135. In the first secured position, the cartridge cover 135 is positioned to press against the substrate 115 sufficient to secure the substrate against dismounting from the mounted position on the cartridge base 130. When in the first secured position, the pressing force that the cartridge cover exerts on the substrate 115 is low enough such that the force does not result in any deformation creep in the material that is used to manufacture the cartridge base and cover. The cartridge cover 135 is positioned in the first secured position during long-term storage or transport of the substrate assembly 110 to reduce the likelihood of any creep occurring in the cartridge components during such storage or transport. In the second secured position, the cartridge cover 135 exerts a higher magnitude of force against the cartridge base 130 (and the mounted substrate 115) than when the cartridge cover 135 is in the first secured position to create a greater level of sealing between the substrate and the reaction containment member. The cartridge cover 135 is in the second secured position when the substrate assembly is used for performing biological reactions.

With reference still to FIG. 5, the cartridge base 130 includes one or more alignment pins 530 that extend upwardly from the cartridge base 130. The alignment pins 530 can be mated with corresponding alignment holes in the cartridge cover 135 (or the reaction containment member back plate 125) to align the cartridge base 130 with the cartridge cover 135 during mating, as described more fully below.

Figure 7:
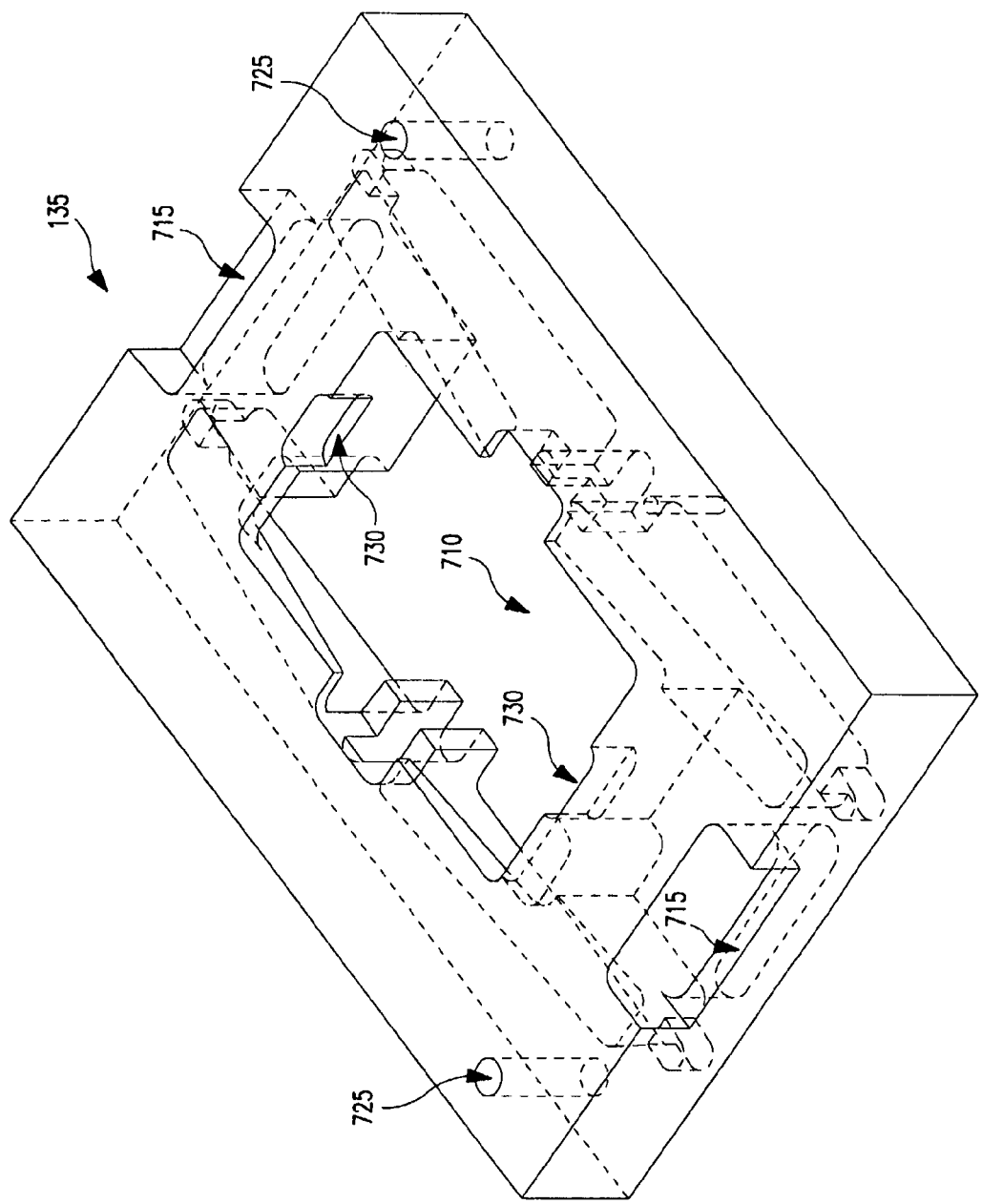
FIG. 7 is a perspective view of a cartridge cover of the substrate assembly shown in FIG. 1.

FIG. 7 shows an enlarged, perspective view of the cartridge cover 135. An aperture 710 extends through the cartridge cover 135. The aperture 710 of the cartridge cover 135 is positioned over the aperture 510 of the cartridge base 130 when the cartridge cover 135 and cartridge base 130 are mated together. Thus, the aperture 710 is positioned directly over the substrate 115 when the substrate 115 is mounted on the cartridge base 130 and the cartridge cover 135 is mated thereto. The cartridge cover 135 includes mating members 715 comprised of slots that mate with the corresponding mating members 525 (shown in FIG. 5) of the cartridge base 130 in a male-female relationship. It should be appreciated that the male members could be located on the cartridge cover 135 with the female members located on the cartridge base 130.

With reference to FIG. 7, one or more alignment holes 725 extend through the cartridge cover 135. Each of the alignment holes 725 aligns with and mates with a corresponding alignment pin 530 of the cartridge base 130. When the alignment holes 725 and alignment pins 530 are aligned with one another, the apertures 515 and 710 also align, as well as the mating members 525 and 715, to thereby facilitate coupling of the cartridge base 130 to the cartridge cover 135, as best shown in FIG. 2. The cartridge cover 135 also includes one or more back plate mounting slots or holes 730 that are located around the periphery of the aperture 710. The mounting holes 730 are used to mount the back plate 125 (shown in FIG. 1) to the cartridge cover 135, as described more fully below.

E. Reaction Containment Member

Figure 8:
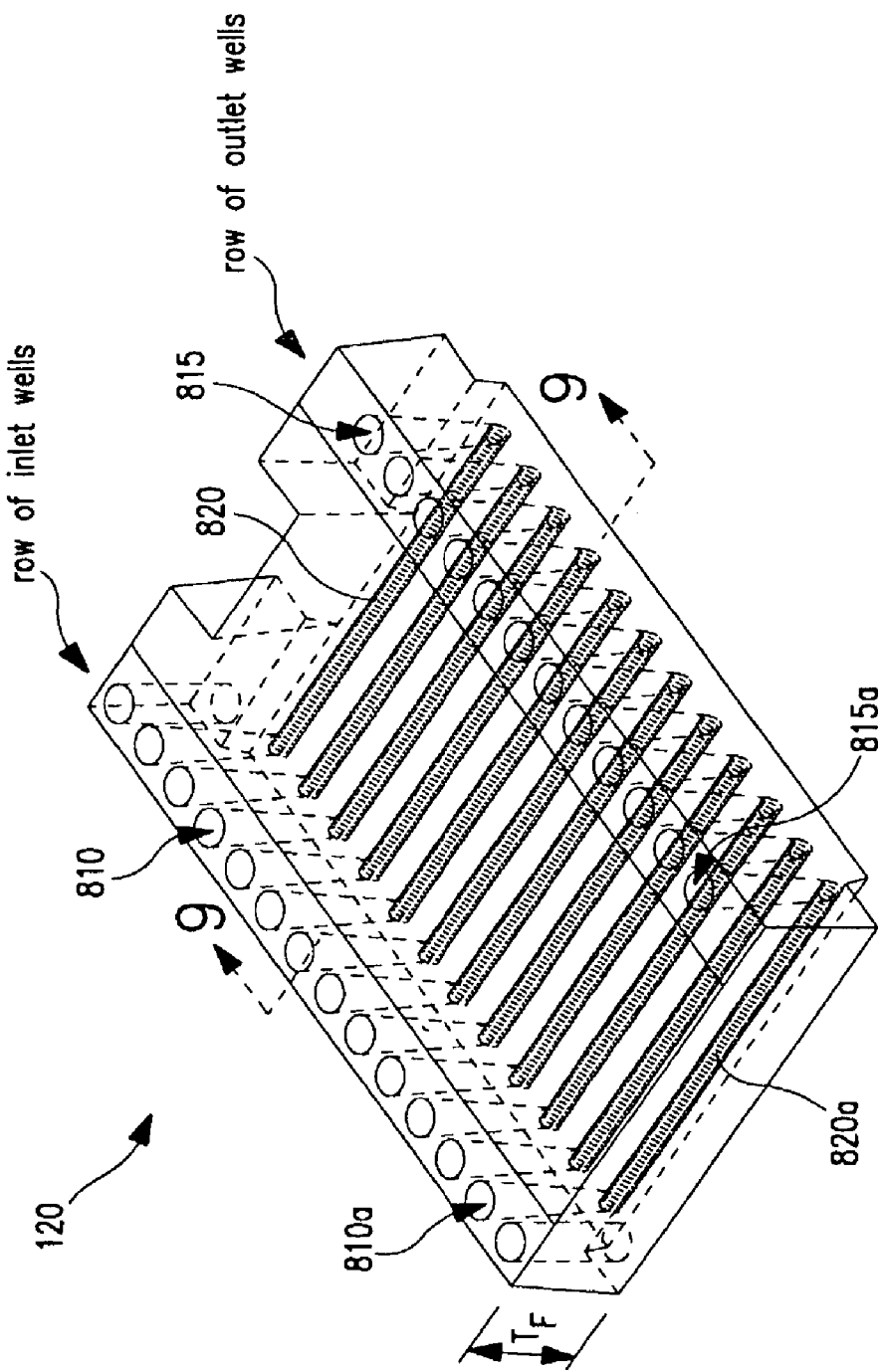
FIG. 8 is a perspective view of a first embodiment of a reaction containment member of the substrate assembly shown in FIG. 1.

FIG. 8 shows a perspective view of a first embodiment of the reaction containment member 120. The reaction containment member 120 shown in FIG. 8 can be juxtaposed with the substrate 115 and mounted in the cartridge 210 to form one or more chambers above the top surface of the substrate 115, as described in more detail below. In this regard, the reaction containment member 120 includes a row of inlet ports 810 that extend along a peripheral edge of the reaction containment member 120 and a corresponding row of outlet ports 815 that extend along a peripheral edge of the reaction containment member 120 that is opposed to the row of inlet ports 810. Each inlet port 810 has a corresponding outlet port 815 so that the inlet ports 810 and outlet ports 815 are arranged in pairs. A flow channel 820 connects a lower end of the inlet port 810 to the lower end of the outlet port 815 for a given inlet port/outlet port pair. For example, in FIG. 8, the pair comprised of the inlet port 810*a* and the outlet port 815*a* includes a flow channel 820*a* that connects the inlet port 810*a* to the outlet port 815*a*. The flow channels 820 are formed by interior surfaces in the reaction containment member 120, as described in more detail below. For clarity of illustration, FIG. 8 only includes reference numeral labels for some of the inlet ports, outlet ports, and flow channels.

The arrangement of the inlet ports 810, outlet ports 815, and flow channels 820 is described in more detail with reference to FIG. 9A, which shows a cross-sectional view of the reaction containment member 120 along the length of one of the flow channels 820. Each of the ports 810, 815 may have an identical size and shape. The inlet ports 810 and outlet ports 815 each comprise a bore hole formed by an interior wall that extends from an upper surface to a lower surface of the reaction containment member 120 so that the ports 810, 815 form openings in the upper and lower surfaces of the reaction containment member 120. The openings in the upper surfaces of the reaction containment member 120 can have a variety of shapes. In one embodiment, the openings are circular and have a diameter in the range of approximately 10 micrometers to 5 millimeters. In one embodiment, the diameter of each opening is 1 millimeter.

The ports 810, 815 are shown having a cross-sectional shape that gradually reduces in size moving downward through the well s, although the size can also be constant. As best shown in the enlarged view of FIG. 9B, the bottom end of each outlet port 815 forms a step 1010, the purpose of which is described below in more detail. The inlet port 815 also has a step, although it is not shown in FIG. 9B. The bottom end of the port 815 opens into the respective flow channel 820.

Figure 10:
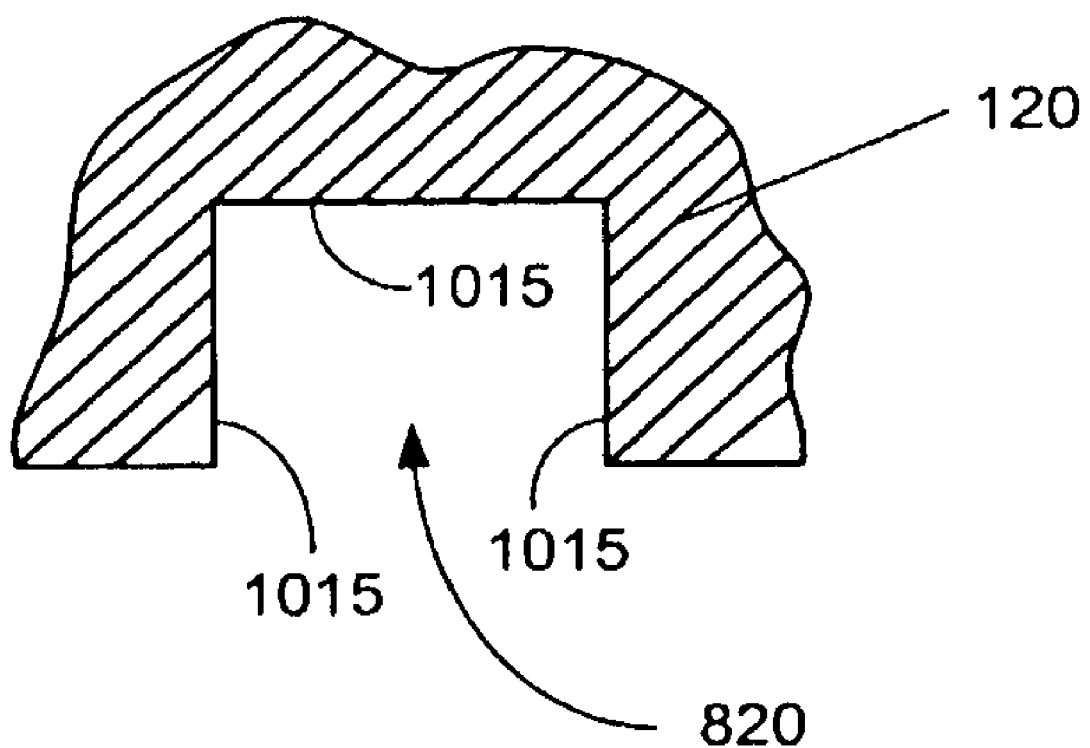
FIG. 10 is a cross-sectional view of a flow channel of the reaction containment member shown in FIGS. 8 and 9A.

FIG. 10 shows a cutaway, cross-sectional view of one of the flow channels 820. The flow channels 820 are formed by a set of interior surfaces 1015 in the reaction containment member 120. The interior surfaces 1015 enclose the flow channel 120 on the sides and on the top but leave the flow channel 120 open on the bottom. FIG. 10 show the interior surfaces 1015 being flat so that the flow channel has a rectangular cross-sectional shape, although it should be appreciated that the interior surfaces 1015 could be rounded or could have other contours to provide the flow channel 820 with different cross-sectional shapes.

With reference again to FIG. 9A, the flow channel 820 extends horizontally from the bottom end of the inlet port 810 to the bottom end of the outlet port 815 so that the ports 810, 815 open into the flow channel 820. In between the ports 810, 815, the flow channel 820 is bounded on an upper periphery by the bottom surface of the reaction containment member 120. The flow channel 820 is open at its bottom such that if the reaction containment member 120 is placed on a flat surface 950, such as shown in FIG. 9A, the flow channel 820 forms an elongate chamber in the form of a tunnel that connects the bottom end of the inlet port 810 to the bottom end of the outlet port 815. The chamber is enclosed on the bottom by the flat surface 950 and on the top by the interior surface of the reaction containment member 120.

The flow channel 820 has a height H (shown in FIG. 9B) in the range of approximately 10 micrometers (µm) to 1 mm. In one embodiment, the height H is approximately 200 µm. A single flow channel 820 can enclose a volume of approximately 10 nanoliters to 100 microliters and, in another embodiment, a volume of 50 nanoliters to 10 microliters.

Figure 9A:
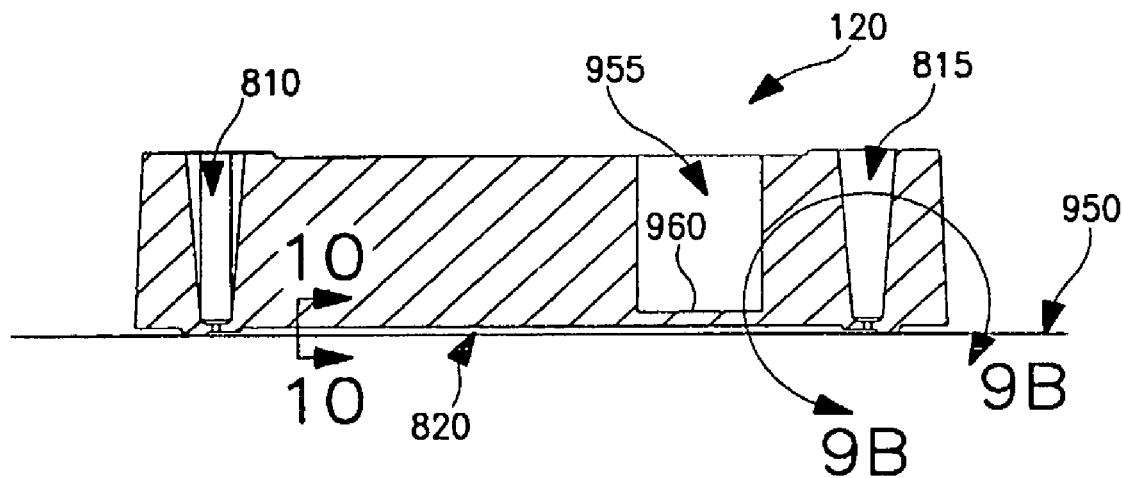
FIG. 9A is a cross-sectional view of the reaction containment member of FIG. 8 along the line 9-9 of FIG. 8, showing a flow channel that connects an inlet port and an outlet port.
Figure 9B:
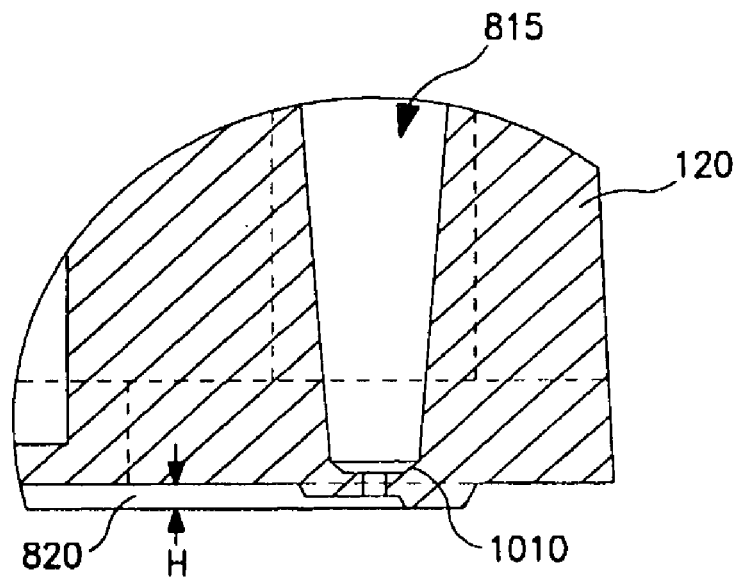
FIG. 9B is an enlarged view of the portion of the reaction containment member contained in the line 10—of FIG. 9A.

As shown in FIG. 9A, one or more pressure relief cavities 955 are 30 located in the reaction containment member 120. The pressure relief cavities 955 are located at interspersed locations in the reaction containment member 120. Each pressure relief cavity 955 is positioned so as to create a region 960 of reduced wall thickness along a portion of the flow channels 820. Thus, if a tunnel formed by a flow channel 820 were to be pressurized, the reduced wall thickness of the region 960 would allow the flow channel 820 to expand and relieve pressure in the tunnel. This may occur during thermal cycling of the reaction containment member 120.

Figure 11:
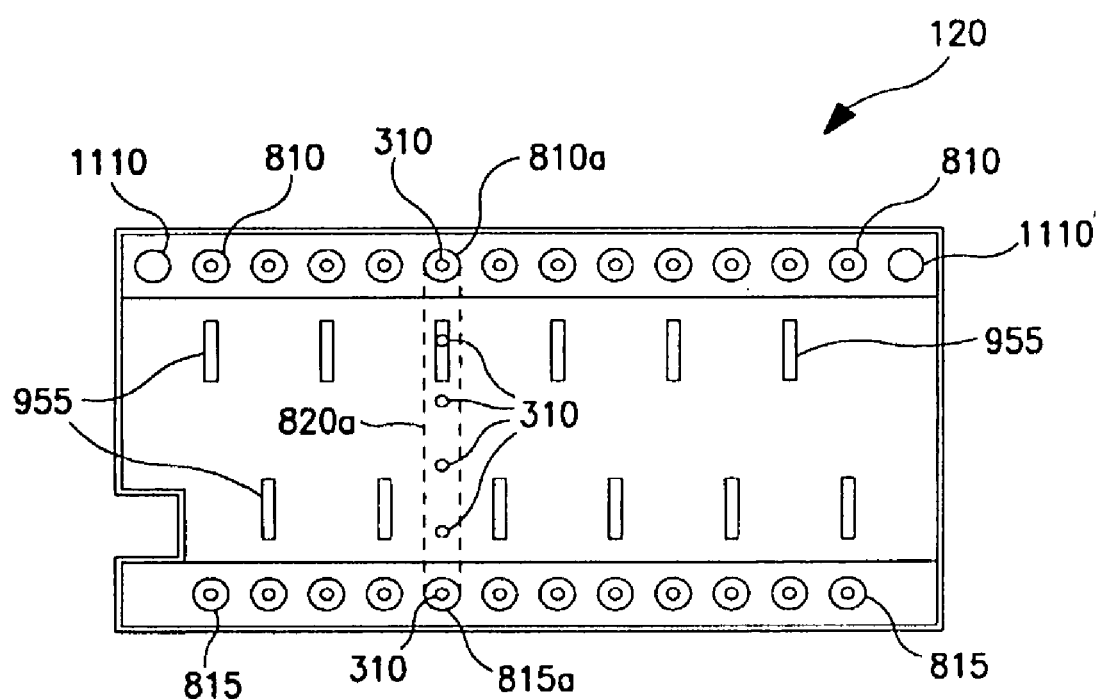
FIG. 11 is a top view of the reaction containment member shown in FIG. 8.

FIG. 11 is a top view of the reaction containment member 120, which has a shape and size that substantially conform to the shape and size of a corresponding substrate 115 when viewed from the top. For example, the reaction containment member 120 shown in FIG. 11 has a rectangular shape that corresponds to the rectangular shape of the substrate 115 shown in FIG. 3, as well as a corresponding size. The inlet ports 810 and outlet ports 815 of the reaction containment member 120 are spatially arranged so that the reaction containment member 120 may be aligned on top of the substrate 115 such that each of the flow channels 820 aligns over a corresponding row of target locations on the substrate 115. When aligned in such a manner, for each row of target locations, the inlet port 810 aligns directly over one of the target locations in a row and the outlet port 815 aligns directly over one of the target locations in a row. In one embodiment, the inlet port 810 aligns with the outermost target location in a row and the outlet port 815 aligns with the opposed outermost target location in the same row. An example of this is shown in FIG. 11, which shows the locations of an exemplary row of target locations 310 on a substrate 115 that is positioned underneath the reaction containment member 120. The row of target locations is aligned under a corresponding flow channel 820*a*, with the flow channel's inlet port 810*a* aligned with the outermost target location in the row and the outlet port 815*a* aligned with the opposed outermost target location in the row. For clarity of illustration, the other rows of target locations on the substrate 115 are not shown, but it should be appreciated that each row would have a corresponding aligned flow channel 820.

With reference to FIG. 11, the reaction containment member 120 may include one or more alignment holes 1110 that facilitate proper alignment of the reaction containment member 120 with the substrate 115. The alignment holes 1110 can mate with corresponding alignment pins on the back plate 125 to align the reaction containment member 120 with the back plate 125. As a further aid to proper alignment of the reaction containment member 120 to the substrate 115, the reaction containment member 120 can be coupled with the reaction containment member back plate 125 to facilitate proper alignment, as described in more detail below. The reaction containment member 120 shown in FIG. 8 has a thickness $T_F$ of approximately 5 mm, although the thickness could be varied. The reaction containment member 120 may be manufactured of a soft material, such as a thermoplastic, or of silicone.

Figure 12A:
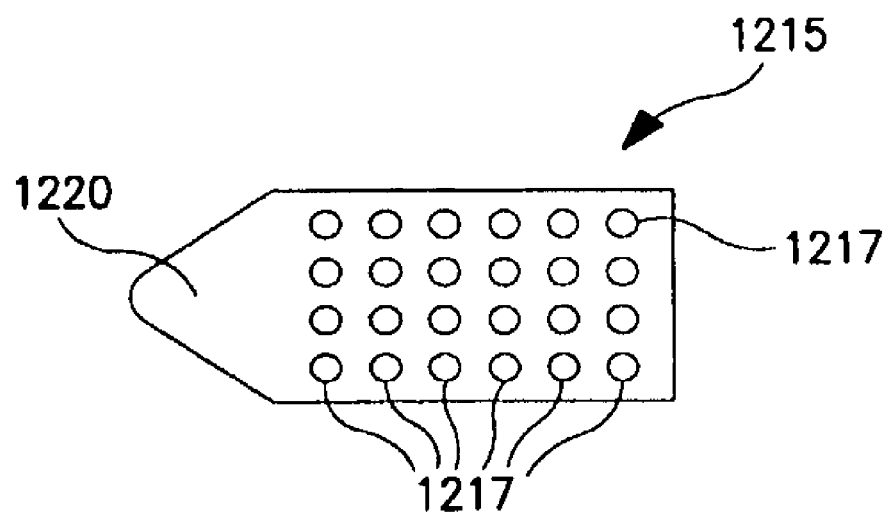
FIG. 12A is a top view of a second embodiment of the reaction containment member, which includes a flow inlet port for each target location of a corresponding substrate.

FIG. 12A shows a top view of another embodiment of the reaction containment member, comprising a reaction containment member 1215. The reaction containment member 1215 includes a plurality of wells 1217 that are arranged in an array. Each well 1217 comprises a bore hole that extends entirely through the reaction containment member 1215 so as to form an opening in the top surface and an opening in the bottom surface of the reaction containment member 1215. The bore holes formed by the wells 1217 are shown in phantom lines in the side view of the reaction containment member 1215 of FIG. 13.

The wells 1217 are spatially arranged such that each well 1217 can be aligned over one or more target locations 310 on a substrate 115. Thus, the reaction containment member 1215 may be overlayed on a substrate 115 such that each well 1217 aligns over at least one corresponding target location 310 on the substrate 115 so as to form a chamber over the target location, the chamber being defined by the upper surface of the substrate and the walls of the well 1217. The reaction containment member 1215 does not require any flow channels, as each well 1217 has one or more corresponding target locations on the substrate.

The reaction containment member 1215 shown in FIG. 12A has twenty-four wells 1217 arranged in a 6×4 grid. Thus, the reaction containment member 1215 could be used with a substrate 115 that has twenty-four target locations arranged in a 6×4 grid and having the same spacing as the wells 1217 on the reaction containment member 1215. It should be appreciated that the quantity and spatial arrangement of the inlet ports 810 can be varied to correspond to that of any substrate. For example, the reaction containment member 1215 could have ninety-six target locations arranged in a 12×8 grid for use with a substrate 115 such as is shown in FIG. 3. The reaction containment member 1215 has a shape and size that corresponds to the shape and size of a corresponding substrate. The reaction containment member 1215 also has a tab section 1220 that can be grabbed when handling the reaction containment member 1215.

Figure 13:
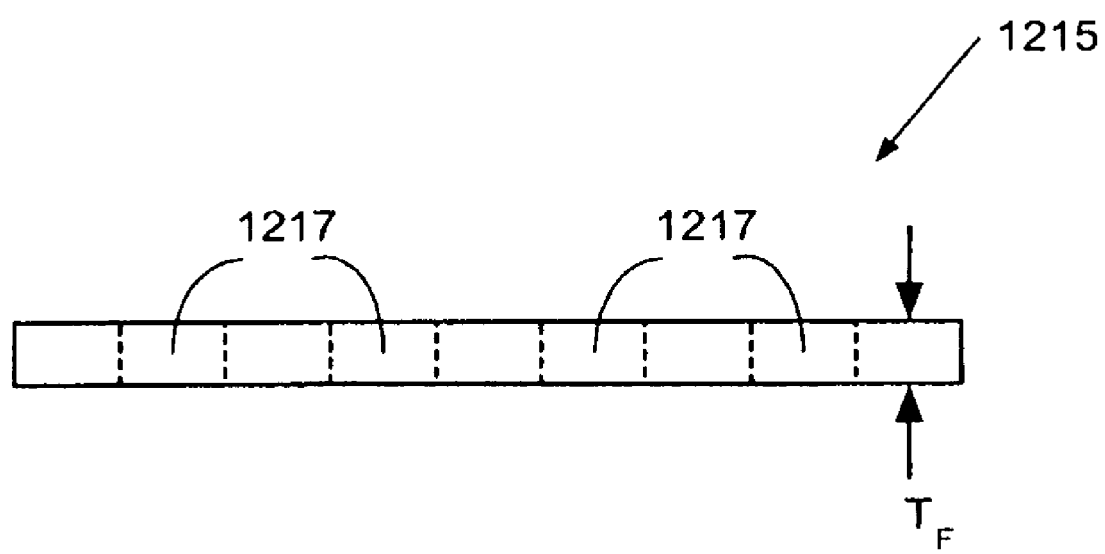
FIG. 13 is a side view of the reaction containment member shown in FIG. 12A.

FIG. 13 shows a side view of the reaction containment member 1215, which has a thickness $T_F$ that can be less than the thickness of the reaction containment member 120 shown in FIG. 8. In one embodiment, the reaction containment member 1215 has a thickness $T_F$ of approximately 1 mm. The reaction containment member 1215 may be manufactured of a wide variety of materials, including silicone and thermoplastics such as rubber.

Figure 12B:
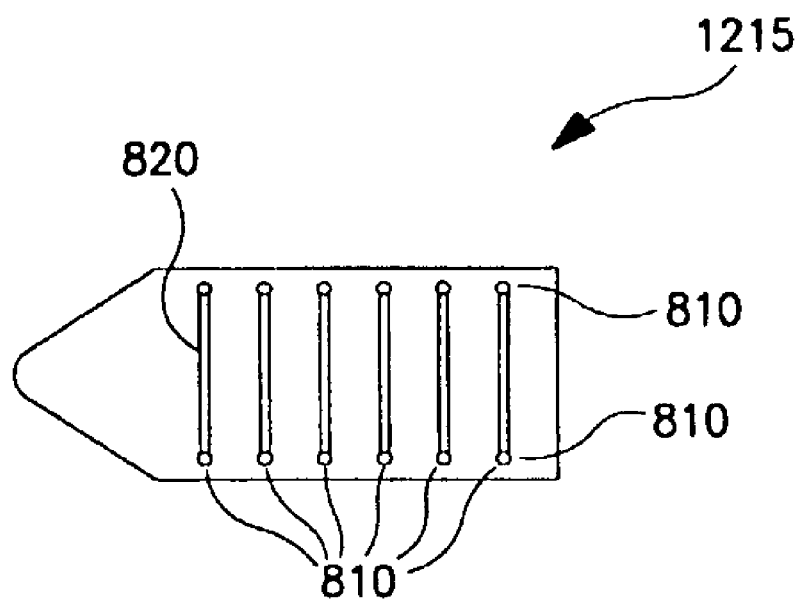
FIG. 12B is a top view of another embodiment of the reaction containment member, which includes flow channels with flow inlet and outlet ports.

It should be appreciated that the reaction containment member 1215 of FIG. 12 could be configured with inlet ports 810, outlet ports 815, and flow channels 820 so that the reaction containment member 1215 would comprise a reaction containment member of the manner shown in FIG. 12B. Additionally, the embodiment of the reaction containment member 120 (shown in FIG. 8) could have multiple wells 1217 according to the arrangement shown in the reaction containment member 1215 of FIGS. 12A and 13.

In use, the reaction containment member 120 (or reaction containment member 1215) is positioned adjacent the substrate 115 such that the bottom surface of the reaction containment member 120 is juxtaposed with the top surface of the substrate 115, as shown in FIG. 14. When using the embodiment shown in FIG. 8, the reaction containment member 120 is aligned with the substrate 115 so that each flow channel 820 in the reaction containment member 120 is positioned directly over a corresponding row of target locations on the substrate so as to form an elongate chamber over the row of target locations, as described in more detail below. If the embodiment of the reaction containment member 1215 is used, then the reaction containment member 1215 is aligned with the substrate 115 so that each well 1217 on the reaction containment member 1215 is positioned over at least one corresponding target location 310 on the substrate 115 so as to form a chamber over the target location. This is described in more detail below.

F. Reaction Containment Member Back Plate

Figure 15:
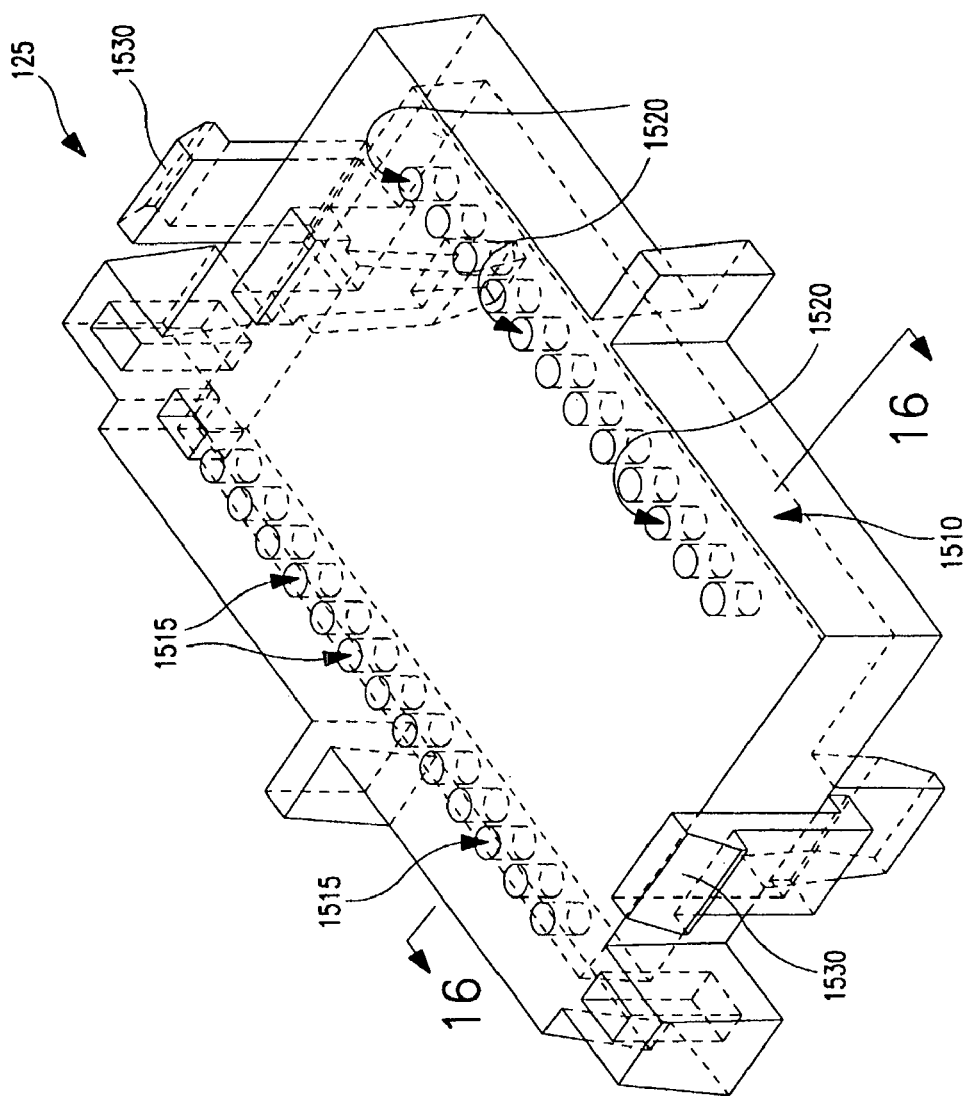
FIG. 15 is a perspective view of a reaction containment member back plate that supports the reaction containment member in the substrate assembly shown in FIG. 1.

The reaction containment member 120 can be secured to the substrate 115 as shown in FIG. 14 in a variety of manners, such as by using adhesive that is located between the bottom surface of the reaction containment member 120 and the top surface of the substrate 115. In one embodiment, a reaction containment member back plate 125 is used to secure the reaction containment member 120 over the substrate 115 so that the reaction containment member 120 correctly aligns with the substrate 115. FIG. 15 is a perspective view of the reaction containment member back plate 125, which defines a seat 1510 in which the reaction containment member 120 can be positioned and secured, as described more fully below with respect to FIG. 16.

The reaction containment member back plate 125 has a plurality of inlet ports 1515 that align with the inlet ports 810 of the reaction containment member 120 when the reaction containment member is positioned in the seat 1510. The reaction containment member back plate 125 also has a plurality of outlet ports 1520 that align with the outlet ports 815 of the reaction containment member 120 when the reaction containment member is positioned in the seat 1510. The reaction containment member back plate 125 also includes one or more mating members 1530, such as upwardly extending fingers, that mate with the cartridge cover 135 to secure the reaction containment member back plate 125 thereto. The reaction containment member back plate 125 is shown secured to the cartridge cover 135 in FIG. 2.

Figure 16:
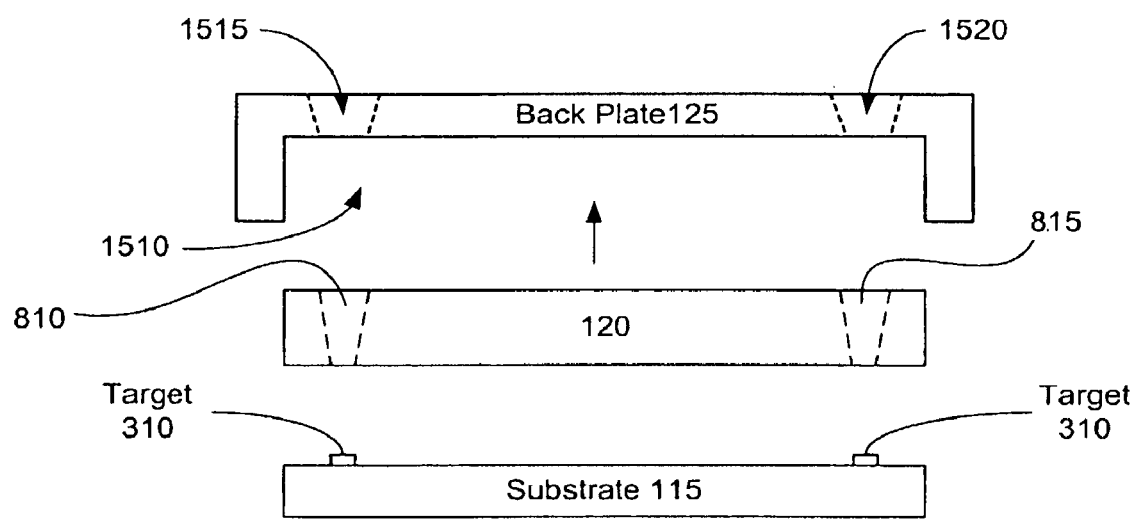
FIG. 16 is a cross-section view of the reaction containment member back plate along the line 16-16 of FIG. 15.

FIG. 16 shows a cross-sectional view of the reaction containment member back plate 125. The back plate 125 is shaped to define a lower cavity that forms a seat 1510 that is sized to receive therein the reaction containment member 120, which is shown in FIG. 16 immediately below the back plate 125. The reaction containment member 120 fits snug within the seat 1510 and can be secured within the seat 1510 using adhesive or through a press-fit. The inlet ports 1515 and outlet ports 1520 of the back plate 125 will align with the corresponding inlet ports 810 and outlet ports 815, respectively, on the reaction containment member 120 when the reaction containment member 120 is properly positioned within the seat 1510. The substrate can then be positioned below the reaction containment member so that the targets 310 properly align below the inlet and outlet ports.

G. Assembling of Cartridge

With reference again to FIGS. 1 and 2, the substrate assembly 110 is assembled by first mounting the substrate 115 on the cartridge base 130 as described above with respect to FIGS. 5 and 6. FIG. 2 shows the substrate 115 mounted on the cartridge base 130, wherein the substrate 115 is positioned over the aperture 510 with the bottom surface of the substrate 115 facing downward through the aperture 510 and the top surface of the substrate 115 (i.e., the surface where biological samples are deposited) facing upward.

The reaction containment member 120 is then positioned on top of the substrate 115 so that the inlet ports 810, outlet ports 815, and flow channels 820 align with the target locations on the substrate 115 as described above. If the reaction containment member 1215 is used, then it is positioned on top of the substrate so that each of the wells 1217 aligns over at least one corresponding target location on the substrate 115. As mentioned, the reaction containment member 120 may be positioned on the substrate 115 by using adhesive.

In another embodiment, the reaction containment member 120 is first coupled to the reaction containment member back plate 125 by inserting the reaction containment member 120 into the seat 1510 of the back plate in the manner shown in FIG. 16. Once the reaction containment member 120 is coupled to the back plate 125, the back plate 125 can then be attached to the cartridge cover 135 by inserting the mating members 1530 in the back plate into corresponding slots in the cartridge cover 135, as shown in FIG. 2. In one embodiment, the mating arrangement between the back plate 125 and the cartridge cover 135 allows the back plate 125 to have some degree of movement relative to the cartridge cover 135 such that the back plate 125 "floats" in relation to the cartridge cover 135. The back plate 125 can have a range of movement of at least approximately 2 millimeters along three axes relative to the cartridge cover 135. This facilitates proper registration between the back plate 125/containment member 120 and the substrate 115, as described below. The back plate 125 may also have some degree of rotational movement relative to the cartridge cover 135.

After the back plate 125 and the reaction containment member 120 are attached to the cartridge cover 135, the cartridge cover 135 is then secured to the cartridge base 130. As mentioned, the cartridge base 130 includes alignment pins 530 that mate with corresponding alignment holes 725 in the cartridge cover 135 to facilitate proper alignment and registration of the cartridge cover and base, as well as proper registration of the reaction containment member 120 with the substrate 115. The alignment pins 530 include special alignment pins 530a (shown in FIG. 2) that mate with corresponding alignment holes in the back plate 125.

As the cartridge cover 135 is moved downward into a mating engagement with the cartridge base 130, the alignment pins 530a slide into engagement with the holes in the back plate 125. As mentioned, the back plate 125 can move with respect to the cartridge cover 135 and the cartridge base 130 so that back plate 125 (and the attached reaction containment member 120) can move into proper registration with the substrate 115 as the cartridge cover 135 is mated with the cartridge base 130. The substrate 115 can also mate with the back plate 125 in a press-fit fashion to ensure proper alignment. Again, the back plate 125 moves into proper alignment with the substrate as the cartridge cover 135 is coupled to the base 130.

Figure 17:
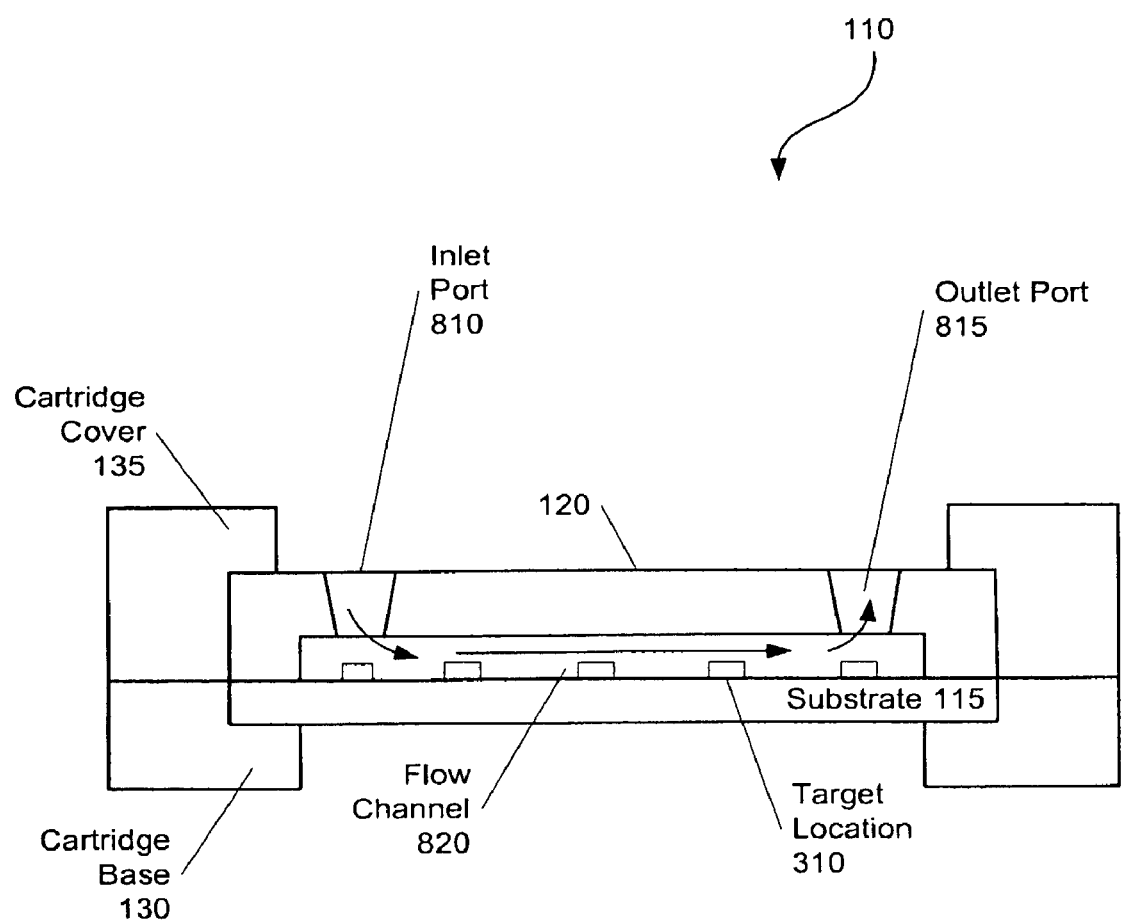
FIG. 17 is a schematic cross-sectional view of the substrate assembly, showing a flow channel that connects an inlet port to an outlet port, with a row of target locations of a substrate positioned within the flow channel.

FIG. 17 is a schematic cross-sectional view of an assembled substrate assembly 110. Some of the structural details of the components of the substrate assembly 110 have been omitted and the relative sizes of the various components have been exaggerated for clarity and ease of illustration in FIG. 17. The substrate 115 is mounted on the cartridge base 130 with the reaction containment member 120 disposed on top of the substrate 115 and secured in place by the cartridge cover 135 (the reaction containment member back plate 125 is not shown in FIG. 17, although it may be used). The flow channel 820 of the reaction containment member 120 is located over a row of target locations 310, which are represented in FIG. 17 as rectangles within the flow channel 820. The flow channel 820 thus forms an elongate chamber that encloses the row of target locations 310 and that has an inlet through the inlet port 810 and an outlet through the outlet port 815.

A fluid may be flowed through the flow channel 820 by injecting the fluid through the inlet port 810 and allowing the fluid to flow out of the flow channel 820 through the outlet port 815, as exhibited by the arrows in FIG. 17.

Figure 18:
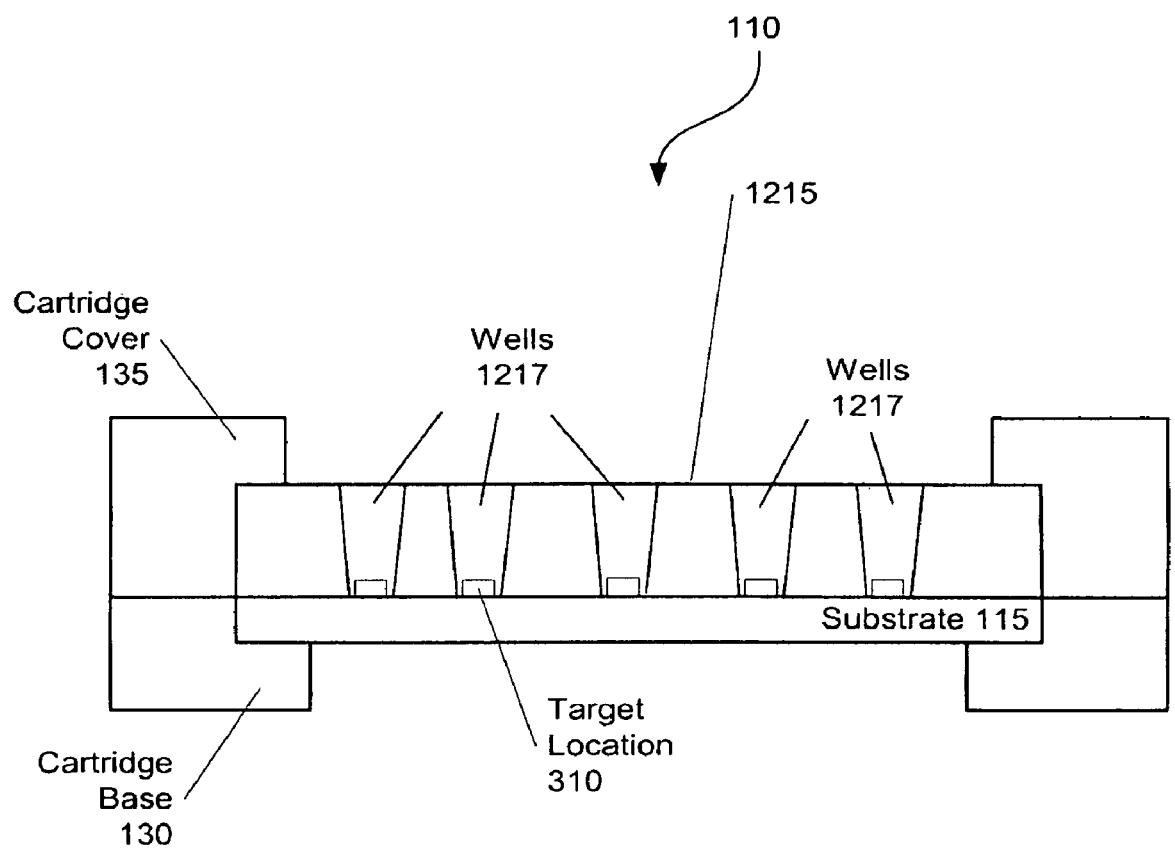
FIG. 18 is a schematic cross-sectional view of the substrate assembly, showing a plurality of inlet ports that are each aligned over a corresponding target location of a substrate.

FIG. 18 is a schematic cross-sectional view of an assembled substrate assembly 110 using the embodiment of the reaction containment member 1215 that was shown in FIGS. 12A and 12B. The reaction containment member 1215 includes multiple wells 1217, which are each aligned over a corresponding target location. Each of the wells 1217 forms a chamber that contains a corresponding target location 310.

H. Processing of Samples Using Substrate Assembly

The substrate assembly 110 can be used to deposit biological samples on target locations of the substrate 115 and to also bathe the target locations with various materials, such as reagents, in order to conduct chemical reactions with the materials within the chambers formed over the substrate. This can be accomplished by locating the substrate assembly 110 on a substrate processing system, such as the machine 1910 shown in FIG. 19. The machine 1910 includes a structure such as a table that defines a substantially horizontal surface 1915 that forms a work station where the substrate assembly 110 containing the substrate 115 can be mounted. The substrate assembly 110 can be positioned on the surface 1915 with the upper or top side of the substrate assembly 110 facing upward such that the inlet ports 810 and outlet ports 815 are facing upward, or such that the openings in the wells 1217 are facing upward.

The machine 1910 also includes one or more movable dispensers, such as a nanodispenser 1920 and a microdispenser 1922, that comprise one or more dispensing nozzles that can be inserted into the inlet ports 810 of the reaction containment member 120 or into the wells 1217 in a well-known manner. In one embodiment, the nanodispenser 1920 can dispense fluids up to a lower volumetric limit of about 1 nanoliter and the microdispenser can dispense fluids up to a lower volumetric limit of about 0.5 microliter μL, although it should be appreciated that the dispensing volumes may vary.

The dispensers 1920, 1922 are mounted on a single dispensing head 1925 that is movably mounted on a support structure 1930, which extends upwardly from the surface 1915 and suspends the dispensing head 1925 over the surface 1915. Alternately, the dispensers 1920, 1922 can be mounted on separate dispensing heads. The support structure 1930 can be movably mounted on the table 1902 such that the support structure can move along a direction defined by a first horizontal axis 1935 with respect to the substrate assembly 110. The dispensing head 1925 is movably mounted on the support structure 1930 such that the dispensing head can move with respect to the substrate assembly along a direction defined by a second axis 1936 that extends in a vertical direction. The dispensing head 1925 can also move along a third axis with respect to the substrate assembly such that the dispensers 1920, 1922 can be moved along three different axes with respect to the substrate assembly 110. Thus, the dispensers 1920, 1922 can be moved into engagement with the inlet/outlet ports or wells of the substrate assembly 110 when it is located on the work station of the surface 1915. The dispensers 1920, 1922 can also be moved to various locations on the work surface 1915 to gain access to other items on the work surface 1915. In one embodiment, the movement of the dispensing head 1925 and the support structure 1930 can be robotically and remotely controlled in a well-known manner.

The surface 1915 is sufficiently large to provide space to support additional items beside the substrate assembly 110. For example, the surface 1915 can have sufficient space for a microtiter plate 1937 that includes a plurality of wells for containing fluids, such as reagents or other materials. The dispensers 1920, 1922 can be moved to a position such that the tips of the dispensers can be dipped into the wells of the microtiter plate 1937 so as to aspirate materials from the wells. The dispensers 1920, 1922 can then be moved into an engagement position wherein the tips of the dispensers are inserted into the wells or inlet ports of the substrate assembly 110 to inject material into the wells or ports. The surface 1915 or some other portion of the machine 1910 can also include other wells or containers that contain additional materials, such as water for bathing the dispensers 1920, 1922.

The machine 1910 also includes a thermal cycler that can be used to cycle the temperature of a substrate that is disposed in a substrate assembly 110 positioned on the work station of the surface 1915. A particular embodiment of the thermal cycler is described more further below.

Advantageously, a variety of processes, including PCR and other chemical processes, can be performed on the biological materials contained in the target locations of a substrate using the machine 1910 without moving the substrate from the work station of the machine 1910. A material, such as a reagent, may be dispensed from the dispenser and flowed into the inlet ports. 810 so that the material flows over the corresponding target locations of the inlet ports 810. Where the reaction containment member 120 having a flow channel 820 is used, then a single inlet port 810 can be used to flow a reagent over an entire row of target locations, such as is shown in FIG. 17. Alternately, the reaction containment member 1215 can be used and the target locations can each be individually exposed using a dedicated inlet port 810 for each target location.

Figure 20:
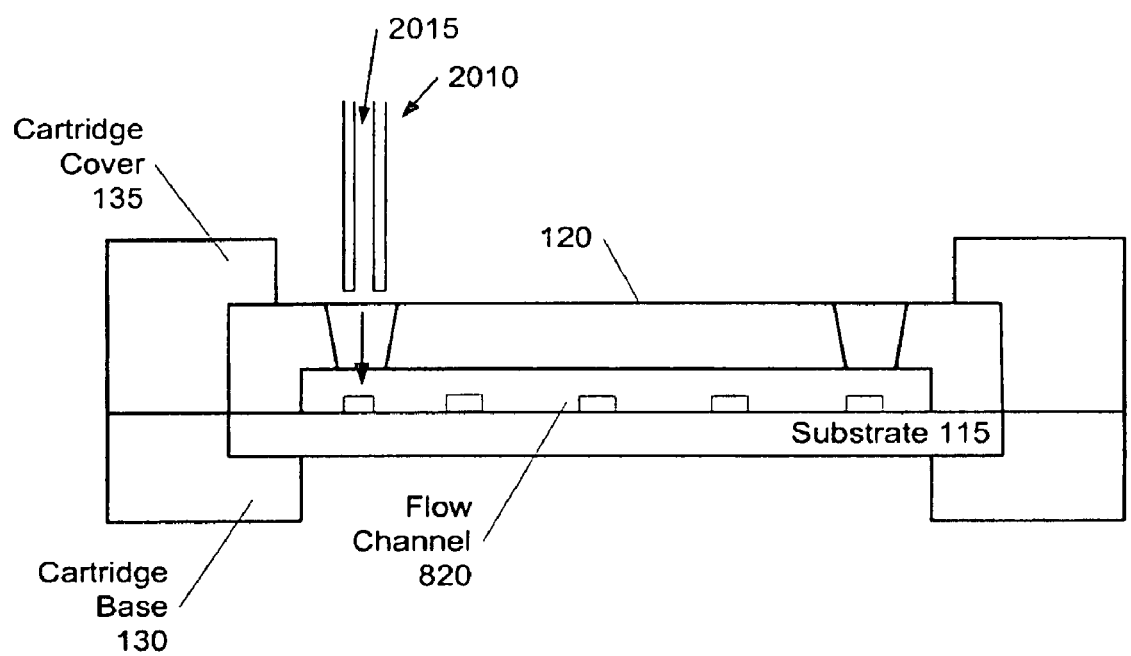
FIG. 20 is a schematic cross-sectional view of the substrate assembly, showing a first way of sealing inlet ports and outlet ports of a reaction containment member using a hollow sealing pin.

In certain situations, it may be necessary to seal the inlet and/or outlet ports of the flow channel. The sealing of the ports may be accomplished in various manners. In one embodiment, shown in FIG. 20, each of the inlet ports and/or outlet ports is sealed with a sealing pin 2010 that is inserted into the port to act as a plug to the port. The sealing pin 2010 can include an internal shaft 2015 that is open at a bottom end through which excess air can escape as the sealing pin 2010 is inserted into the port. During sealing, the sealing pin 2010 is pushed downwardly into the port so that the pin 2010 plugs the port either through an oversized press-fit or by pinching downward on the step 1010 (shown in FIG. 9B) to pinch the port shut at the bottom. A set of solid sealing pins can also be used to seal the wells in the microtiter substrate embodiment of the reaction containment member.

Figure 21:
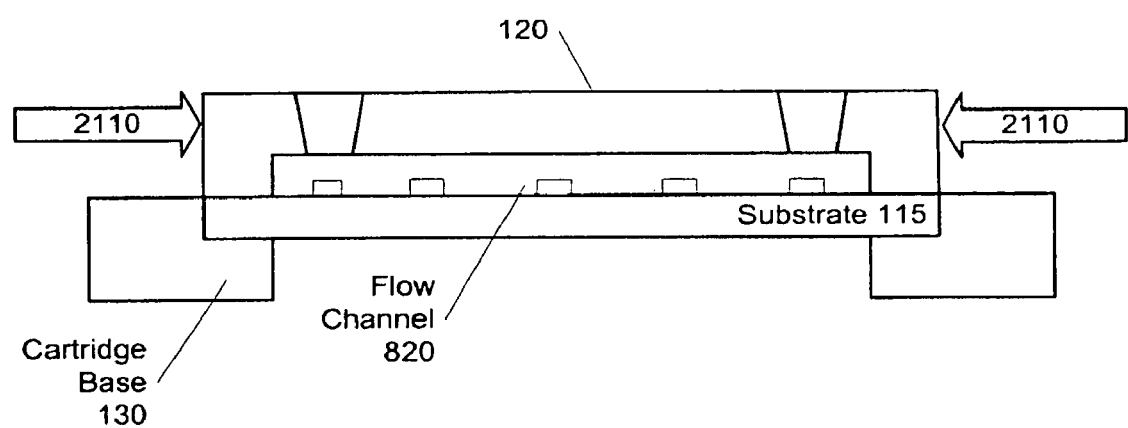
FIG. 21 is a schematic cross-sectional view of the substrate assembly, showing another way of sealing inlet ports and outlet ports of a reaction containment member using a force to squeeze the wells shut.

FIG. 21 shows an alternate way of sealing the ports, where a horizontal force 2110 is applied to the sides of the reaction containment member 120 to squeeze the inlet ports 810 and/or outlet ports 815 shut. If this sealing method is used, then the reaction containment member 120 is manufactured of a material that is sufficiently soft to allow the wells to be squeezed shut through the application of the force 2110.

Figure 22:
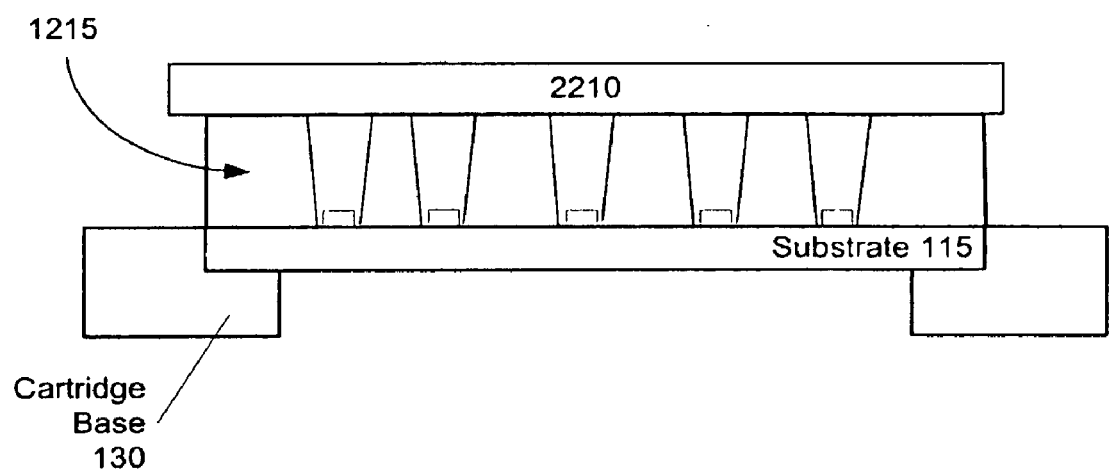
FIG. 22 is a schematic cross-sectional view of the substrate assembly, showing another way of sealing inlet ports and outlet ports of a reaction containment member using a plate to cover the well openings.

FIG. 22 shows yet another way of sealing the wells 1217 in the reaction containment member 1215, wherein a flat surface 2210 is positioned over the reaction containment member 120. The flat surface covers the upper openings of the wells to thereby seal the openings of the wells shut. In one embodiment, the flat surface can be a plastic. The plastic can be heated to avoid condensation.

I. Thermal Cycler

Figure 23:
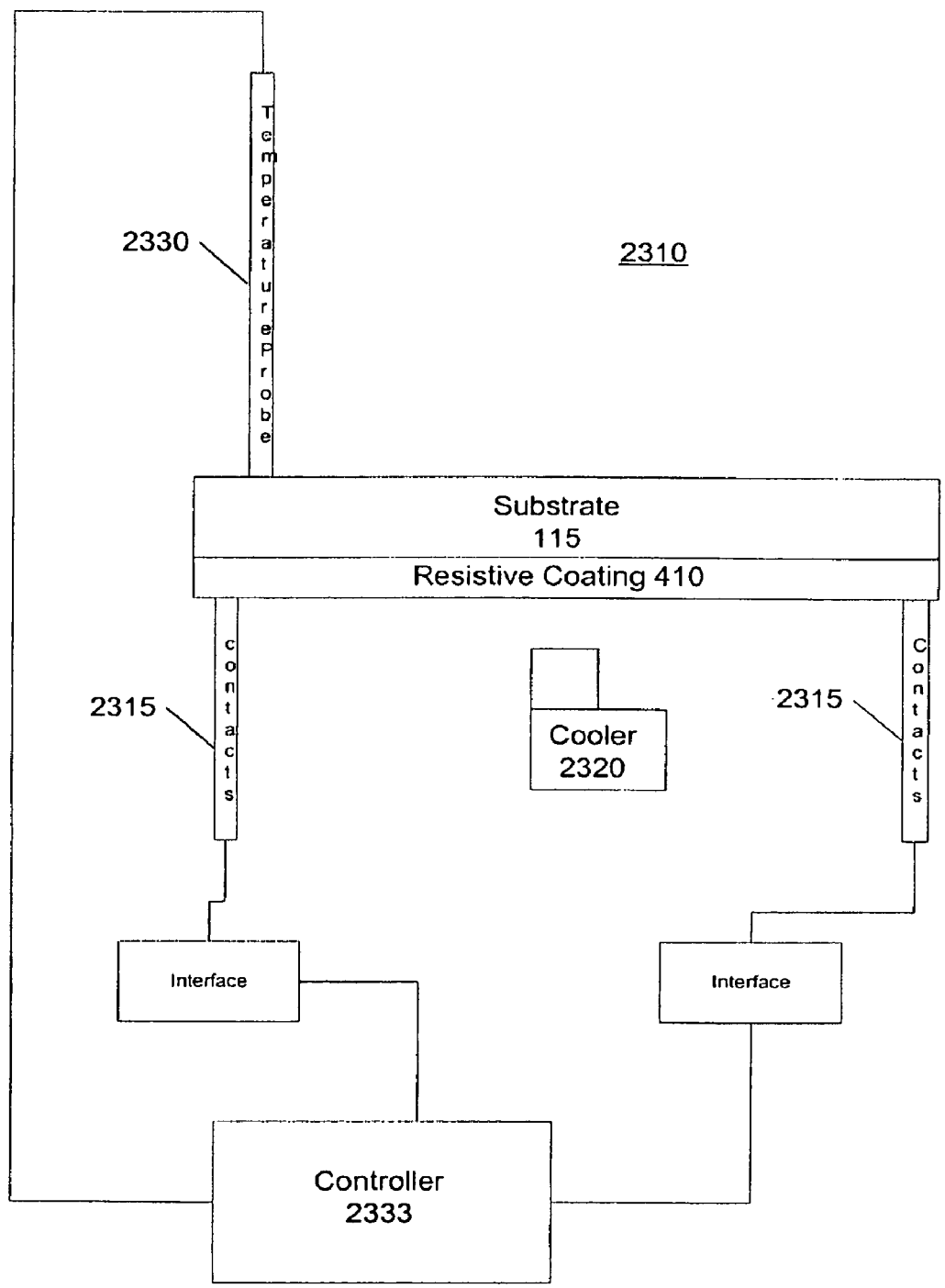
FIG. 23 shows a schematic view of a thermal cycler that is used to thermally cycle a substrate, such as during a PCR process.

FIG. 23 shows a schematic view of a thermal cycler 2310 that enables the substrate to be thermally cycled, such as during a PCR process. The thermal cycler is built into the machine 1910 shown in FIG. 19, such as at a working location of the surface 1915, as described more fully below. The substrate 115 is positioned on a support surface of the thermal cycler 2310, with the substrate 115 being disposed within the substrate assembly 110, although FIG. 23 does not show the cartridge base 130, cartridge cover 135 and reaction containment member 120. The thermal cycler 2310 includes one or more heating contacts 2315 that are used to heat the substrate 115, and can also include a cooling system 2320 that is used to cool the substrate, as wells as a temperature probe 2330 that is used to measure the temperature of the substrate 115. A controller 2333 is used to control the thermal cycler 2310.

The heating contacts 2315 may comprise electrically-conducting rods, such as elongate metal rods. A portion of the heating contact 2315, such as an upper tip of the heating contact 2315, touches the resistive coating 410 on the substrate. An electrical current is applied to the resistive coating via the heating contacts 2315, which cause the resistive coating to generate heat to thereby cause the substrate 115 to also heat by virtue of the thermal connection between the substrate 115 and the resistive coating 410. The heating contacts 2315 produce a uniform sheet of current through the resistive coating 410. It has been determined that more contact area between the heating contacts 2315 and the resistive coating results in more heat uniformity over the resistive coating 410. However, this also results in a higher heat flow between the substrate and the electrical contacts, which is undesirable because the contacts may thereby effect the temperature of the substrate 115. Thus, there is generally a balance between the amount of contact area between the heating contacts 2315 and the substrate 115 and the amount of heat flow between the heating contacts 2315 and the substrate 115.

Figure 19:
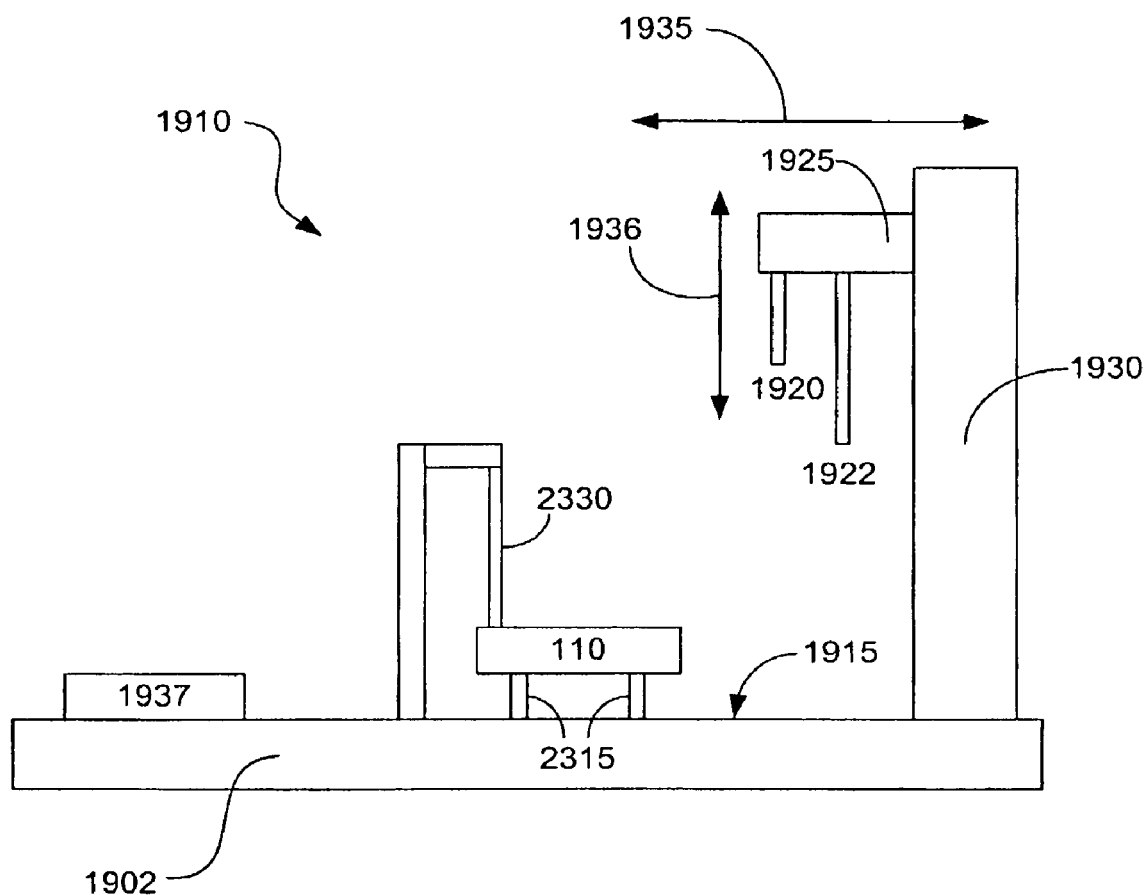
FIG. 19 shows a substrate processing machine that is used to processes biological samples using the substrate assembly of FIG. 1.
Figure 24:
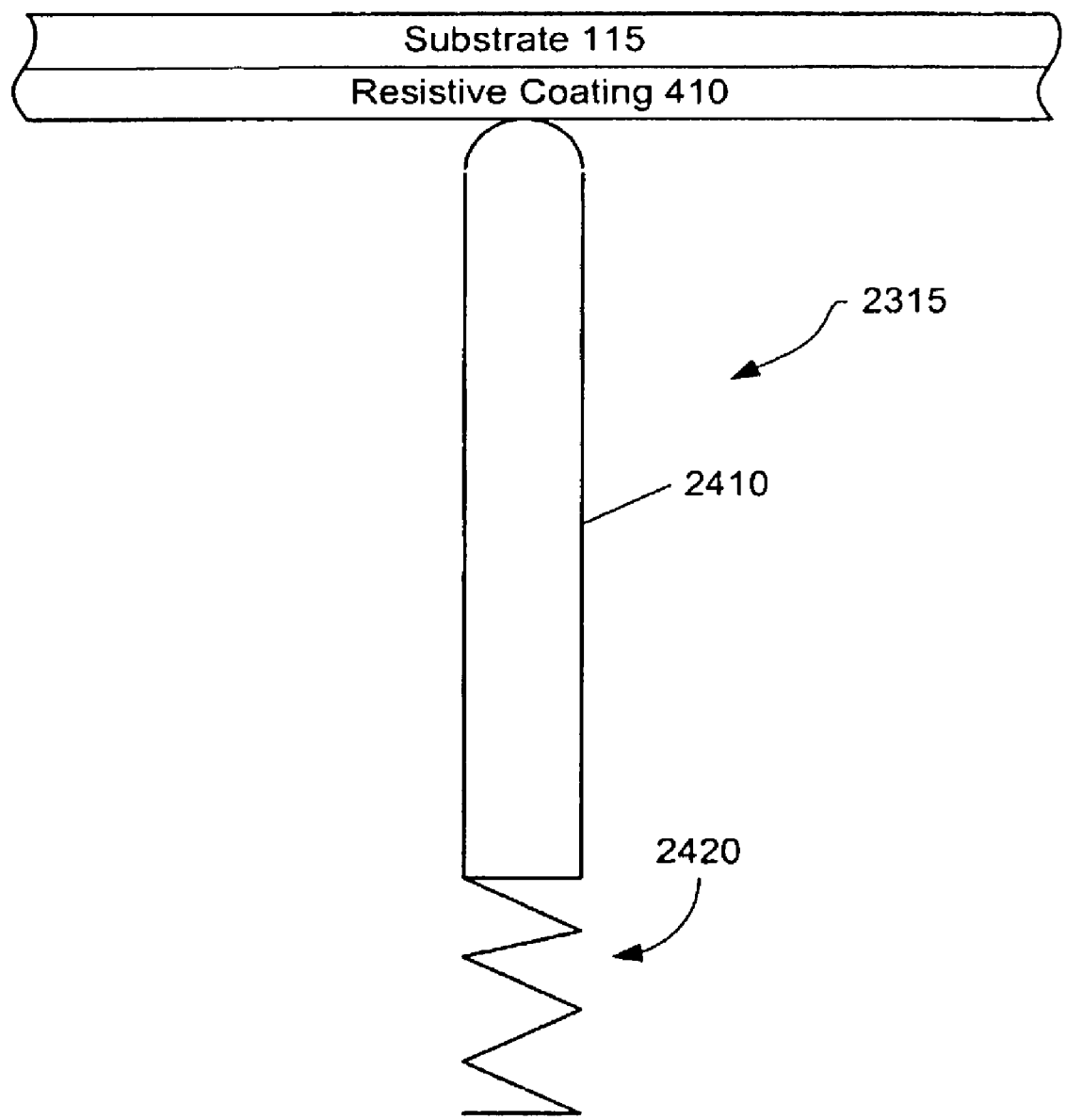
FIG. 24 is a schematic view of an electrical contact that is used to heat the substrate, the electrical contact comprising a pogo pin having an upper tip that contacts the substrate.

In one embodiment of the heating contacts 2315, shown in FIG. 24, each heating contact comprises a pogo pin 2410 that is mounted on a spring 2420. The relative sizes of the substrate 115 and pogo pin 2410 are exaggerated in FIG. 24 for clarity of illustration. The spring 2420 provides a load on the pogo pin 2410 so that an upper tip of the pin 2410 presses against the resistive coating 410 on the bottom surface of the substrate 115 when the substrate 115 is located on top of the pogo pin 2410. The heating contacts 2315 comprised of the springs 2420 and the pogo pins 2410 may be positioned on the surface 1915 of the machine 1910, as shown in FIG. 19.

In one embodiment, two heating contacts 2315 are positioned along opposed edges of the substrate and spaced at approximately ⅓ intervals along the length of the substrate 115. It should be appreciated that other spacing and positioning arrangements for the heating contacts 2315 may also be used. The heating contacts 2315 generally have a ball-nose shaped tip that contacts the substrate 115 to minimize contact area but still provide a reliable connection between the heating contact 2315 and the substrate 115. As mentioned, minimizing the contact area minimizes heat flow between the pin and the substrate 115 so that the pin has little or no impact on the temperature of the substrate 115.

Figure 25A:
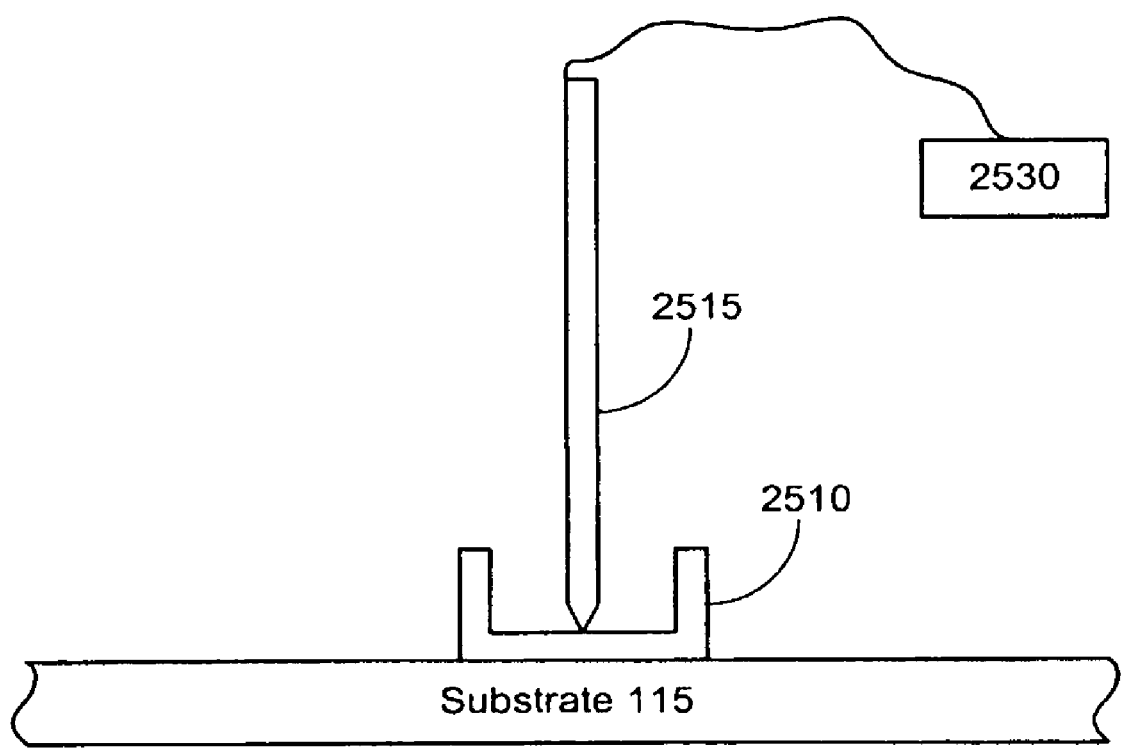
FIG. 25A shows a first embodiment of a temperature probe of the thermal cycler of FIG. 23, wherein the temperature probe measures the temperature of a substrate.

As shown in FIG. 23, the temperature probe 2330 contacts the substrate 115 to thereby measure the temperature of the substrate. The temperature probe 2330 is generally configured to provide very low heat transfer between the probe tip and the substrate so that the probe 2330 does not affect the temperature of the substrate 115. In this regard, the temperature probe 2330 generally has a low thermal mass. FIG. 25A shows a first embodiment of the temperature probe 2330 that includes a thermistor as a temperature sensing element. The thermistor is embedded into a small metal contact element 2510 that has a flat surface that contacts the substrate 115. The contact element 2510 is made of a metal, such as aluminum or brass. The contact element 2510 is held in place by a needle 2515 in such a way that the contact element 2510 can pivot and maintain contact between the flat surface of the contact element 2510 and the substrate 115. The contact element 2510 measures the temperature of the substrate 115 through the embedded thermistor and passes a signal indicative of the temperature through a wire attached to or embedded in the needle 2515 in a well-known manner. A temperature reader 2530 monitors and records the temperature in a well-known manner.

Figure 25B:
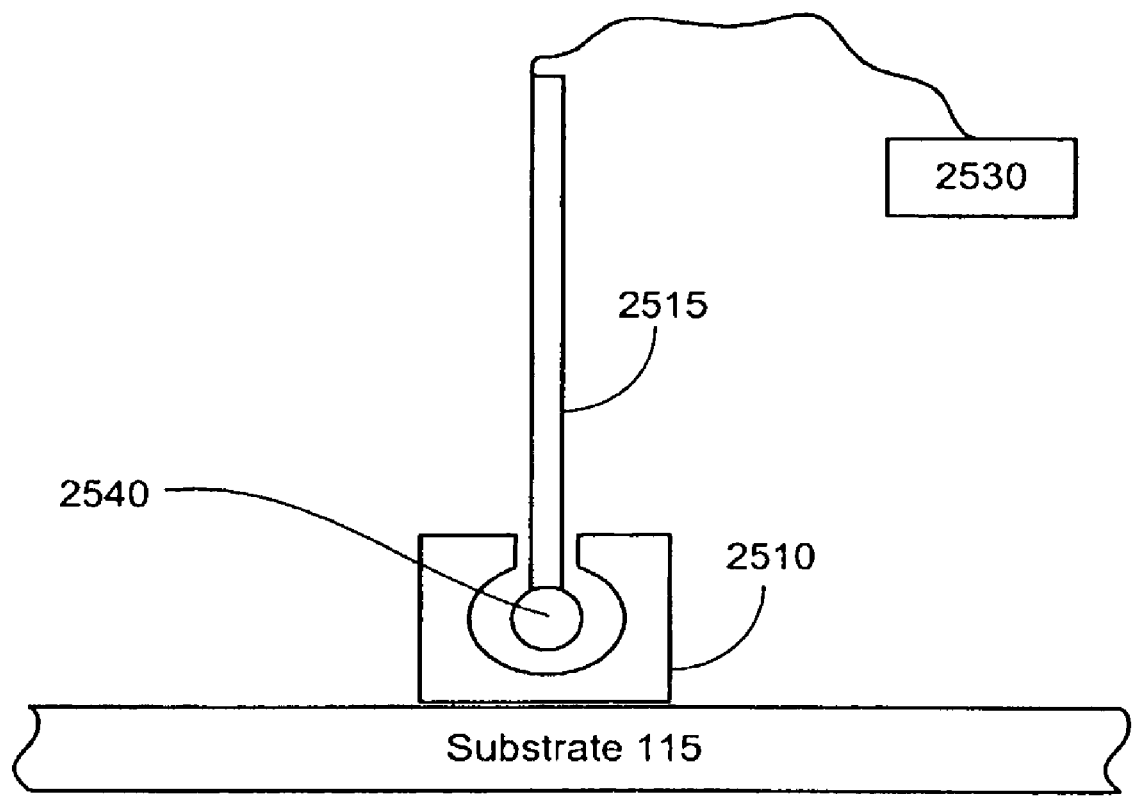
FIG. 25B shows a second embodiment of a temperature probe of the thermal cycler of FIG. 23.

In another embodiment of the temperature probe, shown in FIG. 25B, the tip of the needle 2515 attaches to a ball 2540 that is positioned within a rounded cavity in the contact element 2510. The ball interacts with the rounded cavity in a manner that allows the contact element 2510 to pivotably maintain contact with the substrate 115. In yet another embodiment, the temperature of the substrate 115 is measured by using a temperature sensor that is integrated onto the substrate. As mentioned, it is desirable to minimize the thermal contribution that the environment provides to the substrate 115 during thermal cycling. In this regard, certain portions of the temperature probe 2330 may be heated to a temperature that reduces the likelihood of the probe transferring heat or drawing heat to or from the substrate 115 as a result of the contact. For example, the needle 2515 may be heated so as to minimize any heat exchange between the needle 2515 and the substrate so that the needle 2515 has little or no effect on the temperature of the substrate 115. The needle 2515 can be heated to the same temperature as the substrate so that there is no heat exchange between the needle 2515 and the substrate. In this manner, the temperature of the contact element will accurately reflect the temperature of the substrate 115.

With reference again to FIG. 19, the temperature probe 2330 is generally mounted on the surface 1915 of the machine 1910, such as using some type of support structure that extends upwardly from the surface 1915. The support structure can support the temperature probe 2330 in an elevated position over the substrate assembly 110 such that the probe can measure the temperature of the substrate 115.

With reference again to FIG. 23, the cooling system 2320 functions to cool the substrate when required by the desired temperature cycle. The cooling system 2320 removes heat from the substrate 115. In one embodiment, the cooling system 2320 comprises a fan that blows air over the substrate for cooling. The fan can be turned off during heating. Alternately, the fan may be left on at all times and the heater power adjusted to vary heating. There are also other ways of cooling the substrate 115, including (1) spraying a mist of fluid, such as, for example, water or alcohol, on the bottom side of the substrate; (2) placing a cold block in contact with the substrate to absorb heat from the substrate; (3) blowing compressed air over the substrate using a nozzle (rather than using a fan); (4) using a compressed air vortex cooler. The cooling system 2320 can be mounted on the machine 1910, such as below the surface 1915 and be provided access to the substrate assembly 110 through a hole in the surface 1915.

The various components of the thermal cycler 2310 may require access to the top or bottom surfaces of the substrate. For example, the temperature probe 2330, the heating contacts 2315, and the cooling system 2320 may have components that require contact with the surfaces of the substrate. Advantageously, the substrate assembly 110 provides access to the substrate surfaces even when the substrate 115 is mounted in the cartridge. The cartridge base 130 has an aperture 510 (shown in FIG. 5) that allows access to the bottom surface of the substrate 115 when the substrate is mounted in the cartridge. Likewise, the cartridge cover 135 has an aperture 710 (shown in FIG. 2) that provides access to the top surface of the substrate 115. The apertures 510 and 710 thus provide access ta the substrate surfaces for the electrical contacts, temperature probes, and cooling system, even when the substrate 115 is contained within the cartridge.

Figure 26:
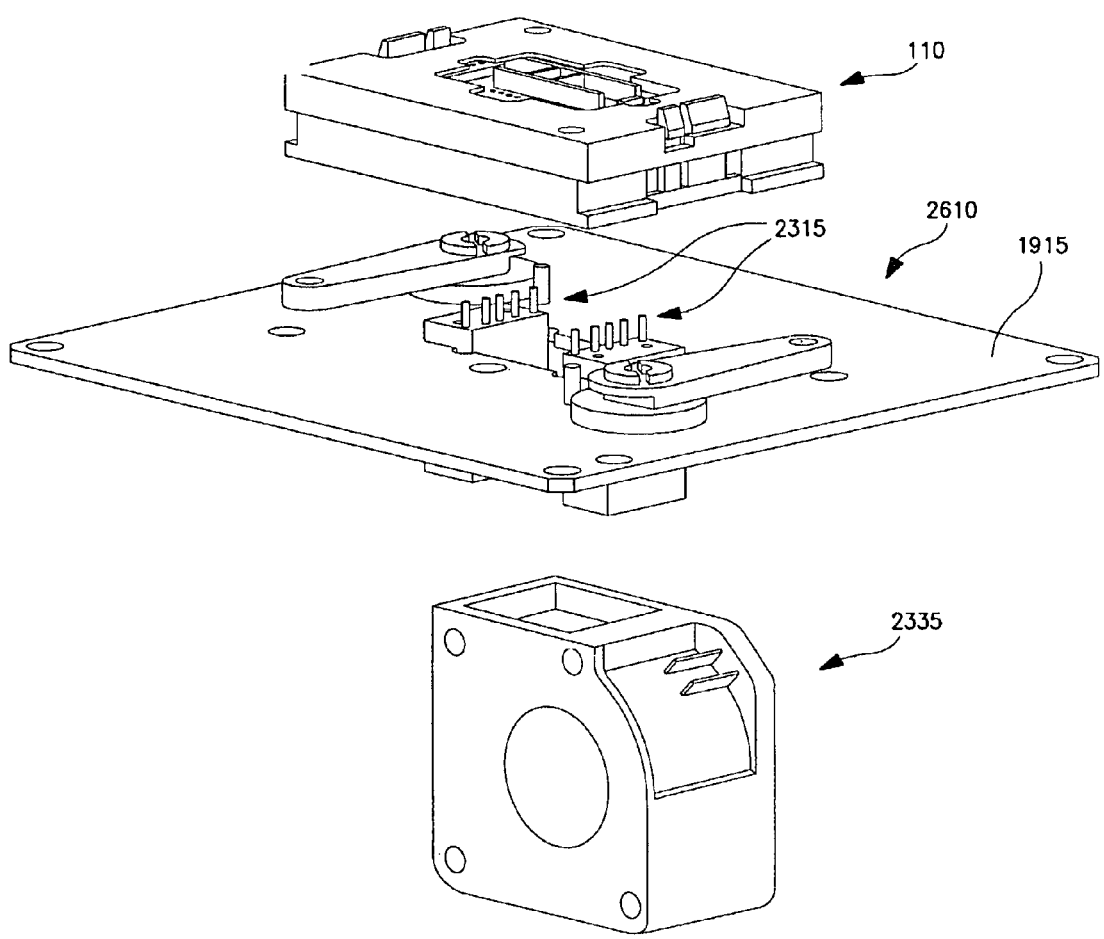
FIG. 26 shows a perspective view of the various components of the thermal cycler.

FIG. 26 shows a perspective view of the various components of the thermal cycler 2310. A work station 2610 comprises a flat surface on which the substrate assembly 110 can be mounted. The work station is incorporated into the surface 1915 of the machine 1910 (shown in FIG. 19) such that the work station 2610 of the thermal cycler 2310 is also the work station of the machine 1910. The flat surface of the work station 2610 may be integrally formed with the surface 1915 of the machine 1910 or it may be a separate surface. The substrate assembly 110 can located on the surface 1915 of the machine 1910 so that thermal cycling can be performed, while also allowing material dispensing through the micro- and nanodispensers 1920, 1922 while the substrate assembly 110 remains in a stationary location. The work region 2610 includes the contacts 2315, which are upwardly-disposed on the work region so that they can contact the substrate assembly 110. The cooling system 2320 shown in FIG. 26 comprises a fan 2335 that blows air in an upward direction toward the substrate in the substrate assembly 110. As mentioned, the cooling system 2320 can be mounted in the machine 1910.

Figure 27:
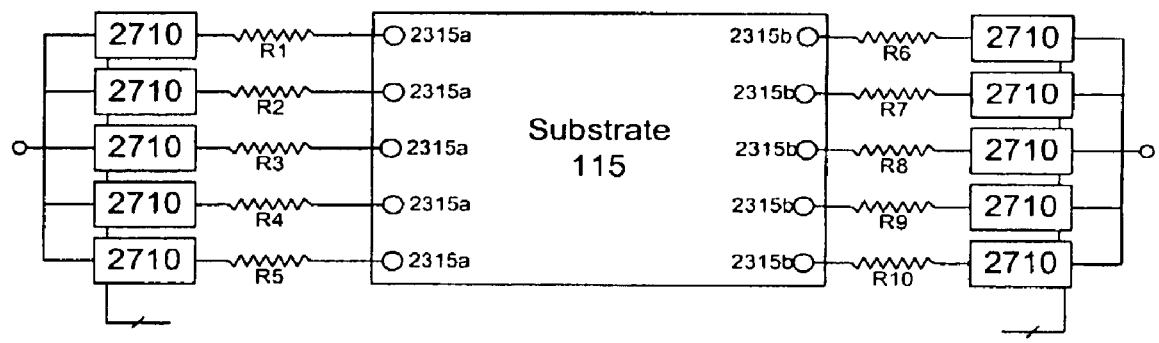
FIG. 27 is a schematic view of an electrical contact interface of the thermal cycler.

As mentioned, the thermal cycler 2310 provides a uniform heat distribution across the surface of the substrate 115. FIG. 27 shows a schematic view of an electrical contact interface that provides the ability to "shape" the electrical current through each contact 2315 and thereby provide a uniform heat pattern across the entire surface of the substrate 115. A first set of contacts 2315a are located along an edge of the substrate 115 and a second set of contacts 2315b are located along an opposed edge of the substrate 115. A resistor R is placed in series with at least one of the contacts 2315a, 2315b and, in one embodiment, in series with all of the contacts 2315a, 2315b. An electrical current sensor 2710 is also placed in series with each contact 2315 for sensing and monitoring the electrical current to each contact 2315 in a well-known manner. The electrical current sensor 2710 can be used to feedback a measured current to a controller for adjustment of the current.

A current is then applied to the first set of contacts 2315a so that the current flows through the resistive coating from the first edge of the substrate 115 to the second set of contacts 2315b at the opposed edge. Those skilled in the art will appreciate that the net current at the first set of contacts 2315a will be equal to the net current at the second set of contacts 2315b. The resistance value of one or more of the resistors R can be varied relative to the other resistors R, while maintaining a constant voltage, to thereby adjust the current that flows through each the individual electrical contacts 2315a, 2315b. For example, the resistor R1 may have a higher resistance relative to the resistor R10 while maintaining the same voltage between the two. This would result in a lower electrical current to the contact 2315 attached to the resistor R1. Thus, the relative current through the contacts 2315 can be adjusted by adjusting the level of resistance in one contact relative to another contact. That is, the current through each contact 2315 can be increased or reduced relative to the other contacts to thereby adjust the temperature profile across the surface of the substrate 115. Although the temperature profile may also be adjusted by patterning the resistive heating coating on the substrate 115, the setup shown in FIG. 27 can be used to avoid the difficulty and expense that can be associated with patterning the resistive coating. FIG. 27 shows five contacts 2315 located along opposed sides of the substrate 115. However, it should be appreciated that the quantity and location of the contacts 2315 can be varied to provide other heating profiles.

The substrate assembly 110 and the processing machine 1910 can be used to deposit samples of biological materials on the substrate 115 and to perform a wide variety of processes and analyses on the materials. For example, the substrate assembly can be used to perform single nucleotide polymorphism (SNP) detection process or any of a wide variety of biochemical processes on biological samples contained in the target locations. In a first step of such a process, one or more samples of biological material, such as a captured oligo, are collected in a well-known manner and then deposited on the substrate 115 to form a plurality of target locations. The substrate 115 is then mounted in the cartridge to form the substrate assembly.

Figure 28:
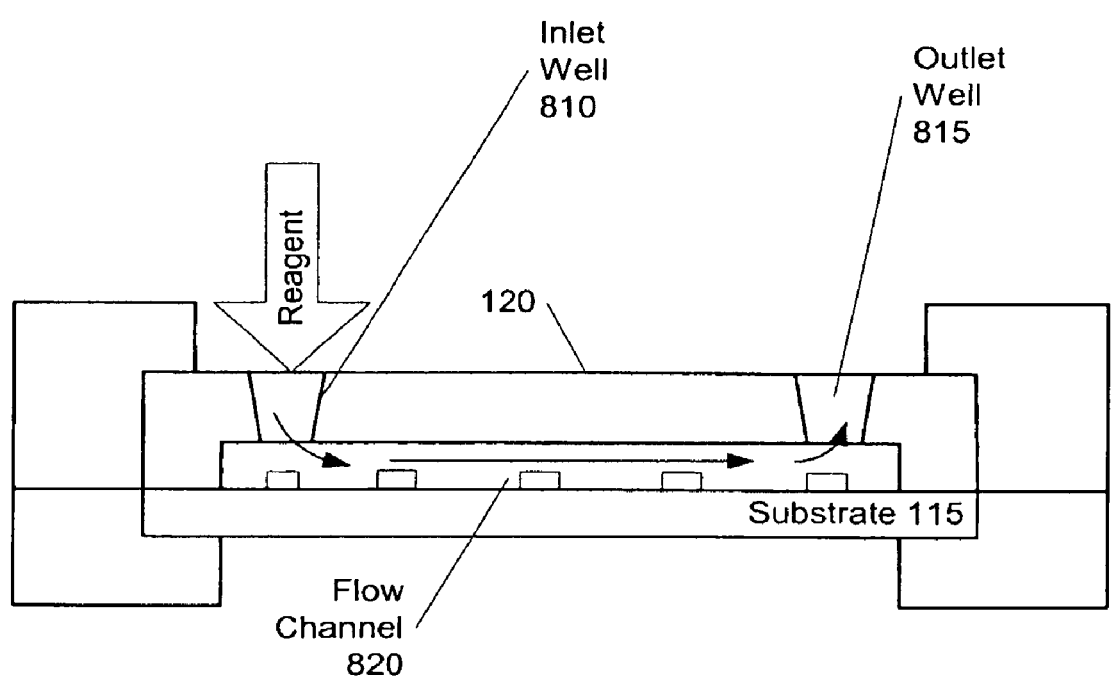
FIG. 28 shows a reagent being deposited into an inlet port of the substrate assembly for exposing target locations on a substrate to the reagent.
Figure 29:
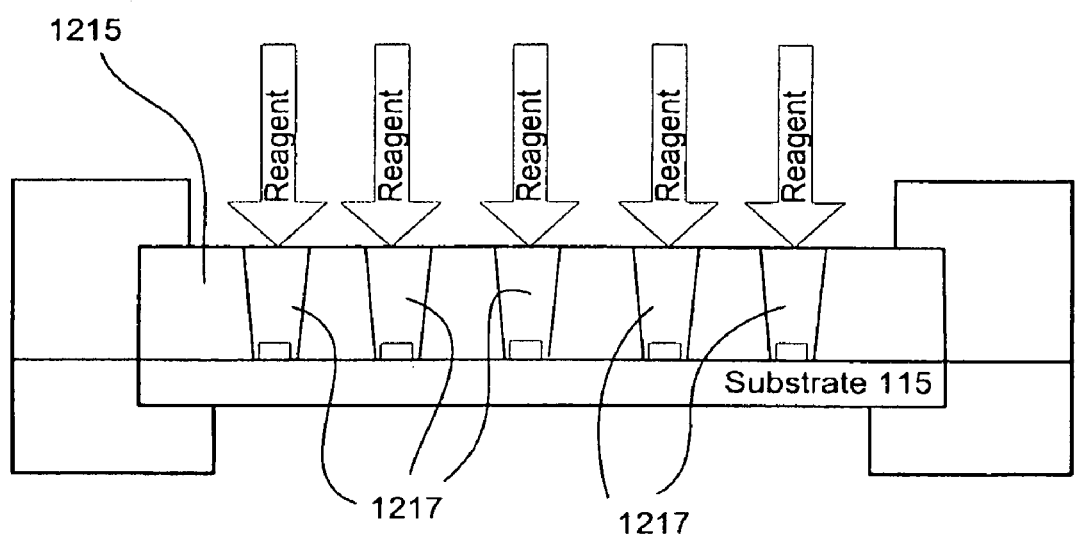
FIG. 29 shows a reagent being deposited into a plurality of inlet ports of the substrate assembly for exposing target locations on a substrate to the reagent.

The target locations can then be exposed to any of a wide variety of materials by dispensing the materials into the chambers that are formed over the substrate 115 by the reaction containment member 120. Advantageously, the machine 1910 shown in FIG. 19 can be used to dispense the materials into the chambers. If the reaction containment member 120 is used, then the dispenser 1920 or 1922 injects a material, such as a reagent, into the inlet ports 810, such as is shown in FIG. 28. The reagent flows down through the inlet ports 810 and flows through chamber formed by the flow channel 820, as exhibited by the arrows in FIG. 28. The reagent is thereby exposed to all of the target locations that are located within the channel. The reagent can flow out of the channel 820 through the exit wells 815. Alternately, each target locations can be individually exposed to a material using the reaction containment member 1215. In such a case, a dispenser would include an array of dispensing pins with one dispensing pin for each well 1217 in the reaction chamber, such as is shown in FIG. 29. It should be appreciated that materials other than reagents can also be exposed to the target locations using the inlet ports and outlet ports.

Thermal cycling of the material contained within the chambers can be performed using the temperature cycling device 2310 shown in FIG. 23 without having to remove the substrate 115 from the cartridge and while the substrate remains in the same location on the machine 1910. An electrical current is applied to the substrate 115 to thereby heat the substrate 115 according to a desired temperature cycle. The substrate 115 is cooled using the cooling system 2320 of the thermal cycler. The substrate 115 can then be removed from the cartridge by removing the cartridge cover 135 from the cartridge base 130. The substrate 115 may then be subject to MALDI-MS by moving the substrate 115 to an appropriate device as will be known to those skilled in the art.

D. Methods For Performing And Analyzing Reactions

Provided herein are methods for both performing one or more reactions involving a biomolecule and analyzing one or more resulting reaction products on a surface of a substrate. In particular embodiments of the methods, at least two or more reactions are performed. In other embodiments, at least three or more reactions are performed. In one embodiment, if only one reaction is performed, the reaction is not a hybridization reaction. In a particular embodiment, the reaction(s) are performed substantially in solution. A reaction performed substantially in solution is one in which the interactions between the majority of the reactants occur in solution such that the majority of the reactants and any intermediates are in solution. In a particular embodiment, the reaction product(s) is (are) captured on the surface of the substrate.

In one embodiment of the methods, the reaction(s) and at least the initiation of a detection process are each conducted in the presence of the same single target detection location. In another embodiment of the methods, the reaction(s) and at least the initiation of a detection process are each conducted in the presence of the same two or more target detection locations. In a particular example, a target biomolecule, e.g., a nucleic acid, is applied to a substrate at a discrete location with a targetcapture moiety thereon, referred to as the target detection location. In the presence of the target detection location, one or more reactions involving the target molecule are performed and the resulting product is immobilized through a solid-phase. Upon capture of the reaction product(s) at the target detection location, the analysis or detection of the reaction product(s) proceeds at the target detection location. For example, when analyzed by MALDI mass spectrometry, the captured reaction product may be contacted with a matrix material to facilitate MALDI-MS and is exposed to a laser to initiate ionization of the reaction product(s) at the target detection location. The target detection location may be contained within a chamber or channel.

A particular advantage of the methods provided herein, is the detection of the captured target biomolecules at the same location, in which the pre-capture solution phase reactions were performed. Thus, the location of the pre-capture solution phase reactions and the target detection location are the same. This particular feature reduces the cost and time, as well as the amount and the complexity of the machinery required to automatically carry out the reactions in a high throughput format. This feature is accomplished by removing the reaction containment member, which creates one or more reaction chambers or channels in which the solution-phase reactions occur, from the substrate after the target capture step on the target detection locations. Thus, the methods provided herein do not require the physical transfer of solution-phase reaction products to a new target detection location and/or a new solution having capture moiety therein prior to the capture of the target biomolecules. For example, when the substrate is a chip, the chip can advantageously remain stationary throughout the solution phase reactions, at least until reaction product(s) are captured. Once the reaction product(s) are captured, the chip can be moved and/or prepared for detection analysis, such as with MALDI-TOF mass spectrometry.

The methods can be used in a variety of applications in which the analysis of a biomolecule is conducted in order to obtain information about the identity, structural and/or functional properties of a biomolecule or about the presence or absence of a particular biomolecule in a sample. Such applications include diagnostic, screening, discovery and detection methods of importance in the biological, biomedical and pharmaceutical sciences. For example, accurate determination of a particular polymorphism or mutation on a nucleic acid or protein level is often used in the diagnosis of a genetic disorder. Detection of binding of a molecule, such as a peptide or small organic molecule, to a receptor or other cellular component and/or the functional consequences thereof is often used in methods of screening for therapeutic agents for treatment of diseases. Detection of characteristic elements of pathogenic agents, e.g., bacteria and viruses, is often used in the diagnosis of infectious diseases. Determination of the sequence of a biopolymer, e.g., nucleic acids and proteins, or the identity of a polymorphic nucleotide, is often used in diagnostic, genotyping and polymorphism identification methods.

In particular embodiments of the methods provided herein for performing and analyzing reactions involving a biomolecule, the reaction(s) are performed substantially in solution. Solution phase reactions avoid disadvantages, restrictions and limitations imposed when reactions are conducted on a solid support. For example, solution phase reactions occur in three-dimensions while reactions conducted on a solid support are restricted to two dimensions and can be significantly affected by steric hindrance, lack of inadequate mixing or adsorption of reactants. In addition, some reactions, for example, those that require the recognition of a particular molecular shape, conformation or active site, may be suppressed if conducted on a solid support because molecules immobilized on a surface may have a different geometry or conformation than when they are in solution phase. These restrictions are especially of great influence on highly functional macromolecules, like enzymes and proteins, which are essential for reactions used herein or can be target biomolecules for analysis.

In particular methods provided herein for performing and analyzing reactions involving a biomolecule, a product of a reaction is captured on a substrate, which, for example, can be in a chamber, in which a reaction is performed, thereby retaining it for analysis or detection in a defined location, e.g., a target detection location. Typically, the reaction product(s) is (are) captured at the interior bottom of a chamber, which may be, for example, a substrate capable of specifically interacting with the reaction(s) product in such a way as to retain it attached to the substrate during processes used to remove or wash other molecules from the chamber. The capturing of a product to be analyzed in the methods provides several advantages. For example, the reaction(s) performed on biomolecules on a substrate, e.g., in a chamber, can be conducted in solution and any post-reaction processing and pre-analysis preparation of a reaction product can be conducted without the restrictions that may be imposed when reactions are performed on biomolecules that are immobilized to a solid support. Furthermore, capture of a reaction product to be analyzed facilitates isolation and purification of the product prior to analysis thereby reducing or eliminating reagents, chemicals and other molecules and contaminants that can obscure the analysis. In addition, the captured reaction product(s) is localized to a specific region of a substrate that may also have attached to it products of other reactions which are immobilized at different regions. Thus, multiple different reactions may be conducted in separate or a single chamber but analyzed separately by virtue of the distinct locations of the reaction products on the substrate.

The methods provided herein can be conducted on a substrate surface, e.g., in a single chamber, at low volumes thereby reducing the amount of reagents, the transfer of reagents and products and the process time required for performing and analyzing biomolecules. The methods are well suited to miniaturization. The methods can be performed in multi-chamber formats for parallel processing of numerous reactions and can also be performed such that multiple different biomolecules are reacted and analyzed within a single chamber. The methods provided herein are thus particularly well suited for rapid, sensitive and accurate analysis of large numbers of different biomolecules as may be done, for example, in high-throughput screening processes.

As set forth herein in particular embodiments, two or more equivalent reactions occur in parallel at two or more respective discrete locations on the substrate (e.g., chip). The total number of reaction chambers or channels used to conduct the reaction(s) within a reaction containment member on a substrate can be as many as desired, depending on the size of the substrate and/or the constraints of the molding of the reaction containment member. In one embodiment, within a single reaction containment member, up to 5,000 or more reaction chambers are contemplated for use herein. For example, the number of reaction chambers or channels within a reaction containment member can range from 1, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000 up to 5000 or more.

Likewise, the total number of target detection locations (loci) on a substrate and/or within a particular reaction chamber or channel can be as many discrete target detection loci as desired, so long as it is ensured that a sufficient sample size is present to achieve the desired chemical reaction. In one embodiment, each single reaction chamber within the reaction containment member can contain up to 5,000 or more discrete target detection loci on a substrate. For example, 1, 2, 3, 4, 5, 6, 7, 8, 10, 15, 20, 25, 30, 40, 50, 60, 70, 80, 90, 96, 100, 200, 300, 384, 400, 500, 600, 700, 800, 900, 1000, 1500, 1536, 2000, 3000, 4000 up to 5000 or more discrete target detection locations can be confined on a substrate within one or more reaction chambers or channels.

As set forth in one embodiment herein, the reactions occur in a solution in the presence of a substrate surface having the capture-biomolecules thereon. In one embodiment, the reactions (e.g., PCR and/or primer extension) occur over a substrate surface having the capture-biomolecules thereon that is also surrounded by a chamber or channel of a reaction containment member that confines the reactions to the presence of a single target detection location throughout the process (FIGS. 12A and 13). For example, in one embodiment utilizing a 96-target loci chip having 12 rows of 8 target detection locations, 96 discrete solution phase reaction mixtures are used, e.g., in parallel, such that each reaction mixture in solution is confined by the substrate surface having the corresponding 96 discrete target locations with capture-biomolecules thereon (see FIG. 12A and FIG. 13). The surrounding walls of the chamber can be any shape, such as circular, square, rectangular, etc., e.g., to form channels, chambers or simulate wells of a microtiter plate.

In another embodiment, the one or more reactions occur over a substrate surface having the capture-biomolecules thereon that is also surrounded by a chamber or channel of a reaction containment member that confines the reactions to the presence of two or more target detection locations throughout the process. In a particular embodiment, the reaction(s) are confined to only a subset of the total target detection locations contained on the entire substrate surface (chip). For example, in one embodiment utilizing a 96-target detection loci chip having 12 rows of 8 target detection locations, 12 discrete solution phase reaction mixtures are used in parallel such that each reaction mixture in solution is confined by the substrate surface having 8 discrete target detection locations with capture-biomolecules thereon (see FIG. 12B). In this embodiment, the 12 discrete solution phase reaction mixtures are confined by channels within the reaction containment member that separate each reaction mixture. In other embodiments, 20 reaction chambers or channels within a reaction containment member are contemplated herein overlayed on a substrate having 10, 20, 30, 40, 50, 60, 70, 80, 90, 100 or more discrete target detection locations within each reaction channel or chamber.

J. Thermocycling

One of the advantages of using the methods and apparatus provided herein is the fast thermocycling capability. Previously available thermocyclers include a large thermal block to the heat the standard microtiter plate. In these prior systems, due to the large thermal mass of the block, thermal ramping (e.g., the rate of heating the block or system) is on the order of 1-2° C./second. In addition, because the reagent volume is relatively large (e.g., 5-25 µl) the temperature ramping of the fluid, as well as the cooling rate, is further decreased. Another disadvantage with these previous systems, indicated by computer simulations, is that uneven sample temperature distribution, on the order of several degrees, will be present although the temperature distribution of the metal heater block itself is uniform. These disadvantages are compounded with technical difficulties related to the tolerance of the microtiter plates themselves. For example, due to the variations in manufacturers' design of a microtiter plate, a firm direct contact of the microtiter well to the thermal block is not always achieved. During the use of standard microtiter plates, air gaps are present between the wells and the thermal block walls, causing further uneven heating and temperature distribution. Furthermore, although heating rates may be increased with the use of more power, cooling is often more difficult due to high thermal mass of the heater block.

The methods and apparatus provided herein advantageously avoid the use of a large thermal mass and the use of a secondary platform to heat the sample volumes. In addition, rather than using a vessel that sits in a thermal block for thermocycling, the methods and apparatus provided herein use the reaction vessel (i.e., substrate) itself to thermocycle. As set forth herein, the substrate (e.g., a chip) behaves as the thermocycler itself. For example, in one embodiment, individual wells are created by a silicon gasket (i.e., reaction containment member) in a format that is compatible with, for example, standard 96, 384, or more, well formats (see, e.g., FIG. 11).

The integration of the thermocycling function within the substrate in the methods and apparatus provided herein eliminates the air gaps found with conventional thermocycler heater blocks. In particular embodiments of the methods and apparatus provided herein, because the substrate (for example, a silicon chip) as well as the sample amount are several orders of magnitude smaller than conventional sample volumes in a microtiter plate, faster heating (e.g., ramp rate) and cooling of the reaction mixtures is achieved.

In a particular embodiment in which the target biomolecule is nucleic acid and one of the reactions is a nucleic acid amplification reaction and/or a primer extension reaction, the methods provided herein advantageously utilize a fast thermocycling chip prepared as described herein (see, e.g., FIGS. 1-29), wherein the chip containing the removable reaction-containment-member undergoes fast thermocycling temperature changes to facilitate the amplification reaction(s). Fast thermocycling is achieved by heating and cooling the chip directly. The time required for cooling and heating is the main contributing factor with respect to the duration of thermocycled reactions. By increasing the rate of cooling and heating, the methods provided herein advantageously shorten the total processing times for such reactions.

In one embodiment, direct heating can be mediated by running an adjustable current through a resistive coating (e.g., a thin metal layer; see FIG. 4) on the backside of the chip. Heating is achieved through electrical pin contacts to a deposited metal on the backside of a substrate (e.g., a silicon chip). Multiple contacts are made at various points on the substrate for optimized temperature uniformity. To increase the rate of heating (e.g., the ramp rate) more power can readily be applied to the metallized substrate.

In particular embodiments, a heating ramp rate in the range of about 3° C./second up to about 100° C./second can be used, versus heat ramp rates of conventional thermocyclers that utilize about 1-2° C./sec. In one embodiment, a heating ramp rate of at least about 3, 4, 5, 6, 7, 8, or 9° C./second is used. In another embodiment, a heating ramp rate of at least about 10° C./second is used. In another embodiment, a heating ramp rate of at least about 15° C./second is used. In another embodiment, a heating ramp rate of at least about 20° C./second is used. In another embodiment, a heating ramp rate of at least about 25° C./second is used. In another embodiment, a heating ramp rate of at least about 30° C./second is used. In another embodiment, a heating ramp rate of at least about 35° C./second is used. In another embodiment, a heating ramp rate of at least about 40° C./second is used. In another embodiment, a heating ramp rate of at least about 45° C./second is used. In another embodiment, a heating ramp rate of at least about 50° C./second is used. In other embodiments, rates of heating of at least about 60, 70, 80, 90 up to 100° C./second or more can be used. Accordingly, in the methods provided herein, the rate of heating can be selected from the group consisting of rates of heating of at least about: 3, 4, 5, 6, 7, 8, 9, 10, 15, 20, 25, 30, 35, 40, 45, 50, 60, 65, 70, 75, 80, 85, 90, 95 and at least about 100° C./second.

Another advantage achieved by the methods and apparatus provided herein are the increased rates achieved for cooling the thermocycler. In one embodiment, active cooling of the nanosubstrate (e.g., nanochip) can be achieved using a cooling fan by exposing the underside of the substrate to forced air convection. In other embodiments to achieve higher cooling rates a water-based cooling technique can be employed for a nanotiter substrate design. In this embodiment, at each cycle interval, a water jet spray uniformly cools the backside of the substrate (e.g., a silicon chip). In another embodiment, a cooling block that is kept at a constant cold temperature can be employed that is periodically and reversibly contacted with the backside of the substrate during the cooling phase of the amplification reaction. Cooling rates in the range of about 3° C./second up to about 100° C./second can be used with the thermocycling substrates provided herein, compared to cooling rates of 1-2° C./sec for conventional thermocyclers. In one embodiment, a cooling rate of at least about 3, 4, 5, 6, 7, 8, or 9° C./second is used. In another embodiment, a cooling rate of at least about 10° C./second is used. In another embodiment, a cooling rate of at least about 15° C./second is used. In another embodiment, a cooling rate of at least about 20° C./second is used. In another embodiment, a cooling rate of at least about 25° C./second is used. In another embodiment, a cooling rate of at least about 30° C./second is used. In another embodiment, a cooling rate of at least about 35° C./second is used. In another embodiment, a cooling rate of at least about 40° C./second is used. In another embodiment, a cooling rate of at least about 45° C./second is used. In another embodiment, a cooling rate of at least about 50° C./second is used. In other embodiments, cooling rates of at least about 60, 70, 80, 90 up to 100° C./second or more can be used. Accordingly, in the methods provided herein, the rate of cooling can be selected from the group consisting of rates of cooling of at least about: 3, 4, 5, 6, 7, 8, 9, 10, 15, 20, 25, 30, 35, 40, 45, 50, 60, 65, 70, 75, 80, 85, 90, 95 and at least about 100° C./second. In the methods and apparatus provided herein, the small thermal mass of the chip together with the reaction-containment member permits very fast cooling and heating rates, when compared to conventional thermocycling instruments for microtiter plates or microliter tubes as reaction vessels. It is the combination of providing an increased heating ramp rate along with an increased cooling rate that provides for the advantageous overall increase in the rate of thermocycling. For example, in one embodiment using the methods provided herein, a 40-55 thermocycle PCR amplification reaction can be performed in approximately 20 minutes, compared to the typical 100 to 150 minutes required by conventional methods. This rate of the PCR reaction corresponds to a range of about 22 to 30 seconds per thermocycle. In other embodiments provided herein, the rate of thermocycles for the reactions provided herein (such as primer extension and/or amplification reactions) can be in the range of about 5 seconds up to about 150 seconds per cycle. For example, in one embodiment, one cycle of a primer extension or amplification reaction is conducted in a time selected from ≦: about 150 seconds, about 140 seconds, 130 seconds, 120, seconds, 110 seconds, 100 seconds, 90 seconds, 80 seconds, 70 seconds, 60 seconds, 50 seconds, 40 seconds, 30 seconds, 20 seconds, 15 seconds, 10 seconds, 9 seconds, 8 seconds, 7 seconds, 6 seconds, or ≦about 5 seconds. Accordingly, in certain embodiments, a 40-55 thermocycle (e.g., 40, 45, 50 or 55 cycles) reaction (such as a primer extension or amplification) is conducted in ≦about 15 minutes. In another embodiment, a 40-55 thermocycle reaction is conducted in a time selected from ≦about 10, about 9, about 8, about 7, or ≦about 6 minutes. In another embodiment, a 40-55 thermocycle reaction is conducted in ≦about 5 minutes. Thus, the rate of thermocycles per hour for use herein ranges from about 20 thermocycles up to about 500 thermocycles/hour (e.g., about 0.3-8.3 PCR thermocycles/minute). Also contemplated herein are rates of thermocycles per minute of at least about 9, 10, 11, 12, 13, 14, 15 or more thermocycles/minute. Accordingly, the methods provided herein result in a significant reduction of the costs and time required for performing reactions that utilize thermocycling, such as nucleic acid primer extension and/or amplification (e.g., PCR) reactions.

Uniform temperature distribution across a nanowell as well as from one well to the next are also important functions of the substrates provided herein. Computer simulations using CFCRC software and experimental results indicate that the nanotiter chip system provided herein can perform 96 PCRs simultaneously with uniform temperature distribution. For example, a 3-phase nanotiter chip thermal heating simulation was conducted at 95° C. (368K). Only half of the chip was modeled due to the symmetry of the chip. Typically, thermal uniformity at higher temperatures, in this case of 95° C., is more difficult than at lower temperatures. As a comparison, temperature plots of two nanowells located near the chip edge and another near the chip center were generated. The results indicate that approximately 0.8° C. difference is observed within a well and 0.1° C. difference is observed from well to well. These temperature differences are dramatic improvements to standard microtiter plates where a temperature difference on the order of several degrees is readily observed. Accordingly, in particular embodiments, the temperature difference from within a single reaction chamber can be selected from $\leq$(less than or equal to): 2.0° C., 1.5° C., 1.0° C., 0.5° C. or $\leq$0.3° C. This means that within a single reaction chamber the temperature does not vary from any 2 locations within the reaction mixture by more than these amounts.

In these and other embodiments, the temperature difference between wells is $\leq$1.0° C., 0.5° C., 0.4° C., 0.3° C., 0.2° C. or $\leq$0.1° C. This means that between 2 separate reaction chambers on the same substrate (e.g., chip), the temperature does not vary from any 2 adjacent reaction chambers by more than these amounts. In another embodiment, the temperature does not vary from any 2 reaction chambers on the same substrate by more than these amounts.

In particular embodiments, the nucleic acid reaction products are captured at the discrete target detection location(s) within the reaction chamber or channels in the presence of which the thermocycling reaction or reactions occurred, without the need to physically transfer the reaction products to a different location prior to capture. In one embodiment, subsequent to an amplification reaction (e.g., PCR) and prior to the capture step, the amplified target nucleic acid in the reaction chamber or channel is subjected to a primer extension reaction. Advantageously, the methods provided herein permit the amplification of target nucleic acid, the primer extension of the amplification product and the subsequent capture of the reaction product(s) onto a solid-phase capture moiety (e.g., capture oligonucleotide) in a single reaction chamber or channel. Accordingly, provided herein is a method for determining the identity of a nucleotide in a target nucleic acid molecule, comprising hybridizing a single-stranded portion of the target nucleic acid molecule to an oligonucleotide that is complementary to a region of the single stranded portion of the target nucleic acid in solution and in the presence of a capture moiety at a discrete target detection location; exposing the hybridized nucleic acid and oligonucleotide to conditions that permit extension of the oligonucleotide; and capturing the product(s) of the extension reaction on the surface of the substrate at the discrete target detection location, wherein the capture is achieved through a non-covalent interaction between the product(s) and the surface of the substrate or a moiety attached to the surface of the substrate.

In addition, the methods described herein are particularly suitable for miniaturization. The design of the reaction-containment member, the method for fast thermocycling and using the substrate itself as a central part of the purification strategy as well as the stage for analysis leads to the option for significant volume reduction by a factor of 10 or more compared to previously known systems. Such volume reduction advantageously results in cost reduction, in terms of lowering costs of expensive components and reagents such as enzymes. Simultaneously, cost reduction in terms of space is achieved, by permitting the building of instruments around the substrates and the reaction-containment members that are smaller than conventional instruments (e.g., for liquid handling and thermocycling). Typically, biochemical reactions as described herein, are performed in relatively large microtiter plates or microliter tubes as reaction vessels with total reaction volumes between 5 and 50 microliters. The total reaction volumes for the methods provided herein, depend mainly on the design of the reaction-containment member and the substrate. Channels or wells, created by the reaction-containment member and the substrate can have, but are not limited to, a volume in microliters of no more than about 1000, 900, 800, 700, 600, 500, 400, 300, 250, 200, 150, 100, 50, 25, 20, 15, 10, 5, 4, 3, 2, or no more than about 1 microliter; or a volume in nanoliters of no more than about 1, 2, 3, 4, 5, 10, 15, 20, 25, 50, 100, 150, 200, 250, 300, 400, 500, 600, 700, 800, 900 or no more than about 1000 nanoliter. Typically used total reaction volumes are no more than about 4, 3, 2, 1.5 or 1 microliter; or no more than about 900, 800, 700, 600, 500, 400, 300, 200, 100 or 50 nanoliter.

1. Biomolecules

Any biomolecule that may be of interest can be reacted and analyzed in the methods provided herein. Such biomolecules include, but are not limited to, nucleotides, polynucleotides, nucleic acids, amino acids, peptides, proteins, carbohydrates, lipids and other small organic molecules, and conjugates of such molecules. The biomolecules can be obtained from a number of sources. For example, biomolecules may be obtained from samples from subjects, such as cell samples, tissue samples and fluid samples, e.g., blood, saliva, urine, biopsy and cell culture medium.

(a) Nucleotides and Nucleic Acids

Nucleotides and nucleic acids can be obtained using methods described herein and standard methods known to those of skill in the art. Such techniques can be used, for example, to isolate DNA from blood, saliva, skin and body tissues, or to synthesize nucleic acids that may be used in screening methods.

A common source of nucleic acids to be analyzed is blood which can be obtained from blood banks and diagnostic laboratories. Isolation of DNA from blood can be done, for example, as follows. Through a series of centrifuging in various buffers and washes, a white cell pellet is isolated from a blood sample. Proteins are then precipitated from the cell lysate and separated from the nucleic acid by centrifugation. The nucleic acid is recovered from the supernatant by the addition of an, equal volume of 100% isopropanol and centrifugation. Methods of nucleic acid synthesis are also well known in the art.

(b) Amino Acids, Peptides and Proteins

Amino acids, peptides and proteins can be obtained from samples using methods described herein and standard methods known to those of skill in the art. Such techniques can be used, for example, to isolate proteins from cells, blood, saliva, skin and body tissues, or to synthesize peptides and proteins that may be used in screening methods.

Methods of peptide and protein isolation and synthesis are known in the art (Martin, R., *Protein synthesis: methods and protocols, published by Totowa, N.J.: Humana Press, c*1998). In addition generation of protein via phage display methods is also well known in the art (Mathews, C. K. et. al., *Bacterioph-* age *T*4, published by American Society for Microbiology, Washington, D.C., c1983, Cantor, C et. al., *Genomics*, published by John Wiley & Sons, Inc, NY, c 1999, Park, J H et al., Biomaterials, 2002, 23, 1797-1808), as well as phage display methods.

(c) Organic Molecules

Organic molecules can be extracted from well known sources, obtained from commercially available compound libraries or synthesized using a variety of methods known in the art, including combinatorial chemistry methods.

(d) Carbohydrates

Carbohydrates can be isolated from sources such as cell samples and tissue samples. Carbohydrates can also be synthesized using a variety of methods well known in the art (e.g., see Haase, W. C. et. al. 2001, Solid Support Oligosaccharide Synthesis and Combinatorial Carbohydrate Libraries, 1-13, Kadota, K. et. al. 2001, 42, 8661-8664).

2. Reactions of Biomolecules

The biomolecules to be analyzed in methods provided herein are subjected to one or more reactions prior to and/or during analysis thereof. The biomolecules are applied to a substrate, e.g., introduced into a chamber having a substrate as one or more of the walls and/or interior bottom of the chamber, as described herein, on which the reaction(s) will occur and from which a reaction product will be analyzed. In particular embodiments of the methods, multiple reactions, e.g., two or more, or three or more reactions, are performed at a single location on the substrate or in a single chamber.

The reaction(s) performed in the chamber that involve the introduced biomolecule(s) can be conducted substantially or completely in solution and in low volumes in the chamber and may be any type of chemical, enzymatic or biochemical reaction. In particular embodiments of the methods provided herein, at least one of the reactions involves altering the temperature of the reaction mixture. Generally, the reactions are designed to ultimately yield a product that provides information about the introduced biomolecule, such as, for example, its identity, structure, functional characteristics or sequence of monomer units (e.g., if the biomolecule is a biopolymer such as a nucleic acid or peptide). Examples of the types of reactions that can be performed in the methods provided herein include, but are not limited to, the following.

(a) Reactions Involving Nucleic Acids

Many different reactions, and variations thereof, are commonly performed in the analysis of nucleic acids. Principle among such reactions are enzymatic reactions in which a nucleic acid is amplified to increase the amount of target nucleic acid for analysis. Other reactions include, for example, primer extension reactions, sequencing reactions, fragmentation reactions (e.g., using specific endonucleases), cleavage reactions of mismatched heteroduplexes of nucleic acids, oligonucleotide ligation reactions and single-stranded conformation reactions.

(i) Nucleic Acid Amplification Reactions

Several nucleic acid amplification reactions are known in the art and described herein. A common amplification reaction, referred to as polymerase chain reaction (PCR) can be performed according to any methods known in the art. For example, in one PCR protocol, genomic DNA of a cell is exposed to two PCR primers and amplification is performed for a number of cycles sufficient to produce the required amount of amplified DNA. The primers can be located, for example, between about 50 and 350, 500 or even 1000 base pairs apart.

If a multiplex PCR amplification is to be carried out, initially a large region encompassing more than one segment of a nucleic acid molecule can be amplified using primers outside the area, followed by amplification of each sub-region or segment using specific primers for each site. Some of the limitations of multiplex PCR include partial binding between PCR primers or between PCR primers and other primers or other regions of the genomic DNA apart from the target site, thus resulting in side products and reduced yields of the desired PCR products. Those of ordinary skill in the art are familiar with the design and limitations of multiplex PCR.

Additional methods of amplifying nucleic acids include, but are not limited to, mini-PCR, ligase chain reaction (LCR) [Wiedmann et al. (1994) *PCR Methods Appl*. Vol. 3, Pp. 57-64; Barnay (1991) *Proc. Natl. Acad. Sci. USA* 88:189-93], strand displacement amplification (SDA) [Walker et al. (1994) *Nucleic Acids Res*. 22:2670-77], RT-PCR [Higuchi et al. (1993) *Bio/Technology* 11:1026-1030], rolling circle amplification, autocatalytic methods, such as those using QJ replicase, TAS, 3SR, and any other suitable method known to those of skill in the art.

Alternative amplification methods include: self sustained sequence replication (Guatelli et al. (1990) *Proc. Natl. Acad. Sci. USA*. 87:1874-1878), transcriptional amplification system (Kwoh et al. (1989) *Proc. Natl. Acad. Sci. U.S.A*. 86:1173-1177), Q-Beta Replicase (Lizardi et al. (1988) *Bio/Technology* 6:1197), or any other nucleic acid amplification method, followed by the detection of the amplified molecules using techniques well known to those of skill in the art and disclosed herein. These detection schemes are especially useful for the detection of nucleic acid molecules if such molecules are present in very low numbers. Alternatively, allele specific amplification technology, which depends on selective PCR amplification may be used. Oligonucleotides used as primers for specific amplification may carry the allelic variant of interest in the center of the molecule (so that amplification depends on differential hybridization) (Gibbs et al. (1989) *Nucleic Acids Res*. 17:2437-2448) or at the extreme 3' end of one primer where, under appropriate conditions, mismatch can prevent, or reduce polymerase extension (Prossner (1993) *Tibtech* 11:238; Newton et al. (1989) *Nucl. Acids Res*. 17:2503). In addition it may be desirable to introduce a restriction site in the region of a mutation to create cleavage-based detection (Gasparini et al. (1992) *Mol. Cell. Probes* 6:1).

(ii) Primer Extension Reactions

Primer extension reactions involve the specific termination of polymerase-mediated nucleic acid chain elongation by the incorporation of a chain terminator, e.g., a dideoxynucleotide, into the elongation reaction. Several primer extension-based methods are known in the art and have been used for determining the identity of a particular nucleotide in a nucleic acid sequence (see, e.g., PCT Application Nos. PCT/US96/03651 (WO 96/29431), PCT/US97/20444 (WO 98/20166), PCT/US97/20194 (WO 98/20019), PCT/US91/00046 (WO 91/13075); and U.S. Pat. Nos. 5,547,835, 5,605,798, 5,622, 824, 5,691,141, 5,872,003, 5,851,765, 5,856,092, 5,900,481, 6,043,031, 6,133,436 and 6,197,498.) In general, a primer is prepared that specifically hybridizes adjacent to a site of interest, e.g., a polymorphic site, in a particular nucleic acid molecule. The primer is then extended in the presence of one or more dideoxynucleotides, typically with at least one of the dideoxynucleotides being the complement of the nucleotide that is polymorphic at the site. The primer extension and/or the identity of the extended nucleotide(s) can be determined in a number of ways. In particular methods, extension is determined by mass spectrometry (see, e.g., PCT Application Nos. PCT/US96/03651 (WO96/29431), PCT Application No. PCT/US97/20444 (WO 98/20166), PCT Application No.

PCT/US97/20194 (WO 98/20019), PCT Application No. PCT/US91/00046 (WO91/13075), and U.S. Pat. Nos. 5,605, 798, 5,622,824, 5,856,092.

In one variation of the primer extension reaction, both dideoxynucleotides and deoxynucleotides are used. For example, when such a reaction is used to extend a primer hybridized to one of two alleles, the possible extension products for one polymorphic site are in this case usually one-base extended products for one genotype and two- (or more)-base extended products for other possible genotypes. Mass spectrometry is particularly well suited for determining extension in connection with this reaction scheme because the possible products differ essentially in their molecular weight. When a double-stranded nucleic acid molecule (e.g., a PCR product) serves as a template, the primer extension reaction should be thermocycled in order to achieve sufficiently high reaction yields to be detected. In cyclic temperature programs, the double-stranded structures are temporarily denatured to allow for unextended primer to anneal adjacent to the site of interest in competition with the complementary PCR strand. This can be a time-consuming process using standard thermocycler instrumentation, requiring approximately 90 minutes or more. Using apparatus provided herein (i.e., a fast thermocycler which heats up the small mass of a chip substrate and the low-volume reaction mixture contained in a chamber having the chip surface as an interior bottom directly), the duration of this thermocycling process can be reduced to about approximately 15 minutes.

(iii) Fragmentation Reactions

The presence or absence of one or more mutations, such as polymorphisms, within specific nucleic acids, including PCR products or other amplification products, can be determined from fragments of these nucleic acids. The fragments can be generated by different chemical and/or enzymatic reactions. For any of these fragmentation reactions, the molecular weights of the nucleic acid fragment(s) obtained after the reaction can be determined by mass spectrometry (see, e.g., U.S. Pat. Nos. 5,605,798, 6,043,031, 6,197,498, 6,221,601, 6,221,605, 6,235,478, 6,258,538, 6,268,144, 6,277,573, and 6,300,076 and International PCT Application Publication No. WO96/29431).

The target nucleic acid can be characterized through its whole fragmentation pattern, characterizing the complete sequence or through selected parts of the fragmentation pattern. Certain fragments of the nucleic acid can be selectively isolated and purified, for example through capture by hybridization on the substrate or through other specific interactions, like Biotin/Streptavidin affinity of one or more fragments. Methods for isolating and purifying all or most of the generated fragments, includes for example specific and unspecific (e.g., through the use of polyinosine) capture by hybridization on a substrate as well as substrates that bind fragments through ionic, hydrogen bond or hydrophobic interaction, chelating ligands, affinity interaction or through other means known to those skilled in the art.

One method for generating fragments of nucleic acids, preferably from amplification products, is the use of one or more restriction enzymes. Analyzing the number, size and/or composition of the product(s) of the reaction will provide information about the nucleic acid and its variants at one or multiple sites. For example, a specific nucleotide polymorphism within an amplification product can contain a restriction endonuclease site, which is absent in the nucleotide sequence of another allelic variant. This creates two largely different products, that can be selectively separated and analyzed. In other assay designs restriction enzymes can create characteristic fragments around one or more polymorphic sites. Similar to this approach, cleavage with RNases can be used for the fragmentation of RNA or RNA/DNA chimeras. The nucleic acids can be generated by well known amplification methods such as PCR and/or in vitro transcription with DNA dependent RNA polymerases (Sambrook, J., Fritsch, E. F. and Maniatis, T. (2001) Molecular Cloning: A Laboratory Manual, Second Ed., Cold Spring Harbor Laboratory Press, Cold Spring Harbor, N.Y., Chap. 10.27-10.33). These products can be captured on the surface, purified and treated with RNAses prior to analysis with mass spectrometry. Alternatively to fragmentation on the surface, this step can be performed in solution and certain fragments can be specifically extracted through hybridization to their complements or through fragment specific modifications, for example biotinylation.

Uracil-specific cleavage of a nucleic acid can be effected by reacting a uracil-N-glycosylase with the nucleic acid (see, e.g., International PCT Application Publication No. WO 98/54571). The nucleic acid being treated with the glycosylase can be generated in an amplification reaction using uracil bases for incorporation into the amplification products. For any of the reactions that can result in cleavage of a nucleic acid, the molecular weights of the DNA fragment(s) obtained after the reaction can be determined by mass spectrometry and be used to detect the presence of a mutation in a nucleic acid (see, e.g., U.S. Pat. Nos. 5,605,798, 6,043,031, 6,197, 498, 6,221,601, 6,221,605, 6,235,478, 6,258,538, 6,268,144, 6,277,573, and 6,300,076 and International PCT Application Publication No. WO96/29431). Again the complete fragmentation pattern or individual fragments can be separated and analyzed as described above.

(iv) Sequencing Reactions

A variety of nucleic acid sequencing reactions are known in the art and can be used to identify a particular nucleic acid. Exemplary sequencing reactions include those based on techniques developed by Maxam and Gilbert [(1977) *Proc. Natl. Acad. Sci. USA* 74:560] or Sanger [Sanger et al. (1977) *Proc. Natl. Acad. Sci. U.S.A.* 74:5463]. It will be evident to one skilled in the art that, for certain embodiments, the occurrence of only one, two or three of the nucleic acid bases need be determined in the sequencing reaction. For instance, A-track sequencing or an equivalent, e.g., where only one nucleotide is detected, can be carried out. Other sequencing methods are known (see, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing").

In particular methods, the products of the sequencing reactions may be analyzed by mass spectrometry (see, for example, U.S. Pat. Nos. 5,547,835, 5,691,141, and International PCT Application No. PCT/US94/00193 (WO 94/16101), entitled "DNA Sequencing by Mass Spectrometry" by H. Koster; U.S. Pat. Nos. 5,547,835, 5,622,824, 5,851,765, 5,872,003, 6,074,823, 6,140,053 and International PCT Application No. PCT/US94/02938 (WO 94/21822), entitled "DNA Sequencing by Mass Spectrometry Via Exonuclease Degradation" by H. Koster). In a particular example of a method provided herein, a target nucleic acid to be sequenced is applied to a substrate along with all of the reagents required to conduct Sanger-type sequencing reactions, including primers. The sequencing fragments generated in the reactions are captured on the surface of the substrate through hybridization to substrate-bound oligonucleotides that contain a sequence that is the complement of a portion of or the entire sequencing primer. Following desalting on the substrate surface and addition of matrix to the surface of the substrate, each sequencing fragment can be detected and analyzed by MALDI mass spectrometry initiated at the location of the captured fragments on the substrate surface, i.e., the target detection location.

(v) Mismatch Cleavage Reactions Protection from cleavage agents, such as, but not limited to, a nuclease, hydroxylamine or osmium tetroxide and with piperidine, can be used to detect mismatched bases in RNA/RNA, DNA/DNA, or RNA/DNA heteroduplexes (Myers, et al, (1985) *Science* 230:1242). In general, the technique of "mismatch cleavage" starts by providing heteroduplexes formed by hybridizing an oligonucleotide complementary to a target nucleic acid molecule, such as RNA or DNA, with a nucleic acid, such as RNA or DNA, obtained from a sample. The double-stranded duplexes are treated with an agent, which cleaves single-stranded regions of the duplex, such as duplexes formed based on basepair mismatches between the oligonucleotide and sample strands. For instance, RNA/DNA duplexes can be treated with RNAse and DNA/DNA hybrids treated with S1 nuclease to enzymatically digest the mismatched regions. Thus, a mismatch, which can indicate the presence of a mutation, results in the cleavage of the target nucleic acid. In particular methods, the cleavage products can be detected by mass spectrometry (see, e.g., U.S. Pat. Nos. 5,605,798, 6,043,031, 6,197,498, 6,221,601, 6,221,605, 6,235,478, 6,258,538, 6,268,144, 6,277,573, and 6,300,076 and International PCT Application Publication No. WO 96/29431).

In other embodiments, either DNA/DNA or RNA/DNA duplexes can be treated with hydroxylamine or osmium tetroxide and with piperidine in order to digest mismatched regions. After digestion of the mismatched regions, the resulting material can be analyzed, for instance by mass spectrometry, to determine the presence and molecular weights of any nucleic acid fragments. In a particular example of a method provided herein, any fragment produced in the mismatch cleavage reaction is captured on the substrate surface through hybridization to an immobilized oligonucleotide having a sequence complementary to all or a portion of the fragment. Following desalting on the substrate surface and addition of matrix to the surface of the substrate, each fragment can be detected and analyzed by MALDI mass spectrometry initiated at the location of the captured fragments on the substrate surface, i.e., the target detection location.

In an exemplary embodiment related to mismatch cleavage reactions, a ribo-oligonucleotide complementary to the SNP region of the DNA target can be attached to the solid support surface. The DNA target is amplified by methods such as PCR or others, on top of the surface. One strand of the amplification product is removed or the amplification is directed in a way that the target DNA is produced in excess. This strand of the DNA target is then captured on the surface through hybridization to the surface-attached complementary ribo-oligonucleotide. If a single base mismatch occurred at the site of the SNP, the formed duplex would be puckered and therefore partially single stranded. A cleaving agent that cleaves single strands (e.g., RNAses), can then be used to cleave the ribo-oligonucleotide at this site. The cleavage generates a free short portion of the ribo-oligonucleotide that can be analyzed, for example by analysis via MALDI-TOF mass spectrometry after adding matrix compounds to the surface. Only if a mismatch was present in the sample, then a peak corresponding to the cleaved ribo-oligonucleotide fragment would result, while no MALDI-MS signal would occur for a perfect match. In one embodiment, this system could be analyzed by fluorescence instead of mass spectrometry by attaching a fluorescence tag to the end of the surface attached ribo-oligonucleotide. If a mismatch between the ribo-oligonucleotide and the PCR product occurred, the cleavage would result in a free short portion of the ribo-oligonucleotide, bearing the fluorescence signal on the surface. However, in the case of a perfect match, then no cleavage would occur, resulting in a fluorescence signal on the surface.

In another embodiment, PCR or other methods for the amplification of DNA targets could be performed over the surface. One strand of the amplification product is removed or the amplification is directed in a way that the target DNA is produced in excess. This is followed by the addition of the ribo-oligonucleotide sequence complementary to one of the allele SNP types of the PCR product. A mismatched and/or a matched hybrid between the ribo-oligonucleotide sequence and the PCR product is then formed in solution. RNAse A is then added to the solution. As in the above embodiment, if a mismatch occurred between the ribo-oligonucleotide and the PCR product then cleavage of the ribo-oligonucleotide sequence would result. If a perfect match occurred, then no cleavage would be evident. The ribo-oligonucleotide whether cleaved or uncleaved is then captured onto the surface through hybridization to a surface attached oligo complementary to at least parts of the sequence of the ribo-oligonucleotide. Following matrix addition, MALDI-TOF mass spectrometry is used to identify the cleaved and uncleaved products. In a particular embodiment, this system can be analyzed by fluorescence rather than mass spectrometry by placing a fluorescence tag at the 5' or 3'-end of the ribonucleotide sequence. The surface attached oligonucleotide can be designed such that it is exclusively captured at the end of the target sequence opposite to the fluorescence tag and upstream from the potential cleavage site. If cleavage occurred then no fluorescence signal would be detected while if no cleavage occurred a fluorescence signal would be detected.

(vi) Oligonucleotide Ligation Reaction

In another nucleic acid reaction scheme, referred to as oligonucleotide ligation, two oligonucleotides, designed to be capable of hybridizing abutting to sequences of a single strand of a target nucleic acid, are mixed with sample nucleic acid. If the precise complementary sequence is found in a sample nucleic acid, the oligonucleotides will hybridize such that their termini abut, and create a ligation substrate. Thus, a nucleic acid in a sample may be detected using an oligonucleotide ligation assay (OLA), as described, e.g., in U.S. Pat. No. 4,998,617 and in Landegren et al., *Science* 241:1077-1080 (1988). Nickerson et al. have described a nucleic acid detection assay that combines attributes of PCR and OLA [Nickerson et al. (1990) *Proc. Natl. Acad. Sci. U.S.A.* 87:8923-8927]. In this method, PCR is used to achieve the exponential amplification of target DNA, which is then detected using OLA.

Several techniques based on this OLA method have been developed and can be used to detect specific allelic variants of a polymorphic region of a gene. For example, U.S. Pat. No. 5,593,826 discloses an OLA using an oligonucleotide having 3'-amino group and a 5'-phosphorylated oligonucleotide to form a conjugate having a phosphoramidate linkage. In other protocols, based on the ligase chain reaction (LCR), a target nucleic acid is hybridized with a set of ligation educts and a thermostable DNA ligase, so that the ligase educts become covalently linked to each other, forming a ligation product. In particular methods, the ligation product can be detected by mass spectrometry and compared to a known value (see, e.g., U.S. Pat. Nos. 5,605,798, 6,043,031, 6,197,498, 6,221,601, 6,221,605, 6,235,478, 6,258,538, 6,268,144, 6,277,573, and 6,300,076 and PCT Application Publication No. WO96/29431). If the reaction is performed in a cyclic manner, the ligation product obtained can be amplified to better facilitate detection of small volumes of the target nucleic acid. Selection between wildtype and mutated primers at the ligation point can result in a detection of a point mutation.

In certain embodiments of the methods provided herein, ligase chain reactions can be performed substantially in solution on top of a solid support for example to determine single nucleotide polymorphisms. For example, an oligonucleotide complementary to a portion of the ligation product could be attached to the solid support. Over and in the presence of the solid-support immobilized oligonucleotide, PCR is first conducted followed by the ligation reaction. For the ligation reaction, three ligation primers would be added to the solution: one complementary to the oligonucleotide attached to the surface; one primer containing the wild-type SNP; and another primer containing the mutant-type SNP. The ligation products, corresponding to wild type and/or mutant sequences, are then captured on the surface and identified by their molecular weight using mass spectrometry analysis, such a MALDI-TOF mass spectroscopy. In another embodiment for analysis by fluorescence, the ligation primers containing the wild type and mutant type SNP are each labeled with different fluorescence tags. For example, the wild-type primer can be labeled with a cy5 while the mutant type primer can be labeled with cy3. In this way, the presence of mutant and/or wild type sequences can be identified. In particular embodiments, multiplexed PCR and ligation reactions are performed.

In another embodiment, the surface immobilized oligonucleotide could capture the PCR product through hybridization. The ligation product(s) would then hybridize to the surface captured PCR product.

(b) Reagents that can be Used in Nucleic Acid Reactions

As is evident from the types of reactions involving nucleic acids, a number of reagents can be used in such reactions. Reagents include enzymes (e.g., polymerases, endonucleases, exonucleases, S1 nuclease, ligases), primers, oligonucleotides, deoxynucleoside triphosphates (dNTPs) and dideoxynucleoside triphosphates (ddNTPs).

(i) Primers

Primers refer to nucleic acids which are capable of specifically hybridizing to a nucleic acid sequence (often referred to as a template) at a position which is adjacent to a region of interest, for example, a polymorphic region. A primer can be extended through the action of an enzyme, e.g., a polymerase, in a process whereby nucleotides or analogs thereof that are complementary to the template adjacent to the primer are added to the growing nucleotide chain. For example, if an RNA template is used, an oligodeoxynucleotide primer can be extended through the action of reverse transcriptase to generate a cDNA complementary to the RNA template. If a DNA template is used, a primer can be extended through the action of a DNA polymerase.

A primer can be used alone, for example in a primer extension reaction designed to provide information on the identity and/or presence of a target nucleic acid, or a primer can be used together with at least one other primer or probe, e.g., in an amplification reaction. For amplifying at least a portion of a nucleic acid, a forward primer (i.e., 5' primer) and a reverse primer (i.e., 3' primer) will preferably be used. Forward and reverse primers hybridize to complementary stands of a double-stranded nucleic acid, such that upon extension from each primer, a double stranded nucleic acid is amplified.

Primers (RNA, DNA (single-stranded or double-stranded), PNA and their analogs) described herein may be modified without changing the substance of their purpose by terminal addition of nucleotides designed, for example, to incorporate restriction sites or other useful sequences.

A primer can be prepared according to methods well known in the art and described, e.g., in Sambrook, J. and Russell, D. (2001) Molecular Cloning: A Laboratory Manual, Third Ed., Cold Spring Harbor Laboratory Press, Cold Spring Harbor, N.Y. For example, discrete fragments of the DNA can be prepared and cloned using restriction enzymes.

Alternatively, primers can be prepared using the Polymerase Chain Reaction (PCR) using primers having an appropriate sequence or they can be synthesized.

Primers, and in particular primers used in reactions conducted in methods of detecting allelic variants, are of sufficient length to specifically hybridize to portions of an allele at polymorphic sites. Typically such lengths depend upon the complexity of the source organism genome. For humans such lengths are at least 14-16 nucleotides, and typically may be 20, 30, 50, 100 or more nucleotides.

(ii) Nucleosides/Nucleotides

Many reactions involving nucleic acids include deoxynucleoside triphosphates (dNTPS) and dideoxynucleoside triphosphates (ddNTPs) as the building blocks which can be used, for example, to extend a primer in extension, amplification and sequencing reactions. In certain reactions, it can be desirable to use modified dNTPS to facilitate identification and/or detection of the products of the reactions or to distinguish the products of different reactions. For example, a molecular weight difference between the nucleic acid products of different reactions can be achieved either by the nucleic acid sequence itself (composition or length) or by the introduction of mass-modifying functionalities into the products. For example, mass modifications can be incorporated during a nucleic acid amplification process.

Mass modifying moieties can be attached, for instance, to the 5'-end of the product nucleic acid, to the nucleobase (or bases), to the phosphate backbone, and to the 2'-position of the nucleoside (nucleosides) and/or to the terminal 3'-position. Examples of mass modifying moieties include, for example, a halogen, an azido, or of the type, XR, wherein X is a linking group and R is a mass-modifying functionality. The mass-modifying functionality can thus be used to introduce defined mass increments into the product nucleic acid molecule.

Modification of the 5' end of a nucleic acid sequence during the synthesis of a primer is one way of introducing differences in masses of two or more product nucleic acids. Most 5'-end modifications will not interfere with the stability of the hybrid formed between, for example, a capture sequence and a product nucleic acid or with the efficiency of primer extension reactions, occurring on the 3' end. The modifications can be introduced during the synthesis, for example with phosphoramidite chemistry and the great variety of compounds of this class that are commercially available, adding nucleotides, nucleotide derivatives, deoxyribose-3'-phosphate-, 5'-phosphate- and any other organo-3'-phosphate group.

The mass-modifying functionality can be located at different positions within the nucleotide moiety (see, e.g., U.S. Pat. No. 5,547,835 and International PCT Application No. WO 94/21822). For example, the mass-modifying moiety, M, can be attached either to the nucleobase, (in case of the $c^7$-deaza-nucleosides also to C-7), to the triphosphate group at the alpha phosphate or to the 2'-position of the sugar ring of the nucleoside triphosphate. Modifications introduced at the phosphodiester bond, such as with alpha-thio nucleoside triphosphates, have the advantage that these modifications do not interfere with accurate Watson-Crick base-pairing and additionally allow for the one-step post-synthetic site-specific modification of the complete nucleic acid molecule e.g., via alkylation reactions (see, e.g., Nakamaye et al. (1988)

Nucl. Acids Res. 16:9947-59). Boron-modified nucleic acids are also useful mass-modifying functionalities since they are better incorporated into nucleic acids by polymerases (see, e.g., Porter et al. (1995) Biochemistry 34:11963-11969; Hasan et al. (1996) Nucleic Acids Res. 24:2150-2157; Li et al (1995) Nucl. Acids Res. 23:4495-4501).

Furthermore, the mass-modifying functionality can be added so as to affect chain termination, such as by attaching it to the 3'-position of the sugar ring in the nucleoside triphosphate. For those skilled in the art, it is clear that many combinations can be used in the methods provided herein. In the same way, those skilled in the art will recognize that chain-elongating nucleoside triphosphates can also be mass-modified in a similar fashion with numerous variations and combinations in functionality and attachment positions.

For example, without being bound to any particular theory, the mass-modification can be introduced for X as well as for R in XR using polyethylene glycol derivatives of oligonucleotides. The mass-modifying increment (m) in this case is 44, i.e., five different mass-modified species can be generated by just changing m from 0 to 4 thus adding mass units of 45 (m=0), 89 (m=1), 133 (m=2), 177 (m=3) and 221 (m=4) to the nucleic acid molecule (e.g., or the nucleoside triphosphates). The polyethylene glycol derivatives of oligonucleotides can also be monoalkylated by a lower alkyl such as, but not limited, methyl, ethyl, propyl, isopropyl and t-butyl. Other chemistries can be used in the massmodified compounds (see, e.g., those described in Oligonucleotides and Analogues, A Practical Approach, F. Eckstein, editor, IRL Press, Oxford, 1991).

Various mass-modifying functionalities, R, other than polyethylene glycol derivatives of oligonucleotides, can be selected and attached via appropriate linking chemistries, X. Simple mass-modification can be achieved such as by substituting halogens for H, such as F, Cl, Br and/or I, or pseudohalogens such as CN, SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g., or nucleoside triphosphates). One example, useful in generating mass-modified species with a mass increment of 57, is the attachment of oligoglycines (m) to nucleic acid molecules (r), e.g., mass-modifications of 74 (r=1, m=0), 131 (r=1, m=1), 188 (r=1, m=2), 245 (r=1, m=3) are achieved. Simple oligoamides also can be used, e.g., mass-modifications of 74 (r=1, m=0), 88 (r=2, m=0), 102 (r=3, m=0), 116 (r=4, m=0), etc. are obtainable. Variations in addition to those set forth herein will be apparent to the skilled artisan.

(c) Conditions used in Nucleic Acid Reactions

Reactions involving nucleic acids typically include steps of hybridizing two or more nucleic acid molecules. The extent and specificity of hybridization varies with reaction conditions, particularly with respect to temperature and salt concentrations. Hybridization reaction conditions typically are referred to in terms of degree of stringency, e.g., low, medium and high stringency, which are achieved under differing temperatures and salt concentrations known to those of skill in the art and exemplified herein. Thus, for example, to reduce the amount of imperfect matches between hybridizing nucleic acids, higher stringency conditions may be employed, e.g., higher temperatures and lower salt concentrations.

In addition, reactions involving nucleic acids can also include steps in which duplex nucleic acids are denatured to yield single-stranded molecules. Denaturation may be achieved, for example, under conditions in which the temperature of the reaction mixture exceeds that of the melting temperature of a particular duplex nucleic acid.

Numerous nucleic acid reactions, for example, amplification reactions, involve repeated cycles of elevation and reduction of temperature to provide for denaturation and annealing of the strands of nucleic acid hybrids. Apparatus provided herein facilitate variation of the temperature of the reaction mixture in a chamber through a direct, rapid and efficient heating and cooling of the relatively low mass and high thermoconductivity of the substrate bottom of the chamber and by avoiding any steps of transferring the reactants into a separate thermocycler instrument.

(d) Reactions Involving Proteins or Peptides

There are several different types of reactions involving proteins or peptides that contemplated for use in the methods provided herein. For example, proteins and polypeptides can be captured onto oligonucleotide or DNA microarrays (Brockman, J. et al. (1999) Journal of the American Chemical Society 121:8044-8051. Epitoped tagged proteins can be captured through affinity to $Ni^{2+}$ chelated surfaces or to surface bound antibodies (Nelson, R. W. et al. (1999) Anal. Chem. 71: 2858-2865). Proteins can also be captured to surfaces to surface bound enzymes (Nelson, R. W. et al. (1997) Anal. Chem. 69: 4369-4374; Nelson, R. W. et al. (2001) Anal. Chem. 73: 1-7; Nedelkov, D. et al. (2000) Analytica Chimica Acta 423: 1-7). In other embodiments the interaction of proteins to protein immobilized surfaces can be used to capture solution-phase target proteins or peptides onto a solid-phase substrate (MacBeath, G. et al. (2000) Science 289:1760-1762; Lin, S. et al (2000) 72: 2635-2640)).

(i) Capture of Proteins to Oligonucleotide or DNA Immobilized Surfaces

The function of certain proteins is to recognize specific oligonucleotide sequences. Conformational changes in these proteins due to, for example, single nucleotide polymorphisms could hinder the function of such proteins. In order to study protein/oligonucleotide interactions in the platform and methods provided herein, the capture oligonucleotides of interest can be immobilized onto surfaces. The protein(s) of interest are first be expressed from cDNA phage vector libraries. These protein(s) are then introduced to the surfaces and the protein(s) are subsequently captured through affinity to the surface immobilized oligos. Following washing and addition of matrix compounds to the surface, analysis of the products by MALDI-TOF mass spectrometry could be performed. The identity of the proteins captured on the surfaces as well as the amount of protein present can be gauged.

In another embodiment, the proteins captured on the surface can also be analyzed by fluorescence by tagging the proteins with a fluorescence tag such as fluorescein or cy5. If various proteins were used, each protein would be tagged with a different fluorescence tag. In this way, the identity and relative amount of protein on the surface could be determined.

(ii) Proteins Affinity Capture to $Ni^{2+}$ Chelated, Antibody or Antibody Immobilized Surfaces In other embodiments, proteins and peptides can be isolated and characterized through their particular affinity for surface immobilized enzymes, antibodies and $Ni^{2+}$ chelate. In these embodiments, new proteins can be characterized. In one embodiment, proteins can be generically captured by tagging the proteins with a biomolecule. In this way, the protein is captured onto surfaces via affinity of the tag to a corresponding surface-attached biomolecule. The tag can be introduced to the protein, by inserting a DNA tag into a gene using cloning vectors or an insertion vehicle such as CD-tagging (Jarvik, J. W. et. al (1996) Biotechniques 20: 896-

904). The tag-containing proteins are obtained after protein expression. Following digestion with trypsin, the tag-containing peptide fragments can be captured through affinity of the tag to the surface-attached biomolecule. The tag could be a histidine-rich polypeptide which has a high affinity for $Ni^{2+}$ chelated surfaces. The Ni2+ chelated surface is formed by running a $Ni^{2+}$ buffer over a nitrilotriacetic acid derivatized surface. The captured proteins and polypeptides can be identified by MALDI-TOF mass spectrometry after application of MALDIMS matrix to the surface.

In another embodiment, the proteins can be captured onto the surface through affinity to surface immobilized enzymes and/or antibodies. Primary amines on the enzyme or antibody can be covalently attached to surfaces, for instance, and activated with N-hydroxysuccinimide aminopropylcarbodiimide. The masses of the captured proteins can be determined by MALDI-TOF mass spectrometry. Similarly, these captured proteins can be analyzed by fluorescence by attaching a fluorescence tag onto the proteins. A different fluorescence tag can be used for each protein. In this way the identity and the relative amount of protein on the surface can be gauged.

(iii) Protein Capture onto Protein Attached Surfaces.

In other embodiments of the methods provided herein, protein-protein interactions can be analyzed by immobilizing the proteins of interest onto surfaces. In one embodiment, the lysine residues on proteins can be covalently attached to for instance an aldehyde surface through Schiff base formation. Proteins can thus then be captured onto the surface. After washing and MALDI-MS matrix application to the surface, the masses of the proteins can be obtained via MALDI-TOF mass spectrometry. Similarly, if the proteins are tagged with fluorescence markers, the proteins and the relative amount of proteins can be determined via fluorescence.

(e) Reactions Involving Small Organic Molecules

The study of protein/small organic molecule interactions are important in elucidating protein function as well as gaining information on the possible therapeutic relevance of the small organic molecules. There are several well known reactions for the capture of small organic molecules onto surfaces. For example, in one embodiment, small organic molecules can be captured onto protein immobilized surfaces. The lysine residues on the proteins of interest can be covalently attached to, for instance, an aldehyde surface through Schiff base formation. Then the small organic molecules of interest can be introduced on top of the surface for specific or unspecific binding to the protein structure. The captured organic molecules can be identified by MALDI-TOF mass spectrometry. In another embodiment, the organic molecules can also be identified using fluorescence. In this method, each organic molecule used would have a different fluorescence tag. The identity as well as the relative amount of organic molecule could be determined.

(f) Reactions Involving Carbohydrates

Some antigen host receptors are composed of carbohydrates. In addition, the host receptors can also be complex carbohydrates located on the surfaces of cells. Gaining more understanding in host receptor/antigen/antibody interaction can provide more information on the pathways of infectious diseases. In addition, with such information, drugs can be designed to prevent these disease. Carbohydrate microarrays are known in the art (Wang, D et al. 2002, Nature 20, 275-281). In one embodiment, carbohydrate containing antigens are immobilized to nitrocellulose or nylon derivitized surfaces. Fluorescently tagged antibodies could then be introduced to the surface. The affinity of specific antibodies for various surface immobilized antigens could then be identified by fluorescence or by MALDI-TOF mass spectroscopy.

3. Capture of Reaction Products (a) Substrates for Capturing Reaction Products

Reaction products are captured on the surface of a substrate, e.g., on the interior bottom surface of a chamber, over which the reaction(s) are performed. In a particular embodiment, the reaction(s) is performed in a chamber that contains, or the bottom of the chamber is, a substrate that is capable of specifically interacting with the reaction(s) product in such a way as to retain it attached to the substrate during processes used to remove or wash other molecules from the chamber. The interaction can be between the reaction product and an actual chemical component of the substrate itself or between the reaction product and a component that has been incorporated into the substrate material, e.g., a derivatized or functionalized substrate. Any type of substrate can be used that achieves the specific capture of the reaction product(s).

For example, the substrate can be a flat two dimensional surface or three-dimensional surface, or can be beads. In the case of a flat substrate, the chamber can be formed by walls that extend out from the substrate surface, e.g., as provided by a "mask" as described in an embodiment of an apparatus provided herein, or that are made by etching wells or pillars or channels into the substrate surface in order to create discrete and isolated chambers. Possible materials of which substrates can be made include, but are not limited to, silicon, silicon with a top oxide layer, glass, platinum, gold, polymers and plastic. In a particular embodiment the substrate is a silicon chip or wafer.

Flat substrates may also be modified to contain a thermo-conductive material to facilitate temperature regulation of the reaction mixture in the chamber. In a particular embodiment, the substrate is a flat silicon chip coated with a metal material. Exemplary substrates are described herein and can be used in conjunction with devices described and provided herein.

(b) Capture of Nucleic Acid Reaction Products

Nucleic acid reaction products may be captured in the chamber in a variety of ways. For example, oligonucleotides that specifically hybridize with a reaction product may be attached to the substrate for specific capture of the product.

(i) Surface bound oligonucleotides (1) Synthesis

Oligonucleotides can be synthesized separately and then be attached to a substrate or synthesis can be carried out in situ on the surface of a substrate. Oligonucleotides can be purchased commercially from a number of companies, including, Integrated DNA Technology (IDT; Coralville, Iowa), Fidelity Systems (Gaithersbug, Md.), Proligo (Boulder, Colo.), MWG, Operon (Qiagen; Valencia, Calif.) and Meta-BIOn (Planegg-Martinreid, Germany) and others. Oligonucleotides and oligonucleotide derivatives can be synthesized by standard methods known in the art, e.g. by use of an automated DNA synthesizer (such as are commercially available from Biosearch (Novato, Calif.); Applied Biosystems (Foster City, Calif.) and others), combined with solid supports such as controlled pore glass (CPG) or polystyrene and other resins and with chemical methods, such as phosphoramidite method, the H-phosphonate methods or the phosphotriester method. The oligonucleotides can also be synthesized in solution or on soluble supports. As examples, phosphorothioate oligonucleotides may be synthesized by the method of Stein et al. (1988, Nucl. Acids Res. 16:3209), methylphosphonate oligonucleotides, for example, can be prepared by use of controlled pore glass polymer supports (Sarin et al., 1988, Proc. Natl. Acad. Sci. U.S.A. 85:7448-7451).

Surface bound oligonucleotides are nucleic acids which hybridize to or near the region of interest on the assay product, e.g., extended primer. The capture oligonucleotides generally are not substantially involved in any of the reactions that occur in the chamber. Preferred oligonucleotides have a number of nucleotides sufficient to allow specific hybridization to the target nucleotide sequence. Surface bound oligonucleotides are typically 6 to 30 bases in length and the sequence is chosen to be complementary to that of a particular target nucleic acid (see below types of oligonucleotides). Oligonucleotides can be made of natural nucleotides, modified nucleotides or nucleotide mimetics to alter the specificity to which they hybridize to a complementary sequence or to alter the stability of the formed hybrid.

Altering the specificity can be achieved through incorporating universal bases or sites into a capture sequence or into the precursor of the target nucleic acid. Substituting a base within a sequence by inosine can, for example, lead to universal hybridization towards a polymorphic site in target nucleic acid products (see, e.g., Ohtsuka et al. (1985) J. Biol. Chem. 260:2605; Takahashi et al. (1985) Proc. Natl. Acad. Sci. U.S.A. 82:1931). The stability of a hybrid can be significantly increased by using, for example, RNAs (if directed to a DNA target), locked nucleic acids (LNAs) (Braasch et al. (2001) Chemistry & Biology 8:1-7), peptide nucleic acids (PNAs) (Armitage et al. (1997) Proc. Natl. Acad. Sci. U.S.A. 94:12320-12325), or other modified nucleic acid derivatives, completely or partly within the sequence of the capture or the target nucleic acid. The stability can also be decreased by incorporating one or several abasic sites, non-hybridizing base derivatives or nucleic acid modifications that result in a lower melting temperature, such as phosphorothioates. Both approaches can be used to modulate the melting temperature for almost any sequence and length to a desired melting temperature.

Oligonucleotide Synthesis

Methods of oligonucleotide synthesis, in solution or on solid supports, are well known in the art (see, e.g., Beaucage et al. (1981) Tetrahedron Lett. 22:1859-1862; Sasaki et al. (1993) Technical Information Bulletin T-1792, Beckman Instrument; Seliger et al. (1990) DNA and Cell Biol. 9:691-696).

Oligonucleotide Synthesis In Situ

Oligonucleotide synthesis in situ on glass and silicon surfaces using light-directed synthesis is well known in the art (see, e.g., McCall et al. (1997) J. Am. Chem. Soc. 119:5081-5090; Wallraff et al. (1997) Chemtech 27:22-32; McCall et al. (1996) Proc. Natl. Acad. Sci. USA. 93:13555-13560; Lipshutz et al. (1994) Curr. Opin. Structural Biol. 4:376-380; and Pease et al. (1994) Proc. Natl. Acad. Sci. U.S.A. 91:5022-5026).

(2) Attachment to Substrate

Oligonucleotides can be attached to a substrate which has been chemically derivatized or a substrate such as polymers or plastic having functional groups. Oligonucleotides can be bound to a solid support by a variety of processes, including photolithography, a covalent bond or passive attachment through noncovalent interactions such as ionic interactions, Van der Waal and hydrogen bonds. Oligonucleotides can be covalently attached to the surface via a 5' or 3'-end modification. Linkers are typically used in order to place the oligonucleotide farther away from the surface. For example, if the oligonucleotide is going to be attached via its 5'-end, then the linker would be on the 5'-end directly proceeding the 5' modification. Typical linkers used include hexylethyleneglycol (one or more units) and oligodesoxythymidine $dT_n$ (with n=5-20).

Chemical Derivatization

Various methods may be used for attaching oligonucleotides to surfaces chemically derivatized with reactive functional groups. For example, amino-modified oligos can react with epoxide-activated surfaces to form a covalent bond (see, e.g., Lamture et al. (1994) Nuc. Acids Res. 22:2121-2125]. Similarly, covalent attachment of amino-modified oligonucleotides can be achieved on carboxylic acid-modified surfaces [Stother et al. (2000) J. Am. Chem. Soc. 122:1205-1209), isothiocyanate, amine, thiol (Penchovsky et al. (2000) Nuc. Acids Res. 28:e98 1-6; Lenigk et al. (2001) Langmuir 17:2497-2501), isocyanate (Lindroos et al. (2001) Nuc. Acids Res. 29:e69 1-7) and aldehydemodified surfaces (Zammatteo et al. (2000) Anal. Biochem. 280:143-150).

Typically, silicon surfaces can be chemically derivatized followed by immobilization of oligonucleotides as described herein (see also Benters et al. (2002) Nuc. Acids Res. 30: e10 1-7). For example, after washing the surfaces, the surface is treated with aminopropyltrimethoxysilane to yield an aminosiloxane layer on the surfaces. The surface is activated with the bifunctional crosslinker 1,4-phenylenediisothiocyanate. One isothiocyanate group of the crosslinker reacts with amino functions on the surface, forming a stable thiourea bond. The second, now surface-bound isothiocyanate group is open for the covalent reaction with other molecules with amino groups. In the following step a dendrimeric polyamine, e.g., Starburst (PAMAM) dendrimer, generation 4 with 64 terminal amino groups (e.g., SIGMA-Aldrich, St. Louis, Mo.), reacts with the activated surface to form a homogeneous interlayer on the substrate with a dense amount of covalently attached amino groups. These functions on the surface are again activated with 1,4-phenylenediisothiocyanate. Unreacted amines are blocked with 4-nitro-phenylene isothiocyanate. Amino-modified oligonucleotides are now covalently cross-linked to the activated dendrimer interlayer through the same type of reaction. In the final step, unreacted isothiocyanates are blocked with a small primary amine, like hexylamine.

(3) Arrangement on Substrate

Oligonucleotides are attached to a substrate in discrete known locations. Each location can consist of multiple copies of oligonucleotide having the same sequence. Alternatively, each location can have multiple copies of oligonucleotides having different sequences. This is a preferred arrangement of oligonucleotides for multiplex reactions. Oligonucleotides of different sequence at the same location can be mixed together or segregated into groups of like sequence. For multiplexing, two, three, four, five, six, seven, eight, nine, ten or more different oligonucleotides can be utilized. The number of different oligonucleotides utilized is only limited by the ability to resolve the products bound to each different sequence within one location. For example, U.S. Pat. Nos. 5,990,479 and 6,207,392 provide nanocrystal detection means capable of resolving 100 or more different oligonucleotides.

Different locations on the substrate typically contain oligonucleotides of different sequence. The oligonucleotides at a location typically occupy an area of 0.0025 $mm^2$ to 2.0 $mm^2$ (e.g., 1.4 $mm^2$) with oligonucleotide amounts in the range between 10 amol and 10 pmol. A typical format is a substrate, 20×30 mm in size, with 96, 384 or 1536 locations, in an 8×12, 16×24 or 32×48 pattern and spacings that are equivalent to those on a standard reaction plate (2.25 mm, 1.125 mm or 0.5625 mm center-to-center). In one embodiment, a location is no larger than the diameter of the laser used in the mass spectrometer. Size of the substrate, the total number of locations and the pattern in which the locations are arranged can conform to design aspects and apparatus used for creating an array on the substrate, for liquid handling and/or for analysis. For example, the spacing and spot size can be such that it is dictated by the accuracy and/or the drop size of an instrument that creates the array. The number of locations of oligonucleotides placed in a row or column on a substrate can be such that the laser of a MALDI-TOF mass spectrometer does not encompass more than one location at the same time.

Groups of oligonucleotides can be positioned on the substrate surface in any arrangement. For example, oligonucleotides can be placed in individual wells made in the substrate. The number of wells present on the substrate can vary depending on the size of the substrate, with a 96- or 384-well format often used. The only limitation being that the wells must remain separate and maintain their integrity. Oligonucleotides can be placed on the substrate at discrete known locations in rows or columns that share a common overlying reagent channel. In another example, oligonucleotides can also be arranged on the surface of a totally flat surface in such discrete known locations and in any arrangement. The location can also be subdivided in smaller areas with individual oligonucleotides or mixes of oligonucleotides. Channels or wells for reagents can be created with masks made of the same or a different material placed on top of the substrate. Furthermore, wells and channels on the substrate can be designed in a way that they localize or even separate and sort beads, for example according to their size. In this design, the beads are carriers of the oligonucleotides used for the capturing of reaction product nucleic acids and derivatives.

(4) Types of Oligonucleotides

The sequence, length and composition of an oligonucleotide will vary depending upon the nature of the nucleic acid to be captured. The oligonucleotide can be specific for each assay product or can be complementary to a common region of two or more allelic variants of a polymorphic site. For example, in a primer extension reaction assay, the surface immobilized complement oligonucleotide can hybridize to the extension product that results from both alleles of the polymorphic site. This is because the hybrid does not form with the polymorphic region. The oligonucleotide hybridizes with the extension product 5' to the polymorphic region. But, each oligonucleotide only hybridizes with alleles of a single polymorphic region.

Alternatively, a generic oligonucleotide ("zip code" oligonucleotide) can be immobilized on the substrate. A zip code oligonucleotide can be any length and is typically 6 to 25 nucleotides in length. The captured assay product has a zip code complement sequence to allow for hybridization to the surface-bound oligonucleotide. Zip codes could be shared by assay products used to capture and detect different polymorphisms in one location. Different sets of zip codes and complement zip code sequences can be used to separate assay products of different polymorphic sites in different locations, as single assay products as well as in small groups of different assay products. The use of generic zip code sequences simplifies manufacturing and quality control of the substrate. The described strategies facilitate the processing and analysis of multiplexed samples.

A possible modification of the zip code approach is to incorporate a cleavable site in the extended primer. For example, the zip code sequence can be cleaved from the assay product to create assay products that are more suitable for the method of analysis, like mass spectrometry. The cleavable site can be an enzymatic or base-cleavable site. For example, a single ribonucleotide in a sequence of deoxyribonucleotides is cleavable by ribonucleases or by base. An abasic site can be incorporated during the synthesis of the oligonucleotide or induced by enzymes and chemicals and cleaved under basic conditions or with enzymes. When MALDI-TOF mass spectrometry is used for analysis of reaction products, enzymes or reagents for cleavage can be added to the captured nucleic acid along with matrix. Other alternatives include acid-cleavable sites (e.g., sites that can be cleaved by matrix for mass spectrometry or matrix additives) as in the case of phosphoramidate bonds [see, e.g., Shchepinov et al. (2001) Nucleic Acids Res. 29:3864-3872] or photocleavable sites, such as may be cleaved by a laser in laserbased mass spectrometry. Disulfide bonds can also be used and cleaved in the presence of a reducing agent such as dithiothreitol.

In another embodiment, the surface bound oligonucleotide is the amplification product which becomes attached to an activated substrate or chip. The substrates are activated up to the point of oligonucleotide addition as described herein or in Example 2. Attachment of the PCR product to the surface occurs during and after the PCR. Chemical attachment of the PCR product is achieved through a 5'-modification of the PCR primer(s). Also, passive attachment of the PCR product to the surface can occur via for example, electrostatic interactions, Van der Waals forces and hydrogen bonds. The assay product, e.g., primer extension product, is captured by hybridization to the surface immobilized amplification product.

Alternatively, as previously described, a generic oligonucleotide ("zip code" oligonucleotide) can be immobilized on the substrate. The amplification product has an attached zip code complement sequence to allow for hybridization to the bound oligonucleotide. The amplification product simultaneously captures the assay product. The zip code oligonucleotide can be modified, in a way that the stability of the formed hybrid can be significantly increased, for example, by using RNAs, LNAs, (PNAs) or other modified nucleic acid derivatives, completely or partly within the sequence. Zip code and the corresponding region of the amplification product can as well be permanently crosslinked with each other through reactive groups in the formed hybrid. In another embodiment, a generic zip code oligonucleotide is immobilized on the substrate. One strand of the amplification product is designed to have a single-stranded overhang sequence on one end. After PCR or any other method used for amplification, capture by hybridization is mediated by a third oligonucleotide with a sequence that is to one part complementary to the zip code on the surface, to the other part complementary to the additional overhang sequence on the target strand of the amplification product. Thus mediating the contact between amplification product and zip code sequence on the surface, the formed hybrid can furthermore be used to permanently link the target strand to the surface, for example by using the ligase reaction. The covalent attachment permits the isolation of a single-stranded amplification product by washing the second strand and the mediating oligonucleotide away under suitable buffer conditions. The single strand isolation on the substrate can for example be followed by reactions to identify SNP sites within the immobilized target DNA by primer extension reactions. The assay products are finally captured and conditioned for analysis through hybridizing with the immobilized target DNA.

(c) Capture of Proteins and Peptides

In embodiments where proteins or peptides are assayed, proteins and peptides can be captured through hybridization or other interaction mechanisms to, for example, surface attached oligonucleotides, proteins and surface immobilized enzymes. The study of protein interaction to surface attached oligonucleotides or DNA microarrays is important for learning about regulation and control of gene expression, replication and recombination (Brockman, J. et al. (1999) Journal of the American Chemical Society 121:8044-8051). In addition, understanding how proteins recognize certain oligonucleotide sequences would be instrumental in designing drugs that could be used to regulate expression of therapeutic proteins. Nelson, R. W. et al. (1999, Anal. Chem. 71: 2858-2865) describes a way of epitope tagging proteins where the epitope tags are histidines followed by capturing these tagged proteins to surface immobilized $Ni^{2+}$ chelate. In this technique, it is the histidine tag that is captured through its binding to the $Ni^{2+}$ chelated surface. The $Ni^{2+}$ chelated surface is formed by running a $Ni^{2+}$ buffer over a nitrilotriacetic acid derivitized surface. In another embodiment, the proteins can be captured onto the surface through their binding affinity to surface immobilized enzymes (Nelson, R. W. et al. (1997) Anal. Chem. 69: 4369-4374; Nelson, R. W. et al (2001) Anal. Chem. 73: 1-7; Nedelkov, D. et al. (2000) Analytica Chimica Acta 423: 1-7). Primary amines on the enzyme can be covalently attached to surfaces activated with N-hydroxysuccinimide aminopropylcarbodiimide. MacBeath, G. et al. (2000, Science 289:1760-1762) described another process suitable for use herein where proteins can be immobilized to surfaces to create protein chips. In this embodiment, the lysine residues on the proteins can be covalently attached to, for instance, an aldehyde surface through Schiff base formation. Interaction via capture of other proteins and small molecules to these surface immobilized proteins can then lead to important information about protein function as well as information about the possible therapeutic relevance of small molecules (Lin, S. et al., (2000) Anal. Chem. 72: 2635-2640).

(d) Capture of Small Organic Molecules

The interaction between small organic molecules and proteins can be important in elucidating protein function as well as discovering the potential of a small molecule to be a good drug candidate (MacBeath, G. et al. (2000), Science 289: 1760-1762; Lin, S. et al. (2000) Anal. Chem. 72: 2635-2640). The interactions of small organic molecules with proteins can be studied by immobilizing the proteins of interest to surfaces. In this embodiment, the lysine residues on the proteins can be covalently attached to, for instance, an aldehyde surface through Schiff base formation or an isothiocyanate surface through the formation of a thiourea bond.

(e) Capture of Carbohydrates

Complex carbohydrates such as glycoproteins, glycolipids and proteoglycans are located on the surfaces of cells. Often these carbohydrates are the host receptors for antigens. Elucidating host receptor/antigen interaction can lead to a better understanding of the mechanisms of infectious diseases as well as create opportunities to make drugs that can prevent such diseases. For example, Wang, D et al (Wang, D et al 2002, Nature 20, 275-281), describe a method suitable for use herein of making carbohydrate microarrays to study antibody response to surface immobilized carbohydrate containing antigens. These microarrays are made by spotting carbohydrate antigens onto nitrocellulose covered glass slides. The carbohydrate antigen are immobilized on the nitrocellulose slides through non-covalent interactions.

4. Amplification

It may be necessary to first amplify at least a portion of a nucleic acid target prior to conducting reactions designed to detect, identify or characterize the target. Amplification can be performed, e.g., by PCR and/or LCR etc., according to methods known in the art.

5. Detection of Polymorphisms

Methods of determining the presence or absence of allelic variants can utilize the sense strand or the same position in the antisense strand. Generally, these methods are based on sequence-specific polynucleotides, oligonucleotides, probes and primers. Any method known to those of skill in the art for detecting a specific nucleotide within a nucleic acid sequence or for determining the identity of a specific nucleotide in a nucleic acid sequence is applicable. Several such general nucleic acid detection assays are known (see, e.g., U.S. Pat. No. 6,030,778).

Also provided are methods for detecting single nucleotide polymorphisms. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

6. Analysis of Reaction Products (a) Mass Spectrometry

Nucleic acids can also be analyzed by detection methods and protocols, particularly those that rely on mass spectrometry (see, e.g., U.S. Pat. Nos. 5,605,798, 6,043,031, 6,197, 498, and International Patent Application No. WO 96/29431, allowed co-pending U.S. application Ser. No. 08/617,256, allowed co-pending U.S. application Ser. No. 08/744,481, U.S. Application Ser. No. 08/990,851, International PCT Application No. WO 98/20019). These methods can be automated (see, e.g., co-pending U.S. application Ser. No. 09/285, 481, which describes an automated process line). Particular among the methods of analysis herein are those involving the primer oligonucleotide base extension reaction (MassEXTEND®) with mass spectrometry for detection (see e.g., U.S. Pat. Nos. 6,043,031 and 6,197,498, patent application Ser. Nos. 09/287,681, 09/287,682, and 09/287,679, International PCT Application No. PCT/US97/20444 (WO 98/20166), and based upon U.S. Pat. Nos. 5,900,481, 6,024,925, 6,074,823, application Ser. Nos. 08/746,055, 08/786,988, 08/933,792, 08/746,055, and 08/786,988; see, also U.S. application Ser. No. 09/074,936, and published International PCT Application No. PCT/US97/20195 (WO 98/20020)).

When analyses are performed using mass spectrometry, particularly MALDI-TOF-MS, nanoliter volumes of sample are loaded on, such that the resulting spot is about, or smaller than, the size of the laser spot. It has been found that when this is achieved, the results from the mass spectrometric analysis are quantitative. The area under the peaks in the resulting mass spectra are proportional to concentration (when normalized and corrected for background). Methods for preparing and using such chips are described in U.S. Pat. No. 6,024,925, co-pending U.S. application Ser. Nos. 08/786,988, 09/364, 774, 09/371,150 and 09/297,575; see, also International PCT Application No. PCT/US97/20195 (WO 98/20020). Chips and kits for performing these analyses are commercially available from SEQUENOM (San Diego, Calif.) as MassARRAY®. MassARRAY® relies on the fidelity of the enzymatic primer extension reactions combined with the miniaturized array and MALDI-TOF (Matrix-Assisted Laser Desorption Ionization-Time of Flight) mass spectrometry to deliver results rapidly. It accurately distinguishes single base changes in the size of DNA fragments relating to genetic variants without tags.

(i) Conditioning of the Reaction Sample

For performing MALDI-TOF-MS analysis of, for example, hybridized nucleic acids, it is necessary to desalt the sample and to eventually remove all other components that might interfere with the analysis of the biomolecule. Such conditioning can be carried out by washing away salts, buffer compounds and any reagents or products not bound to the solid support.

(ii) Matrix

Once capture of the biomolecules onto the surface has taken place and desalting and conditioning has been completed, matrix is added to the surface to permit analysis by MALDI-TOF mass spectrometry. Typically 1 mL to 100 mL of matrix is added to the surface. For oligonucleotides 3-hydroxypicolinic acid matrix can be used. The matrix composition is for instance, 300 mM 3-hydroxypicolinic acid, 35 mM diammonium citrate in 10% acetonitrile:water. For proteins, peptides and small molecules, matrices such as sinapinic acid (50 mM sinapinic acid, 1:2 acetonitrile/water with the 1.5% trifluoroacetic acid v/v), 2,5-dihydroxybenzoic acid (2,5-dihydroxybenzoic acid+10% 5'-methoxysalicylic acid) and alpha-cyano-4-hydroxycinnamic acid (~50 mM, dissolved in 1:2 acetonitrile/water with 1.5% trifluoroacetic acid v/v) can be used. The matrix can be nanodispensed using, for example, a GeSim nanodispenser, Cartesian dispenser, Microdrop nanodispenser and Robodesign pintool.

(iii) Multiplexing

Multiplex methods allow for the simultaneous detection of more than one polymorphic region in a particular gene or several genes. Multiplexing at a single location on the substrate can be achieved by utilizing a different immobilized capture oligonucleotide for the product of each set of specific assay reactions.

In another embodiment, multiplexing can be carried using several locations, each having immobilized one or more capture oligonucleotides, and sharing a common reagent channel. The set of capture oligonucleotides are different for each locations. At a specific location the same capture oligonucleotide can be used or there can be different capture nucleotides, depending on whether or not the assay products share a common sequence. Many different assay reactions can be carried out in the reagent channel and the products are sorted to specific locations on the substrate, as they have sequences that are complementary to the capture oligonucleotide. An advantage to this arrangement for multiplexing is that it is possible to use a limited number of mass values to detect the assay products and that these can be the same for products bound at each of the different locations.

(b) Fluorescence-Based Methods

Many systems for fluorescence-based detection of biomolecules are known in the art. Such systems may be used in the analysis and detection of reaction products in the methods provided herein.

The following examples are included for illustrative purposes only and are not intended to limit the scope of the invention. The practice of methods and development of the products provided herein employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription and Translation (B. D. Hames & S. J. Higgins eds. 1984); Culture of Animal Cells (R. I. Freshney, Alan R. Liss, Inc., 1987); Immobilized Cells and Enzymes (IRL Press, 1986); B. Perbal, A Practical Guide To Molecular Cloning (1984); the treatise, Methods In Enzymology (Academic Press, Inc., New York); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds., Immunochemical Methods In Cell and Molecular Biology (Mayer and Walker, eds., Academic Press, London, 1987); Handbook of Experimental Immunology, Volumes I-IV (D. M. Weir and C. C. Blackwell, eds., 1986; Manipulating the Mouse Embryo, (Cold Spring Harbor Laboratory Press, Cold Spring Harbor, N.Y., 1986).

EXAMPLE 1

Isolation of DNA from Blood Sample

An exemplary method for isolation of DNA from the blood is 20 detailed as follows, including optional steps.

Cell Lysis

Ten ml of EDTA whole blood was centrifuged for no more than 15 min at 2000×g. The 1-2 ml buffy coat was transferred to a 15 ml tube. Nine ml of red cell lysate (RCL) was added to the tube and the tube was vortexed vigorously until there were no red cell clumps and incubated for 10 min at room temperature. The tube was inverted once during the incubation and subsequently centrifuged for 10 min at 2000×g. The supernatant was poured off into a biohazard container leaving behind a visible white cell pellet and 100-200 ul of residual liquid. The tubes were run across test tube rack to resuspend the white blood cells in the residual supernatant. Five ml RCL wash was added to the white cells and the tubes were inverted to resuspend the white cells. The tubes were centrifuged for 10 min at 2000×g and the supernatant was poured into a biohazard container leaving behind a visible white cell pellet and 100-200 ul of residual liquid. The tubes were run across the test tube rack to resuspend the white blood cells in the residual supernatant. 4.5 ml of white cell lysate (WCL) was added to the tube and pipetted up and down (with a transfer pipet) until completely mixed. Typically, no incubation was required.

Protein Precipitation

To precipitate protein, 2 ml of protein precipitation solution was added to the cell lysate and vortexed vigorously at high speed for 20 sec to mix the protein precipitation solution uniformly with the cell lysate. The mixed solution was centrifuged for 10 min at 3000×g. The precipitated proteins will form a tight, dark brown pellet. The supernatant containing the DNA should be clear.

DNA Precipitation

The supernatant containing the DNA was poured into a clean 15 ml tube, containing 6 ml 100% Isopropanol. The sample was mixed by inverting gently until the white threads of DNA were visible. Each sample was visually checked for DNA and the size of the sample was estimated. If it was relatively small, it did not get as much TE buffer in step 1 of DNA hydration. The sample was centrifuged for 3 min at 2000×g and the DNA was visible as a small white pellet. The supernatant was poured into alcohol waste container and the tube was tapped on paper towel to remove excess alcohol. Five ml of 70% Ethanol:water was added and the tube was inverted several times to wash the DNA pellet. The tube was centrifuged for 1 min at 2000×g. The ethanol was carefully poured off into an alcohol waste container. The pellet may be loose at this stage so pour slowly and watch pellet. The tube was drained on clean absorbent paper and the DNA was dried with the tube inverted for 10 minutes.

DNA Hydration

To rehydrate the DNA, 1000 ul of 1×TE was added and allowed to rehydrate overnight at room temperature. The DNA was then pipetted into a labeled tube with the correct lid per the sample's group. If there were clots in the hydrated DNA then the purification step that follows was carried, out. The DNA samples were stored by ethnic group, sex and age in at 2-8° C. refrigerator.

Purification of Hydrated DNA

If there were clots in the hydrated DNA, then after the rehydration step the DNA was reisolated. Five ml new WCL was added and incubated for 30 min to 1 hour at 65° C. The sample was cooled to room temperature and 1 ml of protein precipitation solution was added to the cell lysate. The protein precipitation protocol was repeated.

EXAMPLE 2

Chemical Derivatization of Surfaces

To prewash the chips, the silicon surfaces are immersed in a solution of chromic acid for 12 hours followed by 3 washes with DI water.

Silation of Chips:

In order to make 1% APTMS/95% acetone:water v/v, 1.6 mL of aminopropyltrimethoxysilane was combined with 158.4 mL 95% acetone:water and added to the chips and reacted for 5 minutes at room temperature (RT) with shaking. The surfaces were then rinsed with methanol (5×) followed by acetone (5×). The surfaces were then placed in vacuum oven at 110° C. for 25 minutes.

First activation with 57 mM 1,4 phenylenediisothiocyante:

1.76 g of 1,4 phenylenediisothiocyanate was dissolved in 160 mL of 10% pyridine:DMF and the solution was added to the surfaces and reacted for 2 hours at RT with orbital shaking. The surfaces were then washed with methanol (3×) followed by acetone (3×) at RT with manual shaking.

Amine Dendrimer Step:

1.25% v/v starburst dendrimer generation 4.0 (64 amino-groups) in 10% pyridine:DMF was produced by combining 2 mL dendrimer with 158 mL 10% pyridine:DMF. This solution was added to the chips and reacted overnight (e.g., >5hrs) at RT with orbital shaking. The surfaces were then washed with ethanol (3×) and water (3×).

Second Activation with 100 mM 1,4 phenylenediisothiocyante:

3.2 g of 1,4 phenylenediisothiocyanate were dissolved in 160 mL of 10% pyridine:DMF and added to the chips and reacted for 3 hours at RT with shaking. The surfaces were washed with methanol (3×) followed by acetone (3×).

Amine Capping with 0.1M 4-nitrophenylisothiocyante:

4.8 g of 4-nitrophenylisothiocyanate were dissolved in 160 mL of 10% pyridine:DMF and the solution was added to the chips and reacted for 1 hour at RT with orbital shaking. The surfaces were then washed with methanol (3×) and acetone (3×).

Oligonucleotide Spotting:

25 μM 5'-amino modified oligonucleotide solution in formamide solution were spotted onto the surfaces using a pin-tool spotting instrument. The volume spotted was ~50-100 mL. A pattern of a 96 oligonucleotide array was generated. The surfaces were allowed to sit for two days. The unbound oligonucleotide was then washed off with 5×SSC/50% formamide buffer solution for 30 min 60° C., deionized water to container at 60° C. for 30 min, followed by a wash with acetone at RT.

25 Isothiocyanate Capping with 2% Hexylamine:

In order to block unreacted isothiocyanates, 3.2 mL hexylamine was combined with 156.8 mL 10% pyridine:DMF and added to the chips and reacted for 1 hour at 60° C. The surfaces were then washed with 5×SSC/50% formamide at RT (2×) followed by two DI water washes at RT and one acetone quick rinse. The chips were then stored under vacuum in a vacuum desiccator until further use.

EXAMPLE 3

4-Plex Massextend® Assay

A. Hybridization Chip:

With the method described related to FIG. 4 backside metallized silicon chips, 20×30 mm with a thickness of 700 pm, were prepared. To these substrates four different capture oligonucleotides were attached, complementary to four extension primers for polymorphic sites within human genes related to cystic fibrosis. Each chip had a pattern of 12 lanes with 8 distinct target locations in each. Each of the four capture oligonucleotides was present in two repeats in each lane. The sequences of the four capture oligonucleotides were as follows: CF3659-3-com: 5'-caa gtc aac caa acc-3'-X-NH2 (SEQ ID NO:1); CF508delF-com: 5'-ggt gtt tcc tat gat g-3'-X-NH2 (SEQ ID NO:2); CF711+1-com: 5'-tca tca aat ttg ttc ag-3'-X-NH2 (SEQ ID NO:3); and CF621-2-com: 5'-tta taa atc aaa cta aac a-3'-X-NH2 (SEQ ID NO:4). Each sequence was attached to the silicon surface via a 3'-end amino-modification (NH2=3'-Amino-C7 modifier, Glen Research, Sterling, Va.) and spaced by one hexaethyleneglycol unit (X). Each location on the chip surface had a diameter of 600-800 μm and oligonucleotide surface density of 15 to 100 fmole/mm$^2$.

B. Multiplexed PCR and Dephosphorylation:

4-plex PCR was performed according to standard protocols on standard thermocycler, using genomic DNA prepared according to Example 1 and the following set of primers: CFX 4-F3 cca aag cag tac agc ctc t (SEQ ID NO:5) and CFX 4-R cga tac aga ata tat gtg cca tg (SEQ ID NO:6); CFX 5-F5 gct gtc aag ccg tgt tct a (SEQ ID NO:7) and CFX 5-R5 gta taa ttt ata aca ata gtg cc (SEQ ID NO:8) for an amplicon of 132 bp on exon 5; CFX10-F7 gat tat ggg aga act gga g (SEQ ID NO:9) and CFX10-R gtg tga agg gtt cat atg c (SEQ ID NO:10) for an amplicon of 225 bp on exon 10 and CFX19-F2 cca agt gac aaa tag caa gtg t (SEQ ID NO:11) and CFX19-R2 acg tgt gaa ttc tca ata atc ata (SEQ ID NO:12) for an amplicon of 240 bp on exon 19. The PCR reactions were performed with concentrations of 50 nM for each PCR-primer, 500 μM for each dNTP, with 5 mM MgCl$_2$ and 0.1 units HotStar Taq polymerase for a total volume of 5 μl in 1×PCR buffer (Quiagen, Valencia, Calif.). The PCR reaction was followed by a treatment with shrimp alkaline phosphatase (SAP), 0.3 units in 2 μl Thermosequenase buffer (Pharmacia, Peapack, N.J.), incubated for 20 min at 37° C. followed by 5 min at 85° C.

C. MassEXTEND Reaction and Hybridization on a Chip Substrate:

4-plex MassEXTEND cocktails were prepared according to standard protocols with the following set of primers: CF3659-3 ggt ttg gtt gac ttg (SEQ ID NO:13); CF508delF cat cat agg aaa cac ca (SEQ ID NO:14); CF711+1 ctg aac aaa ttt gat gaa (SEQ ID NO:15) and CF621-2 tgt tta gtt tga ttt ata aga ag (SEQ ID NO:16). The final concentrations were 50 μM for ddNTPs and dNTPs, 600 nM for each MassEXTEND primer and 0.063 U/μl for Thermosequenase in 1×Thermosequenase buffer (Pharmacia). The MassEXTEND cocktail was mixed with the PCR/SAP reaction in a ratio of 2:7 from Example 3B. Such reaction mixture was then applied to the hybridization chip. Two methods of thermocycling were performed. In one embodiment, a standard in situ thermocycling block with long cycle times (approximately 150 min for 55 cycles, MJ Research) was used with the whole chip covered by a FrameSeal™ cell (MJ Research, Waltham, Mass.) with a total volume of 125 µl. In another embodiment, the chip was covered with a polydimethylsiloxane mask (PDMS) and placed in a cartridge (as set forth in FIG. 1), creating six 4 µl- and six 2 µl-channels above the chip surface. The channels were equipped with an inlet and outlet. After filling the chip with the reaction mixture the channels were sealed and thermocycled using a fast thermocycler as described herein. Typical cycling conditions were: initially 20 seconds at 95° C., then 40-55 cycles with 5 seconds at 95° C., 5 seconds at 56° C. and 5 seconds at 72° C. The cooling and heating rates were extremely high, compared to commercially available thermocyclers, leading to a total processing time of 15 min for 45 cycles. In both set-ups, the chip was cooled to room temperature or to 4° C., separated from the masks and directly placed into a bath of 5×SSC buffer at room temperature. After gently shaking for 5 min on an orbital shaker, a second 5×SSC buffer wash, followed by 2 washes with 70 mM ammonium citrate and one brief wash with nanopure water were performed.

D. Matrix Application and MALDI-ToF MS Analysis:

After conditioning, matrix solution was applied to the 96 locations with hybridized target nucleic acid on the chips. 2×7nl of a 300 mM solution of 3-HPA (3-hydroxy picolinic acid) in water or water/acetonitrile 9:1 v/v and with an additive of 32 mM diammonium citrate was dispensed with a Microdrop piezonanodispenser (Microdrop GmbH; Norderstedt, Germany). After crystallization the chip was fixed to a MALDI-TOF MS target holder. Manual analysis was performed on a Voyager DE instrument (Applied Biosystems, Foster City, Calif.), while automated runs were performed on a Biflex MS instrument (Bruker; Bremen, Germany) using SpectroTYPER-RT software (SEQUENOM, San Diego, Calif.).

EXAMPLE 4

A. PCR on a 96 Well Chip Substrate with Fast Thermocycling Protocol:

A PCR amplification reaction was conducted using the fast thermocycling chips and methods provided herein. With the method described related to FIG. 4, backside metallized silicon chips, 20×30 mm with a thickness of 700 µm, were prepared. One of the chips was silanized with dimethyldichlorosilane. Next, the chip and gasket were treated with the commercial blocking agent casein (available from Pierce, Rockford, Ill.) in Tris buffer for 1 hour at room temperature. The gasket was made of silicon rubber and glued to the chip surface to create 96 reaction wells with maximum volumes of 3 µl on the substrate. The chip was placed in a cartridge and connected to the fast thermocycler, as described herein. A PCR cocktail was prepared as set forth in Table 1 below:

TABLE 1

PCR Cocktail

| | Working concentrations: |
|---|---|
| 46.72 µl H20 | |
| 8.00 µl 10X PCR buffer (15 mM MgCl2) | |
| 6.40 µl 10 mg/mL bovine serum albumin (BSA) | → 0.8 mg/mL |
| 3.20 µl 25 mM McCl2 | → 2.5 mM (with buffer MgCl2) |
| 3.20 µl 5 mM dNTP's | → 200 µM |
| 3.20 µl 5 µM primers | → 200 nM |
| 1.28 µl 5 U/µl DNA Polymerase enzyme | → 0.08 U/µL |
| 8.00 µl genomic DNA (5 ng/µl) | → 0.05 ng/µL |
| 72.0 µL Total Volume of Cocktail | |

Next, 0.5 to 1.5 µl of the PCR cocktail mix was loaded into each reaction well of the chip. The chip was sealed and equipped with a lid that was heated to 80-95° C. and cycled as follows:

| 1) Genomic DNA melt (1X): | 95° C. - 2 minutes |
| 2) Sequence Amplification (40X): | 95° C. - 2 seconds |
| | 56° C. - 5 seconds |
| | 72° C. - 5 seconds |

The enzyme used for fast cycled PCR was HotMaster Taq DNA Polymerase (Eppendorf GmbH, Hamburg, Germany). The PCR buffer used was HotStar Taq buffer (Qiagen; Valencia, Calif.). The results indicate that the PCR reaction yielded the desired amplification product.

B. PCR on a 12 Channel Chip Substrate with Fast Thermocycling

In another embodiment, a PCR amplification reaction was conducted as described in Example 4A, using a fast thermocycling multichannel chip described herein. With the method described related to FIG. 4, backside metallized silicon chips, 20×30 mm with a thickness of 700 µm, were prepared. One of the chips was silanized with dimethyldichlorosilane. Next, the chip and gasket were treated with the commercial blocking agent casein (available from Pierce, Rockford, Ill.) in Tris buffer for 1 hour at room temperature. The PCR reaction was loaded into the channels of the chip and 45 thermocycles were run as follows:

| 1) Genomic DNA melt (1X): | 95° C. - 2 minutes |
| 2) Sequence Amplification (45X): | 95° C. - 5 seconds |
| | 56° C. - 5 seconds |
| | 72° C. - 5 seconds |

At the end of the 95° C. hold, a pulse of canned air (VariAir obtained from Peca Products, Janesville, Wis.) was sprayed manually on the underside of the chip. Cooling was observed to take place from 95° C. to 56° C. in approximately 1 to 2 seconds, which translates to a cooling rate between 18.5 and 39° C. per second. The results indicate that the PCR reaction yielded the desired amplification product.

EXAMPLE 5

Chip-based Cleavage of Zip Code-Oligonucleotides with Ribo-Cutting Sites

As set forth herein, the use of generic capture sequences or zip code oligonucleotides can be an advantageous modification of the basic concept. This example describes a method for effectively purifying an extension primer using an additional zip code sequences on the substrate, and performing RNase A induced cleavage on the surface prior to MALDIMS analysis.

Preparation of Hybridization Chips:

Backside metallized silicon chips (20×30 mm with a thickness of 700 mm) were prepared using the method described in Example 2. Four different capture oligonucleotides were attached to the substrate. The sequences were the complement to four address or zip code sequences. Each chip has a pattern corresponding to 12 lanes with 8 locations in each or a total of 96 spots. Each of the four capture oligonucleotides was present in two repeats in each lane. The sequences of the four capture oligonucleotides were as follows:

Seq#6NH2:
5'-tta gct ggt gtg tg-3'-X-NH2;    (SEQ ID NO:17)

Seq#14NH2:
5'-tgc agc agc cat tc-3'-X-NH2;    (SEQ ID NO:18)

Seq#15NH2:
5'-ctc gct agt gga tt-3'-X-NH2;    (SEQ ID NO:19)
and

Seq#19NH2:
5'-cgg aga cgc ata ta-3'-X-NH2.    (SEQ ID NO:20)

Each sequence was attached to the silicon surface via a 3'-end amino-modification (NH2=3'-Amino-C7 modifier, Glen Research, Sterling, Va.) and spaced by one hexaethyleneglycol unit (X). Each location on the chip surface had a diameter of 600-800 μm and oligonucleotide surface density of 15 to 100 fmole/mm².

Design of Zip Code-Oligonucleotides:

The following 3 sequences were synthesized, using standard oligonucleotide synthesis techniques and were purchased from two different vendors (Fidelity Systems, Inc., Gaithersburg, Md. or IDT, Inc., Coralville, Iowa):

1) ribo2(seq6)rU:
5'-cac aca cca gct aaa (rU)cc caa tag gct tat cca ag (MW = 10624Da; SEQ ID NO:21);

2) Hyb15:
5'-aat cca cta gcg ag (MW = 4257Da; SEQ ID NO:22);
and

3) CF621(seq19)rU:
5'-tat atg cgt ctc cgt gtt tag (rU)tt tga ttt ata aga ag (MW = 11721Da; SEQ ID NO:23).

Sequence Hyb15 is a 14mer desoxyribooligonucleotide and designed to hybridize to the capture sequence Seq#15NH2 on the substrate. Each of the other two oligonucleotides possesses a single site, where desoxythymidine is substituted by the ribonucleotide analog uridine (rU). In solution these DNA/RNA chimeras were rapidly cleaved at the ribonucleotide when treated with the enzyme RNase A (Sigma/Aldrich, St. Louis, Mo.). The cleavage products for ribo2(seq6)rU were:

Fragment 1:
                                    (SEQ ID NO:24)
5'-cac aca cca gct aa(rU)-3'phosphate, MW = 4885.2Da
and Fragment 2:
                                    (SEQ ID NO:25)
5'-ccc aat agg ctt atc caa g, MW = 5756.8Da The cleavage products for CF621(seq19)rU were:

Fragment 1:
                                    (SEQ ID NO:26)
5'-tat atg cgt ctc cgt gtt tag (rU)-3'phosphate, MW = 6804Da
and Fragment 2:
                                    (SEQ ID NO:27)
5'-ttt gat tta taa gaa g, MW = 4934Da.

The 5'-end of the full length oligonucleotides ribo2(seq6)rU and CF621(seq19)rU, as well as the corresponding fragments 1 were designed to hybridize to positions on the substrate with capture oligonucleotide Seq#6NH2 or Seq#19NH2.

Hybridization:

The substrate with the four different capture sequences was covered with a FrameSeal™cell (MJ Research, Waltham, Mass.). A 1 μM mix of the oligonucleotides Hyb15, CF621 (seq19)rU and ribo2(seq6)rU was prepared in 5×SSC buffer with 0.1% SDS and 25 μg/mL BSA. A 125 μl solution was added to the FrameSeal cell on the substrate and covered with a lid. The substrate was incubated for 5 min at 95° C., 20 min at 35° C., 2 min at 95° C. and again 30 min at 35° C. The chip was cooled to 4° C. and directly placed into a bath of 5×SSC buffer at room temperature. After gently shaking for 5 min on an orbital shaker, a second 5×SSC buffer wash was performed, followed by 2 washes with 70 mM ammonium citrate and one brief wash with nanopure water.

Cleavage with RNase A and MALDI-MS Analysis:

To all 24 spots on the substrate with the capture sequence Seq#14NH2 a 1 μM solution of oligonucleotide ribo2(seq6) rU was dispensed (100 nL or 100 fmole in water, spotted with a GeSiM nanodispenser). These two oligonucleotides do not undergo hybridization and were used as an internal control for effective cleavage with RNase A. The chip was placed in a cartridge and connected to a chip-based fast thermocycler as described herein. For running a controlled current through the backside metal layer of the substrate, the chip surface was heated to approximately 50° C. A solution of 0.001 U/μl RNase A (Sigma-Aldrich, St. Louis, Mo.) in nanopure water was prepared and dispensed, while the chip was kept at 50° C. The thermocycler was connected to a solenoid nanodispenser (Cartesian Technologies, Irvine, Calif.). The instrument dispensed 3×30 nL to each of the 60 central spots on the substrate. Because the solution evaporates fast, in approximately 10 seconds, the total reaction time for cleavage with RNase A was therefore 30 seconds. The substrate was cooled down to RT and removed from the cartridge. Matrix solution was applied to the 96 locations with hybridized target nucleic acid on the chips. 2×7 nl of a 300 mM solution of 3-HPA (3-hydroxy picolinic acid) in water with an additive of 32 mM diammonium citrate were dispensed with a Microdrop piezo-nanodispenser (Microdrop GmbH; Norderstedt, Germany). After crystallization, the chip was fixed to a MALDI-TOF MS target holder and analyzed in fully automated runs on a Biflex MS instrument (Bruker; Bremrn, Germany) using Spectro-TYPER-RT software (SEQUENOM, Inc., San Diego, Calif.).

Typically the method results in strong MALDI-MS signals and an estimated cleavage of 70% for the internal control (ribo2(seq6)rU on capture sequence Seq#14NH2, main signals at 4885.2 m/z and 5756.8 m/z, minor signal at 10624 m/z for uncleaved full length oligonucleotide). Spots with 14-mer Hyb15 on capture sequence Seq#15NH2 gave an intense single peak at 4257 m/z and indicated effective hybridization and sample preparation. The signals from spots with capture sequences Seq#6NH2 or Seq#19NH2 were weak, due to ineffective hybridization, however, these signals still indicate the effective cleavage at the ribonucleotide. Full length oligonucleotides are usually not detectable. Signals correspond to Fragment 1 at 4885.2 and Fragment 2 at 5756.8 m/z for the cleavage of sequence ribo2(seq6)rU or respectively to Fragment 1 at 6804 and Fragment 2 at 4934 m/z for the cleavage of sequence CF621 (seq19)rU.

Since modifications will be apparent to those of skill in this art, it is intended that this invention be limited only by the scope of the appended claims. All modifications, variations, or equivalent arrangements and implementations that are within the scope of the attached claims should therefore be considered within the scope of the invention.

The invention claimed is:

1. A method of performing a chemical reaction on a substrate having at least one target location that contains a sample of biological material, comprising;

(a) mounting a substrate on a mounting region in a cartridge base that supports the substrate in a fixed position relative to the base with the top surface of the substrate facing away from the cartridge base, the substrate having a plurality of target locations that each contain a sample of biological material;

(b) locating a reaction containment member over the top surface of the substrate, (c) aligning the reaction containment member with the substrate while moving the reaction containment member relative to the substrate such that a bottom surface of the reaction containment member is juxtaposed with a top surface of the substrate and the reaction containment member and the substrate collectively form a plurality of chambers, each chamber being located directly over at least one respective target location, the reaction containment member having an outer peripheral shape and size which substantially conforms with the shape and size of the substrate when viewed from the top, the aligning step further comprising releasably securing a cartridge cover in mating engagement with the cartridge base to secure the substrate and reaction containment member in position with the bottom surface of the reaction containment member juxtaposed with the top surface of the substrate and each chamber located over at least one respective target location, the cartridge cover having an aperture positioned over the substrate and reaction containment member when the cartridge cover is secured to the cartridge base;

(d) dispensing selected fluids into chambers through ports in the reaction containment member which are accessible through the aperture in the cartridge cover, whereby each target location is exposed to a selected fluid;

(e) conducting a chemical reaction within each chamber using the selected fluid;

(f) heating the substrate to increase the temperature within the same chambers in which steps (d) and (e) were previously performed; wherein steps (d), (e) and (f) are all performed while the substrate remains in a stationary position, wherein the reaction containment member has a back plate and the step of aligning the reaction containment member with the substrate comprises coupling the back plate and reaction containment member to the cartridge cover while allowing some movement between the back plate and cartridge cover, and moving the cartridge cover into mating engagement with the cartridge base such that an alignment member between the cartridge base and back plate moves the reaction containment member into alignment with the substrate such that each chamber is located over at least one respective target location on the substrate.

2. A method as defined in claim 1, wherein each chamber is formed by a respective flow channel in the reaction containment member, each flow channel having an inlet port and an outlet port, the step of dispensing fluids into the respective chambers comprising dispensing fluids through at least the inlet ports, the method additionally comprising sealing the inlet ports and the outlet ports by inserting hollow pins into the inlet and outlet ports.

3. The method as defined in claim 1, wherein each sample of biological material includes a respective target biomolecule and the step of conducting a chemical reaction in each chamber comprises performing one or more reactions of a target biomolecule at said at least one target location in the presence of the surface of the substrate, wherein the reaction(s) is performed substantially in solution and the substrate comprises one or more target detection location(s) in contact with the solution; capturing one or more reaction products of the one or more reactions on the surface of the substrate at the target detection location, wherein the capture is achieved through a non-covalent interaction between the reaction product(s) and the surface of the substrate or a moiety attached to the surface of the substrate; and detecting the reaction product or products at the target detection location.

4. The method of claim 3, wherein capture is achieved through ionic interactions, Van der Waals forces or hydrogen bonds.

5. The method of claim 3, wherein capture is achieved through hybridization of the reaction product(s) with a capture oligonucleotide attached to the surface of the substrate.

6. The method of claim 3, wherein the reaction product(s) is detected by mass spectrometry.

7. The method of claim 3, wherein the surface of the substrate forms an interior surface of a chamber.

8. The method of claim 3, wherein the biomolecule is a nucleic acid.

9. The method of claim 8, wherein at least one reaction of the nucleic acid comprises amplification of at least a portion of the nucleic acid molecule.

10. The method of claim 9, wherein the nucleic acid is amplified by an amplification procedure selected from the group consisting of: polymerase chain reaction (PCR), ligase chain reaction (LCR) and strand displacement amplification (SDA).

11. The method of claim 9, wherein the step of heating the substrate comprises at least one temperature thermocycle comprising heating and cooling of the surface of the substrate to change the temperature of the solution in contact with said one or more target detection location(s).

12. The method of claim 11, wherein the rate of heating is selected from the range of about 3° C./second up to about 100° C./second.

13. The method of claim 11, wherein the rate of heating is selected from the group consisting of rates of heating of at least about: 3, 4, 5, 6, 7, 8, 9, 10, 15, 20, 25, 30, 35, 40, 45, 50, 60, 65, 70, 75, 80, 85, 90, 95 and at least about 100° C./second.

14. The method of claim 11, wherein the heating is achieved using thermal conductivity or electrical conductivity.

15. The method of claim 11, wherein the rate of cooling is selected from the range of about 3° C./second up to about 100° C./second.

16. The method of claim 11, wherein the rate of cooling is selected from the group consisting of rates of cooling of at least about: 3, 4, 5, 6, 7, 8, 9, 10, 15, 20, 25, 30, 35, 40, 45, 50, 60, 65, 70, 75, 80, 85, 90, 95 and at least about 100° C./second.

17. The method of claim 11, wherein the cooling is achieved using water, air or a cold block.

18. The method of claim 8, wherein at least one reaction of the nucleic acid comprises extension of an oligonucleotide primer hybridized to the nucleic acid.

19. The method of claim 18, wherein the extended primer is captured on the surface of the substrate.

20. The method of claim 18, wherein at least one reaction undergoes at least one temperature thermocycle comprising heating and cooling of the surface of the substrate to change the temperature of the solution in contact with said one or more target detection location(s).

21. The method of claim 20, wherein the rate of heating is selected from the range of about 3° C./second up to about 100° C./second.

22. The method of claim 20, wherein the rate of heating is selected from the group consisting of rates of heating of at least about: 3, 4, 5, 6, 7, 8, 9, 10, 15, 20, 25, 30, 35, 40, 45, 50, 60, 65, 70, 75, 80, 85, 90, 95 and at least about 100° C./second.

23. The method of claim 20, wherein the heating is achieved using thermal conductivity or electrical conductivity.

24. The method of claim 20, wherein the rate of cooling is selected from the range of about 3° C./second up to about 100° C./second.

25. The method of claim 20, wherein the rate of cooling is selected from the group consisting of rates of cooling of at least about: 3, 4, 5, 6, 7, 8, 9, 10, 15, 20, 25, 30, 35, 40, 45, 50, 60, 65, 70, 75, 80, 85, 90, 95 and at least about 100° C./second.

26. The method of claim 20, wherein the cooling is achieved using water, air or a cold block.

27. The method of claim 3, wherein prior to step (c), matrix is deposited at the target detection location and detection is performed by MALDI mass spectrometry.

28. The method of claim 3, wherein the temperature difference from within a single reaction chamber is selected from $\leq$:2.0° C., 1.5° C., 1.0° C., 0.5° C. and $\leq$0.3°C.

29. The method of claim 1, wherein the temperature difference between different reaction chambers is selected from $\leq$:1.0° C., 0.5° C., 0.4° C., 0.3° C., 0.2° C. and $\leq$0.1° C.

30. The method of claim 1, wherein each sample of biological material comprises at least a target nucleic acid molecule, the target locations each comprise at least one discrete target detection location, and the step of conducting a chemical reaction comprises hybridizing a single-stranded portion of a target nucleic acid molecule with an oligonucleotide that is complementary to a region of the single-stranded portion of the target nucleic acid in solution and in the presence of a capture moiety at a discrete target detection location on a substrate; exposing the hybridized nucleic acid and oligonucleotide to conditions that permit extension of the oligonucleotide; capturing the product(s) of the extension reaction on the surface of the substrate at the discrete target detection location, wherein the capture is achieved through a non-covalent interaction between the product(s) and the surface of the substrate or a moiety attached to the surface of the substrate; and carrying out at least initiation of a detection process for determining the identity of a nucleotide in the captured reaction product(s) of the target nucleic acid molecule at the respective discrete target detection locations on the surface of the substrate.

31. The method of claim 30, wherein capture is achieved through ionic interactions, Van der Waals forces or hydrogen bonds.

32. The method of claim 30, wherein capture is achieved through hybridization of the reaction product(s) with a capture oligonucleotide attached to the surface of the substrate.

33. The method of claim 30, wherein the reaction product(s) is detected by mass spectrometry.

34. The method of claim 30, wherein the surface of the substrate forms an interior surface of a chamber.

35. The method of claim 30, wherein capturing of the product(s) of the extension reaction comprises capturing an extended primer through hybridization of the extended primer to an oligonucleotide immobilized on the surface of the substrate.

36. The method of claim 35, wherein hybridization occurs between an additional region of nucleotides in a primer portion of the extended primer that hybridizes to a complementary sequence of nucleotides in the immobilized oligonucleotide, wherein the additional region of nucleotides in the primer portion of the extended primer does not occur in the target nucleic acid molecule.

37. The method of claim 36, wherein the primer contains a site that can be selectively cleaved.

38. The method of claim 30, wherein prior to detection, matrix is deposited at the target detection location and detection is performed by MALDI mass spectrometry.

39. The method of claim 30, wherein the conditions that permit extension of the oligonucleotide comprise at least one temperature thermocycle comprising heating and cooling.

40. The method of claim 39, wherein the rate of heating is selected from the range of about 3° C./second up to about 100° C./second.

41. The method of claim 39, wherein the rate of heating is selected from the group consisting of rates of heating of at least about: 3, 4, 5, 6, 7, 8, 9, 10, 15, 20, 25, 30, 35, 40, 45, 50, 60, 65, 70, 75, 80, 85, 90, 95 and at least about 100° C./second.

42. The method of claim 39, wherein the heating is achieved using thermal conductivity or electrical conductivity.

43. The method of claim 39, wherein the rate of cooling is selected from the range of about 3° C./second up to about 100° C./second.

44. The method of claim 39, wherein the rate of cooling is selected from the group consisting of rates of cooling of at least about: 3, 4, 5, 6, 7, 8, 9, 10; 15, 20, 25, 30, 35, 40, 45, 50, 60, 65, 70, 75, 80, 85, 90, 95 and at least about 100° C./second.

45. The method of claim 39, wherein the cooling is achieved using water, air or a cold block.

46. The method of claim 30, wherein the surface of the substrate is enclosed by one or more reaction chambers within a removable reaction containment member.

47. The method of claim 46, wherein the temperature difference from within a single reaction chamber is selected from $\leq$:2.0° C., 1.5° C., 1.0° C., 0.5° C. and $\leq$0.3° C.

48. The method of claim 46, wherein the temperature difference between different reaction chambers is selected from $\leq$:1.0° C., 0.5° C., 0.4° C., 0.3° C., 0.2° C. and <0.1° C.

49. The method of claim 1, wherein each target location comprises one or more target detection location(s) and the step of conducting a chemical reaction within each chamber comprises performing one or more reactions of a target biomolecule in the presence of the surface of the substrate within the respective chamber and in contact with the selected fluid, capturing one or more products of the reaction or reactions on the surface of the substrate at the target detection location; and detecting the reaction product or products at the target detection location.

50. The method of claim 49, wherein the capture is achieved through a non-covalent interaction between the product(s) and the surface of the substrate or a moiety attached to the surface of the substrate.

51. A method of performing a chemical reaction on a substrate having at least one target location that contains a sample of biological material, comprising; (a) locating a reaction containment member on the top surface of the substrate such that the reaction containment member and the substrate collectively form a chamber directly over the at least one target location; (b) dispensing a fluid into the chamber to expose the at least one target location to the fluid; (c) conducting a chemical reaction within the chamber using the fluid; (d) heating the substrate to increase the temperature within the same chamber in which steps (b) and (c) were previously performed; wherein steps (b)-(c) are performed while the substrate remains in a stationary position, and heating the substrate comprises: forming a first set of contacts between a resistive coating on the substrate and two or more electrical conductors, wherein at least one of the electrical conductors in the first set is coupled in series to a first resistor which is not part of the resistive coating on the substrate; forming a second set of contacts between the resistive coating on the substrate and two or more electrical conductors, wherein at least one of the electrical conductors in the second set is coupled in series to a second resistor which is not part of the resistive coating on the substrate; applying a first electrical current to the first set of electrical conductors so that the current flows from the first set of electrical contacts to the second set of contacts through the resistive coating; wherein the resistive value of the first and second resistors differ with respect to one another to thereby vary the current at one contact with respect to another electrical contact.

* * * * *

SEQUENCE LISTING

<160> NUMBER OF SEQ ID NOS: 27

<210> SEQ ID NO 1
<211> LENGTH: 17
<212> TYPE: DNA
<213> ORGANISM: Artificial Sequence
<220> FEATURE:
<223> OTHER INFORMATION: Capture oligonucleotide CF3659-3-com
<220> FEATURE:
<221> NAME/KEY: misc_feature
<222> LOCATION: (16)..(16)
<223> OTHER INFORMATION: n = hexaethyleneglycol
<220> FEATURE:
<221> NAME/KEY: misc_feature
<222> LOCATION: (17)..(17)
<223> OTHER INFORMATION: n = 3'-Amino-C7 modifier

<400> SEQUENCE: 1
caagtcaacc aaaccnn                                                  17

<210> SEQ ID NO 2
<211> LENGTH: 18
<212> TYPE: DNA
<213> ORGANISM: Artificial Sequence
<220> FEATURE:
<223> OTHER INFORMATION: Capture oligonucleotide CF508delF-com
<220> FEATURE:
<221> NAME/KEY: misc_feature
<222> LOCATION: (17)..(17)
<223> OTHER INFORMATION: n = hexaethyleneglycol
<220> FEATURE:
<221> NAME/KEY: misc_feature
<222> LOCATION: (18)..(18)
<223> OTHER INFORMATION: n = 3'-Amino-C7 modifier

<400> SEQUENCE: 2
ggtgtttcct atgatgnn                                                 18

<210> SEQ ID NO 3
<211> LENGTH: 19
<212> TYPE: DNA
<213> ORGANISM: Artificial Sequence
<220> FEATURE:
<223> OTHER INFORMATION: Capture oligonucleotide CF711 + 1-com
<220> FEATURE:
<221> NAME/KEY: misc_feature
<222> LOCATION: (18)..(18)
<223> OTHER INFORMATION: n = hexaethyleneglycol
<220> FEATURE:
<221> NAME/KEY: misc_feature
<222> LOCATION: (19)..(19)
<223> OTHER INFORMATION: n = 3'-Amino-C7 modifier

<400> SEQUENCE: 3
tcatcaaatt tgttcagnn                                                19

<210> SEQ ID NO 4
<211> LENGTH: 21

```
<212> TYPE: DNA
<213> ORGANISM: Artificial Sequence
<220> FEATURE:
<223> OTHER INFORMATION: Capture oligonucleotide CF621-2-com
<220> FEATURE:
<221> NAME/KEY: misc_feature
<222> LOCATION: (20)..(20)
<223> OTHER INFORMATION: n = hexaethyleneglycol
<220> FEATURE:
<221> NAME/KEY: misc_feature
<222> LOCATION: (21)..(21)
<223> OTHER INFORMATION: n = 3'-Amino-C7 modifier

<400> SEQUENCE: 4
ttataaatca aactaaacan n                                            21

<210> SEQ ID NO 5
<211> LENGTH: 19
<212> TYPE: DNA
<213> ORGANISM: Artificial Sequence
<220> FEATURE:
<223> OTHER INFORMATION: Primer CFX 4-F3

<400> SEQUENCE: 5
ccaaagcagt acagcctct                                               19

<210> SEQ ID NO 6
<211> LENGTH: 23
<212> TYPE: DNA
<213> ORGANISM: Artificial Sequence
<220> FEATURE:
<223> OTHER INFORMATION: Primer CFX 4-R

<400> SEQUENCE: 6
cgatacagaa tatatgtgcc atg                                          23

<210> SEQ ID NO 7
<211> LENGTH: 19
<212> TYPE: DNA
<213> ORGANISM: Artificial Sequence
<220> FEATURE:
<223> OTHER INFORMATION: Primer CFX 5-F5

<400> SEQUENCE: 7
gctgtcaagc cgtgttcta                                               19

<210> SEQ ID NO 8
<211> LENGTH: 23
<212> TYPE: DNA
<213> ORGANISM: Artificial Sequence
<220> FEATURE:
<223> OTHER INFORMATION: Primer CFX 5-R5

<400> SEQUENCE: 8
gtataattta taacaatagt gcc                                          23

<210> SEQ ID NO 9
<211> LENGTH: 19
<212> TYPE: DNA
<213> ORGANISM: Artificial Sequence
<220> FEATURE:
<223> OTHER INFORMATION: Primer CFX 10-F7

<400> SEQUENCE: 9
gattatggga gaactggag                                               19

<210> SEQ ID NO 10
<211> LENGTH: 19
```

```
<212> TYPE: DNA
<213> ORGANISM: Artificial Sequence
<220> FEATURE:
<223> OTHER INFORMATION: Primer CFX 10-R

<400> SEQUENCE: 10
gtgtgaaggg ttcatatgc                                                 19

<210> SEQ ID NO 11
<211> LENGTH: 22
<212> TYPE: DNA
<213> ORGANISM: Artificial Sequence
<220> FEATURE:
<223> OTHER INFORMATION: Primer CFS 19-F2

<400> SEQUENCE: 11
ccaagtgaca aatagcaagt gt                                             22

<210> SEQ ID NO 12
<211> LENGTH: 24
<212> TYPE: DNA
<213> ORGANISM: Artificial Sequence
<220> FEATURE:
<223> OTHER INFORMATION: Primer CFX 19-R2

<400> SEQUENCE: 12
acgtgtgaat tctcaataat cata                                           24

<210> SEQ ID NO 13
<211> LENGTH: 15
<212> TYPE: DNA
<213> ORGANISM: Artificial Sequence
<220> FEATURE:
<223> OTHER INFORMATION: Primer CF3659-3

<400> SEQUENCE: 13
ggtttggttg acttg                                                     15

<210> SEQ ID NO 14
<211> LENGTH: 17
<212> TYPE: DNA
<213> ORGANISM: Artificial Sequence
<220> FEATURE:
<223> OTHER INFORMATION: Primer CF508delF

<400> SEQUENCE: 14
catcatagga aacacca                                                   17

<210> SEQ ID NO 15
<211> LENGTH: 18
<212> TYPE: DNA
<213> ORGANISM: Artificial Sequence
<220> FEATURE:
<223> OTHER INFORMATION: Primer CF711 + 1

<400> SEQUENCE: 15
ctgaacaaat ttgatgaa                                                  18

<210> SEQ ID NO 16
<211> LENGTH: 23
<212> TYPE: DNA
<213> ORGANISM: Artificial Sequence
<220> FEATURE:
<223> OTHER INFORMATION: Primer CF621-2

<400> SEQUENCE: 16
tgtttagttt gatttataag aag                                            23
```

<210> SEQ ID NO 17
<211> LENGTH: 16
<212> TYPE: DNA
<213> ORGANISM: Artificial Sequence
<220> FEATURE:
<223> OTHER INFORMATION: Capture oligonucleotide Seq#6NH2
<220> FEATURE:
<221> NAME/KEY: misc_feature
<222> LOCATION: (15)..(15)
<223> OTHER INFORMATION: n = hexaethyleneglycol
<220> FEATURE:
<221> NAME/KEY: misc_feature
<222> LOCATION: (16)..(16)
<223> OTHER INFORMATION: n = 3'-Amino-C7 modifier

<400> SEQUENCE: 17
ttagctggtg tgtgnn                                              16

<210> SEQ ID NO 18
<211> LENGTH: 16
<212> TYPE: DNA
<213> ORGANISM: Artificial Sequence
<220> FEATURE:
<223> OTHER INFORMATION: Capture oligonucleotide Seq#14NH2
<220> FEATURE:
<221> NAME/KEY: misc_feature
<222> LOCATION: (15)..(15)
<223> OTHER INFORMATION: n = hexaethyleneglycol
<220> FEATURE:
<221> NAME/KEY: misc_feature
<222> LOCATION: (16)..(16)
<223> OTHER INFORMATION: n = 3'-Amino-C7 modifier

<400> SEQUENCE: 18
tgcagcagcc attcnn                                              16

<210> SEQ ID NO 19
<211> LENGTH: 16
<212> TYPE: DNA
<213> ORGANISM: Artificial Sequence
<220> FEATURE:
<223> OTHER INFORMATION: Capture oligonucleotide Seq#15NH2
<220> FEATURE:
<221> NAME/KEY: misc_feature
<222> LOCATION: (15)..(15)
<223> OTHER INFORMATION: n = hexaethyleneglycol
<220> FEATURE:
<221> NAME/KEY: misc_feature
<222> LOCATION: (16)..(16)
<223> OTHER INFORMATION: n = 3'-Amino-C7 modifier

<400> SEQUENCE: 19
ctcgctagtg gattnn                                              16

<210> SEQ ID NO 20
<211> LENGTH: 16
<212> TYPE: DNA
<213> ORGANISM: Artificial Sequence
<220> FEATURE:
<223> OTHER INFORMATION: Capture oligonucleotide Seq#19NH2
<220> FEATURE:
<221> NAME/KEY: misc_feature
<222> LOCATION: (15)..(15)
<223> OTHER INFORMATION: n = hexaethyleneglycol
<220> FEATURE:
<221> NAME/KEY: misc_feature
<222> LOCATION: (16)..(16)
<223> OTHER INFORMATION: n = 3'-Amino-C7 modifier

<400> SEQUENCE: 20
cggagacgca tatann                                              16

```
<210> SEQ ID NO 21
<211> LENGTH: 36
<212> TYPE: DNA
<213> ORGANISM: Artificial Sequence
<220> FEATURE:
<223> OTHER INFORMATION: Synthetic oligonucleotide ribo2 (seq6) rU
<220> FEATURE:
<221> NAME/KEY: misc_feature
<222> LOCATION: (16)..(16)
<223> OTHER INFORMATION: n = uridine

<400> SEQUENCE: 21
cacacaccag ctaaanccca atagggctta tccaag                                 36

<210> SEQ ID NO 22
<211> LENGTH: 14
<212> TYPE: DNA
<213> ORGANISM: Artificial Sequence
<220> FEATURE:
<223> OTHER INFORMATION: Synthetic oligonucleotide Hyb15

<400> SEQUENCE: 22
aatccactag cgag                                                         14

<210> SEQ ID NO 23
<211> LENGTH: 38
<212> TYPE: DNA
<213> ORGANISM: Artificial Sequence
<220> FEATURE:
<223> OTHER INFORMATION: Synthetic oligonucleotide CF621 (seq19) rU
<220> FEATURE:
<221> NAME/KEY: misc_feature
<222> LOCATION: (22)..(22)
<223> OTHER INFORMATION: n = uridine

<400> SEQUENCE: 23
tatatgcgtc tccgtgttta gntttgattt ataagaag                               38

<210> SEQ ID NO 24
<211> LENGTH: 15
<212> TYPE: DNA
<213> ORGANISM: Artificial Sequence
<220> FEATURE:
<223> OTHER INFORMATION: ribo2 (seq6) rU cleavage fragment 1
<220> FEATURE:
<221> NAME/KEY: misc_feature
<222> LOCATION: (15)..(15)
<223> OTHER INFORMATION: n = uridine

<400> SEQUENCE: 24
cacacaccag ctaan                                                        15

<210> SEQ ID NO 25
<211> LENGTH: 19
<212> TYPE: DNA
<213> ORGANISM: Artificial Sequence
<220> FEATURE:
<223> OTHER INFORMATION: ribo2 (seq6) rU cleavage fragment 2

<400> SEQUENCE: 25
cccaataggc ttatccaag                                                    19

<210> SEQ ID NO 26
<211> LENGTH: 22
<212> TYPE: DNA
<213> ORGANISM: Artificial Sequence
<220> FEATURE:
<223> OTHER INFORMATION: SF621 (seq19) rU cleavage fragment 1
```

```
<220> FEATURE:
<221> NAME/KEY: misc_feature
<222> LOCATION: (22)..(22)
<223> OTHER INFORMATION: n = uridine

<400> SEQUENCE: 26
tatatgcgtc tccgtgttta gn                                              22

<210> SEQ ID NO 27
<211> LENGTH: 16
<212> TYPE: DNA
<213> ORGANISM: Artificial Sequence
<220> FEATURE:
<223> OTHER INFORMATION: CF621 (seq19) rU cleavage fragment 2

<400> SEQUENCE: 27
tttgatttat aagaag                                                     16
```